(12) United States Patent
Sista et al.

(10) Patent No.: US 8,927,296 B2
(45) Date of Patent: Jan. 6, 2015

(54) METHOD OF REDUCING LIQUID VOLUME SURROUNDING BEADS

(75) Inventors: Ramakrishna Sista, San Diego, CA (US); Vamsee Pamula, Cary, NC (US); Arjun Sudarsan, Carlsbad, CA (US); Vijay Srinivasan, Durham, NC (US); Prasanna Thwar, Los Altos, CA (US)

(73) Assignee: Advanced Liquid Logic, Inc., San Diego, CA (US)

( * ) Notice: Subject to any disclaimer, the term of this patent is extended or adjusted under 35 U.S.C. 154(b) by 773 days.

(21) Appl. No.: 12/992,939

(22) PCT Filed: May 18, 2009

(86) PCT No.: PCT/US2009/044305
§ 371 (c)(1),
(2), (4) Date: Jan. 3, 2011

(87) PCT Pub. No.: WO2009/140671
PCT Pub. Date: Nov. 19, 2009

(65) Prior Publication Data
US 2011/0091989 A1  Apr. 21, 2011
US 2014/0057363 A9  Feb. 27, 2014

Related U.S. Application Data

(63) Continuation-in-part of application No. 11/639,663, filed on Dec. 15, 2006, now Pat. No. 8,492,168.

(60) Provisional application No. 61/053,693, filed on May 16, 2008, provisional application No. 61/075,250, filed on Jun. 24, 2008, provisional application No. 61/082,314, filed on Jul. 21, 2008, provisional application No. 61/085,773, filed on Aug. 1, 2008, provisional application No. 61/160,607, filed on Mar. 16, 2009, provisional application No. 60/745,058, filed on Apr. 18, 2006, provisional application No. 60/745,039, filed on Apr. 18, 2006, provisional application No. 60/745,059, filed on Apr. 18, 2006, provisional application No. 60/745,914, filed on Apr. 28, 2006, provisional application No. 60/745,950, filed on Apr. 28, 2006, provisional application No. 60/746,797, filed on May 9, 2006, provisional application No. 60/746,801, filed on May 9, 2006, provisional application No. 60/806,412, filed on Jun. 30, 2006, provisional application No. 60/807,104, filed on Jul. 12, 2006, provisional application No. 60/745,043, filed on Apr. 18, 2006.

(51) Int. Cl.
*G01N 1/40* (2006.01)
*B01L 3/00* (2006.01)
*G01N 35/00* (2006.01)

(52) U.S. Cl.
CPC ........ *B01L 3/502792* (2013.01); *G01N 1/4077* (2013.01); *G01N 35/0098* (2013.01); *B01L 3/502761* (2013.01); *B01L 2200/0673* (2013.01); *B01L 2300/0816* (2013.01); *B01L 2300/0819* (2013.01); *B01L 2300/089* (2013.01); *B01L 2400/0406* (2013.01); *B01L 2400/0415* (2013.01); *B01L 2400/0427* (2013.01); *B01L 2400/043* (2013.01); *B01L 2400/0487* (2013.01); *G01N 2035/00564* (2013.01)
USPC ............................................. 436/174

(58) Field of Classification Search
CPC ................... G01N 35/0098; G01N 35/00564; G01N 35/00574; G01N 1/4077; G01N 2035/00564; G01N 2035/00574; B01L 3/502761; B01L 3/502792; B01L 2300/089; B01L 2400/0415; B01L 2400/0427; B01L 2400/043
USPC ............. 436/43, 174, 149; 422/50, 504, 68.1, 422/82.01, 82.02; 435/79, 7.4
See application file for complete search history.

(56) References Cited

U.S. PATENT DOCUMENTS

| | | | |
|---|---|---|---|
| 3,878,519 A * | 4/1975 | Eaton | ............................. 347/75 |
| 4,636,785 A | 1/1987 | Le Pesant | |
| 5,181,016 A | 1/1993 | Lee et al. | |
| 5,486,337 A | 1/1996 | Ohkawa et al. | |
| 6,063,339 A | 5/2000 | Tisone et al. | |
| 6,130,098 A | 10/2000 | Handique et al. | |

| Patent No. | Date | Inventor |
|---|---|---|
| 6,294,063 B1 | 9/2001 | Becker et al. |
| 6,565,727 B1 | 5/2003 | Shenderov |
| 6,773,566 B2 | 8/2004 | Shenderov |
| 6,790,011 B1 | 9/2004 | Le Pesant et al. |
| 6,911,132 B2 | 6/2005 | Pamula et al. |
| 6,924,792 B1 | 8/2005 | Jessop |
| 6,977,033 B2 | 12/2005 | Becker et al. |
| 6,989,234 B2 | 1/2006 | Kolar et al. |
| 7,052,244 B2 | 5/2006 | Fouillet et al. |
| 7,163,612 B2 | 1/2007 | Sterling et al. |
| 7,189,359 B2 | 3/2007 | Yuan et al. |
| 7,211,223 B2 | 5/2007 | Fouillet et al. |
| 7,255,780 B2 | 8/2007 | Shenderov |
| 7,328,979 B2 | 2/2008 | Decre et al. |
| 7,329,545 B2 | 2/2008 | Pamula et al. |
| 7,439,014 B2 | 10/2008 | Pamula et al. |
| 7,458,661 B2 | 12/2008 | Kim et al. |
| 7,531,072 B2 | 5/2009 | Roux et al. |
| 7,547,380 B2 | 6/2009 | Velev |
| 7,569,129 B2 | 8/2009 | Pamula et al. |
| 7,641,779 B2 | 1/2010 | Becker et al. |
| 7,727,466 B2 | 6/2010 | Meathrel et al. |
| 7,727,723 B2 | 6/2010 | Pollack et al. |
| 7,759,132 B2 | 7/2010 | Pollack et al. |
| 7,763,471 B2 | 7/2010 | Pamula et al. |
| 7,815,871 B2 | 10/2010 | Pamula et al. |
| 7,816,121 B2 | 10/2010 | Pollack et al. |
| 7,822,510 B2 | 10/2010 | Paik et al. |
| 7,851,184 B2 | 12/2010 | Pollack et al. |
| 7,875,160 B2 | 1/2011 | Jary |
| 7,901,947 B2 | 3/2011 | Pollack et al. |
| 7,919,330 B2 | 4/2011 | De Guzman et al. |
| 7,922,886 B2 | 4/2011 | Fouillet et al. |
| 7,939,021 B2 | 5/2011 | Smith et al. |
| 7,943,030 B2 | 5/2011 | Shenderov |
| 7,989,056 B2 | 8/2011 | Plissonnier et al. |
| 7,998,436 B2 | 8/2011 | Pollack |
| 8,007,739 B2 | 8/2011 | Pollack et al. |
| 8,041,463 B2 | 10/2011 | Pollack et al. |
| 8,048,628 B2 | 11/2011 | Pollack et al. |
| 8,075,754 B2 | 12/2011 | Sauter-Starace et al. |
| 8,088,578 B2 | 1/2012 | Hua et al. |
| 8,093,062 B2 | 1/2012 | Winger et al. |
| 8,093,064 B2 | 1/2012 | Shah et al. |
| 8,137,917 B2 | 3/2012 | Pollack et al. |
| 8,147,668 B2 | 4/2012 | Pollack et al. |
| 8,202,686 B2 | 6/2012 | Pamula et al. |
| 8,208,146 B2 | 6/2012 | Srinivasan et al. |
| 8,221,605 B2 | 7/2012 | Pollack et al. |
| 8,236,156 B2 | 8/2012 | Sarrut et al. |
| 8,268,246 B2 | 9/2012 | Srinivasan et al. |
| 8,287,711 B2 | 10/2012 | Pollack et al. |
| 8,304,253 B2 | 11/2012 | Yi et al. |
| 8,313,698 B2 | 11/2012 | Pollack et al. |
| 8,317,990 B2 | 11/2012 | Pamula et al. |
| 8,342,207 B2 | 1/2013 | Raccurt et al. |
| 8,349,276 B2 | 1/2013 | Pamula et al. |
| 8,364,315 B2 | 1/2013 | Sturmer et al. |
| 8,388,909 B2 | 3/2013 | Pollack et al. |
| 8,389,297 B2 | 3/2013 | Pamula et al. |
| 8,394,249 B2 | 3/2013 | Pollack et al. |
| 8,426,213 B2 | 4/2013 | Eckhardt et al. |
| 8,440,392 B2 | 5/2013 | Pamula et al. |
| 8,444,836 B2 | 5/2013 | Fouillet et al. |
| 2002/0005354 A1 | 1/2002 | Spence et al. |
| 2002/0036139 A1 | 3/2002 | Becker et al. |
| 2002/0043463 A1 | 4/2002 | Shenderov |
| 2002/0058332 A1 | 5/2002 | Quake et al. |
| 2002/0143437 A1 | 10/2002 | Handique et al. |
| 2003/0164295 A1 | 9/2003 | Sterling |
| 2003/0183525 A1 | 10/2003 | Elrod et al. |
| 2003/0205632 A1 | 11/2003 | Kim et al. |
| 2004/0031688 A1 | 2/2004 | Shenderov |
| 2004/0055891 A1 | 3/2004 | Pamula et al. |
| 2004/0058450 A1 | 3/2004 | Pamula et al. |
| 2004/0231987 A1 | 11/2004 | Sterling et al. |
| 2005/0056569 A1 | 3/2005 | Yuan et al. |
| 2005/0106742 A1* | 5/2005 | Wahl .......... 436/149 |
| 2006/0021875 A1 | 2/2006 | Griffith et al. |
| 2006/0054503 A1 | 3/2006 | Pamula et al. |
| 2006/0164490 A1 | 7/2006 | Kim et al. |
| 2006/0194331 A1 | 8/2006 | Pamula et al. |
| 2006/0231398 A1 | 10/2006 | Sarrut et al. |
| 2007/0023292 A1 | 2/2007 | Kim et al. |
| 2007/0037294 A1 | 2/2007 | Pamula et al. |
| 2007/0045117 A1 | 3/2007 | Pamula et al. |
| 2007/0064990 A1 | 3/2007 | Roth |
| 2007/0086927 A1 | 4/2007 | Natarajan et al. |
| 2007/0207513 A1 | 9/2007 | Sorensen et al. |
| 2007/0217956 A1 | 9/2007 | Pamula et al. |
| 2007/0241068 A1 | 10/2007 | Pamula et al. |
| 2007/0242105 A1 | 10/2007 | Srinivasan et al. |
| 2007/0242111 A1 | 10/2007 | Pamula et al. |
| 2007/0243634 A1 | 10/2007 | Pamula et al. |
| 2007/0264723 A1 | 11/2007 | Kim et al. |
| 2007/0267294 A1 | 11/2007 | Shenderov |
| 2007/0275415 A1 | 11/2007 | Srinivasan et al. |
| 2008/0006535 A1 | 1/2008 | Paik et al. |
| 2008/0038810 A1 | 2/2008 | Pollack et al. |
| 2008/0044893 A1 | 2/2008 | Pollack et al. |
| 2008/0044914 A1 | 2/2008 | Pamula et al. |
| 2008/0050834 A1 | 2/2008 | Pamula et al. |
| 2008/0053205 A1 | 3/2008 | Pollack et al. |
| 2008/0105549 A1 | 5/2008 | Pamela et al. |
| 2008/0124252 A1 | 5/2008 | Marchand et al. |
| 2008/0142376 A1 | 6/2008 | Fouillet et al. |
| 2008/0151240 A1 | 6/2008 | Roth |
| 2008/0210558 A1 | 9/2008 | Sauter-Starace et al. |
| 2008/0247920 A1 | 10/2008 | Pollack et al. |
| 2008/0264797 A1 | 10/2008 | Pamula et al. |
| 2008/0274513 A1 | 11/2008 | Shenderov et al. |
| 2008/0281471 A1 | 11/2008 | Smith et al. |
| 2008/0283414 A1 | 11/2008 | Monroe et al. |
| 2008/0302431 A1 | 12/2008 | Marchand et al. |
| 2008/0305481 A1 | 12/2008 | Whitman et al. |
| 2009/0014394 A1 | 1/2009 | Yi et al. |
| 2009/0042319 A1 | 2/2009 | De Guzman et al. |
| 2009/0127123 A1 | 5/2009 | Raccurt et al. |
| 2009/0134027 A1 | 5/2009 | Jary |
| 2009/0142564 A1 | 6/2009 | Plissonnier et al. |
| 2009/0155902 A1 | 6/2009 | Pollack et al. |
| 2009/0192044 A1 | 7/2009 | Fouillet |
| 2009/0260988 A1 | 10/2009 | Pamula et al. |
| 2009/0263834 A1 | 10/2009 | Sista et al. |
| 2009/0280251 A1 | 11/2009 | De Guzman et al. |
| 2009/0280475 A1 | 11/2009 | Pollack et al. |
| 2009/0280476 A1 | 11/2009 | Srinivasan et al. |
| 2009/0283407 A1 | 11/2009 | Shah et al. |
| 2009/0288710 A1 | 11/2009 | Viovy et al. |
| 2009/0291433 A1 | 11/2009 | Pollack et al. |
| 2009/0304944 A1 | 12/2009 | Sudarsan et al. |
| 2009/0311713 A1 | 12/2009 | Pollack et al. |
| 2009/0321262 A1 | 12/2009 | Adachi et al. |
| 2010/0025242 A1 | 2/2010 | Pamula et al. |
| 2010/0025250 A1 | 2/2010 | Pamula et al. |
| 2010/0028920 A1 | 2/2010 | Eckhardt |
| 2010/0032293 A1 | 2/2010 | Pollack et al. |
| 2010/0041086 A1 | 2/2010 | Pamula et al. |
| 2010/0048410 A1 | 2/2010 | Shenderov et al. |
| 2010/0062508 A1 | 3/2010 | Pamula et al. |
| 2010/0068764 A1 | 3/2010 | Sista et al. |
| 2010/0087012 A1 | 4/2010 | Shenderov et al. |
| 2010/0096266 A1 | 4/2010 | Kim et al. |
| 2010/0116640 A1 | 5/2010 | Pamula et al. |
| 2010/0118307 A1 | 5/2010 | Srinivasan et al. |
| 2010/0120130 A1 | 5/2010 | Srinivasan et al. |
| 2010/0126860 A1 | 5/2010 | Srinivasan et al. |
| 2010/0130369 A1 | 5/2010 | Shenderov et al. |
| 2010/0140093 A1 | 6/2010 | Pamula et al. |
| 2010/0143963 A1 | 6/2010 | Pollack |
| 2010/0151439 A1 | 6/2010 | Pamula et al. |
| 2010/0190263 A1 | 7/2010 | Srinivasan et al. |
| 2010/0194408 A1 | 8/2010 | Sturmer et al. |
| 2010/0221713 A1 | 9/2010 | Pollack et al. |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0258441 A1 | 10/2010 | Sista et al. |

| | | | |
|---|---|---|---|
| 2010/0270156 A1 | 10/2010 | Srinivasan et al. | |
| 2010/0279374 A1 | 11/2010 | Sista et al. | |
| 2010/0282608 A1 | 11/2010 | Srinivasan et al. | |
| 2010/0282609 A1 | 11/2010 | Pollack et al. | |
| 2010/0307917 A1 | 12/2010 | Srinivasan et al. | |
| 2010/0320088 A1 | 12/2010 | Fouillet et al. | |
| 2010/0323405 A1 | 12/2010 | Pollack et al. | |
| 2011/0086377 A1 | 4/2011 | Thwar et al. | |
| 2011/0091989 A1 | 4/2011 | Sista et al. | |
| 2011/0097763 A1 | 4/2011 | Pollack et al. | |
| 2011/0100823 A1 | 5/2011 | Pollack et al. | |
| 2011/0104725 A1 | 5/2011 | Pamula et al. | |
| 2011/0104747 A1 | 5/2011 | Pollack et al. | |
| 2011/0104816 A1 | 5/2011 | Pollack et al. | |
| 2011/0114490 A1 | 5/2011 | Pamula et al. | |
| 2011/0118132 A1 | 5/2011 | Winger et al. | |
| 2011/0180571 A1 | 7/2011 | Srinivasan et al. | |
| 2011/0186433 A1 | 8/2011 | Pollack et al. | |
| 2011/0203930 A1 | 8/2011 | Pamula et al. | |
| 2011/0209998 A1 | 9/2011 | Shenderov | |
| 2011/0213499 A1 | 9/2011 | Sturmer et al. | |
| 2011/0303542 A1 | 12/2011 | Srinivasan et al. | |
| 2011/0311980 A1 | 12/2011 | Pollack et al. | |
| 2012/0018306 A1 | 1/2012 | Srinivasan et al. | |
| 2012/0132528 A1 | 5/2012 | Shenderov et al. | |
| 2012/0165238 A1 | 6/2012 | Pamula et al. | |

FOREIGN PATENT DOCUMENTS

| | | | |
|---|---|---|---|
| JP | 2006329899 A | 12/2006 | |
| JP | 2006329904 A | 12/2006 | |
| WO | 0069565 A1 | 11/2000 | |
| WO | 0073655 A1 | 12/2000 | |
| WO | 2004029585 A1 | 4/2004 | |
| WO | 2004030820 | 4/2004 | |
| WO | 2005047696 A1 | 5/2005 | |
| WO | 2006013303 A1 | 2/2006 | |
| WO | 2006070162 A1 | 7/2006 | |
| WO | 2006081558 | 8/2006 | |
| WO | 2006124458 A2 | 11/2006 | |
| WO | 2006127451 A2 | 11/2006 | |
| WO | 2006134307 A1 | 12/2006 | |
| WO | 2006138543 | 12/2006 | |
| WO | 2007003720 A1 | 1/2007 | |
| WO | 2007012638 A1 | 2/2007 | |
| WO | 2007033990 A1 | 3/2007 | |
| WO | 2007048111 | 4/2007 | |
| WO | 2007120240 A2 | 10/2007 | |
| WO | 2007120241 A2 | 10/2007 | |
| WO | 2007123908 A2 | 11/2007 | |
| WO | 2008051310 A2 | 5/2008 | |
| WO | 2008055256 A3 | 5/2008 | |
| WO | 2008068229 A1 | 6/2008 | |
| WO | 2008091848 A2 | 7/2008 | |
| WO | 2008101194 A2 | 8/2008 | |
| WO | 2008106678 A1 | 9/2008 | |
| WO | 2008109664 A1 | 9/2008 | |
| WO | 2008112856 A1 | 9/2008 | |
| WO | 2008116209 A1 | 9/2008 | |
| WO | 2008116221 A1 | 9/2008 | |
| WO | 2008118831 A2 | 10/2008 | |
| WO | 2008124846 A2 | 10/2008 | |
| WO | 2008131420 A2 | 10/2008 | |
| WO | 2008134153 A1 | 11/2008 | |
| WO | 2009002920 A1 | 12/2008 | |
| WO | 2009003184 A1 | 12/2008 | |
| WO | 2009011952 A1 | 1/2009 | |
| WO | 2009021173 A1 | 2/2009 | |
| WO | 2009021233 A2 | 2/2009 | |
| WO | 2009026339 A2 | 2/2009 | |
| WO | 2009029561 A2 | 3/2009 | |
| WO | 2009032863 A2 | 3/2009 | |
| WO | 2009052095 A1 | 4/2009 | |
| WO | 2009052123 A2 | 4/2009 | |
| WO | 2009052321 A2 | 4/2009 | |
| WO | 2009052345 A1 | 4/2009 | |
| WO | 2009052348 A2 | 4/2009 | |
| WO | 2009076414 | 6/2009 | |
| WO | 2009086403 A2 | 7/2009 | |
| WO | 2009111769 A2 | 9/2009 | |
| WO | 2009135205 A2 | 11/2009 | |
| WO | 2009137415 A2 | 11/2009 | |
| WO | 2009140373 A2 | 11/2009 | |
| WO | 2009140671 A2 | 11/2009 | |
| WO | 2010006166 A2 | 1/2010 | |
| WO | 2010009463 A2 | 1/2010 | |
| WO | 2010019782 A2 | 2/2010 | |
| WO | 2010027894 A2 | 3/2010 | |
| WO | 2010042637 A2 | 4/2010 | |
| WO | 2010077859 A3 | 7/2010 | |

OTHER PUBLICATIONS

Lehmann, U. et al. "Two dimensional magnetic manipulation of microdroplets on a chip." Transducers '05 (2005) 1 D3.2.*
Pollack, M. G. et al. "Electrowetting-based actuation of droplets for integrated microfluidics." Lab on a Chip (2002) 2 96-101.*
Chakrabarty, "Automated Design of Microfluidics-Based Biochips: connecting Biochemistry of Electronics CAD", IEEE International Conference on Computer Design, San Jose, CA, Oct. 1-4, 2006, 93-100.
Chakrabarty et al., "Design Automation Challenges for Microfluidics-Based Biochips", DTIP of MEMS & MOEMS, Montreux, Switzerland, Jun. 1-3, 2005.
Chakrabarty et al., "Design Automation for Microfluidics-Based Biochips", ACM Journal on Engineering Technologies in Computing Systems , 1(3), Oct. 2005, 186-223.
Chakrabarty, "Design, Testing, and Applications of Digital Microfluidics-Based Biochips", Proceedings of the 18th International Conf. On VLSI held jointly with 4th International Conf. on Embedded Systems Design (VLSID'05), IEEE, Jan. 3-7, 2005.
Chen et al., "Development of Mesoscale Actuator Device with Micro Interlocking Mechanism", J. Intelligent Material Systems and Structures, vol. 9, No. 4, Jun. 1998, pp. 449-457.
Chen et al., "Mesoscale Actuator Device with Micro Interlocking Mechanism", Proc. IEEE Micro Electro Mechanical Systems Workshop, Heidelberg, Germany, Jan. 1998, pp. 384-389.
Chen et al., "Mesoscale Actuator Device: Micro Interlocking Mechanism to Transfer Macro Load", Sensors and Actuators, vol. 73, Issues 1-2, Mar. 1999, pp. 30-36.
Cotten et al., "Digital Microfluidics: a novel platform for multiplexed detection of lysosomal storage diseases", Abstract # 3747.9. Pediatric Academic Society Conference, 2008.
Delattre, Movie in news on TF1 (at 12'45" Cyril DELATTRE), http://videos.tf1.fr/jt-we/zoom-sur-grenoble-6071525.html, 2009.
Delattre, Movie in talk show "C Dans l'air" (at 24" Cyril Delattre), http://www.france5.fr/c-dans-l-air/sante/bientot-vous-ne-serez-plus-malade-31721, 2009.
Delattre, Movie on Web TV—Cite des sciences (at 3'26" Cyril Delattre), http://www.universcience.tv/video-laboratoire-de-poche-793.html, 2009.
Delattre et al., "Towards an industrial fabrication process for electrowetting chip using standard MEMS Technology", µTAS2008, San Diego; poster presented, Oct. 15, 2008.
Delattre et al., "Towards an industrial fabrication process for electrowetting chip using standard Mems Technology", µTAS2008, San Diego; Abstract in proceedings, Oct. 13-16, 2008, 1696-1698.
Dewey, "Towards a Visual Modeling Approach to Designing Microelectromechanical System Transducers", Journal of Micromechanics and Microengineering, vol. 9, Dec. 1999, 332-340.
Dewey et al., "Visual modeling and design of microelectromechanical system tansducers", Microelectronics Journal, vol. 32, Apr. 2001, 373-381.
Fair et al., "A Micro-Watt Metal-Insulator-Solution-Transport (MIST) Device for Scalable Digital Bio-Microfluidic Systems", IEEE IEDM Technical Digest, 2001, 16.4.1-4.
Fair et al., "Advances in droplet-based bio lab-on-a-chip", BioChips 2003, Boston, 2003.
Fair et al., "Bead-Based and Solution-Based Assays Performed on a Digital Microfluidic Platform", Biomedical Engineering Society (BMES) Fall Meeting, Baltimore, MD, Oct. 1, 2005.

Fair, "Biomedical Applications of Electrowetting Systems", 5th International Electrowetting Workshop, Rochester, NY, May 31, 2006.

Fair et al., "Chemical and Biological Applications of Digital-Microfluidic Devices", IEEE Design & Test of Computers, vol. 24(1), Jan.-Feb. 2007, 10-24.

Fair et al., "Chemical and biological pathogen detection in a digital microfluidic platform", DARPA Workshop on Microfluidic Analyzers for DoD and National Security Applications, Keystone, CO, 2006.

Fair, "Digital microfluidics: is a true lab-on-a-chip possible?", Microfluid Nanofluid, vol. 3, Mar. 8, 2007, 245-281.

Fair, "Droplet-based microfluidic Genome sequencing", NHGRI PI's meeting, Boston, 2005.

Fair et al., "Electrowetting-based On-Chip Sample Processing for Integrated Microfluidics", IEEE Inter. Electron Devices Meeting (IEDM), 2003, 32.5.1-32.5.4.

Fair et al., "Integrated chemical/biochemical sample collection, preconcentration, and analysis on a digital microfluidic lab-on-a-chip platform", Lab-on-a-Chip: Platforms, Devices, and Applications, Conf. 5591, SPIE Optics East, Philadelphia, Oct. 25-28, 2004,.

Fair, "Scaling of Digital Microfluidic Devices for Picoliter Applications", The 6th International Electrowetting Meeting, Aug. 20-22, 2008, p. 14.

Fouillet, "Bio-Protocol Integration in Digital Microfluidic Chips", The 6th International Electrowetting Meeting, Aug. 20-22, 2008, p. 15.

Fouillet et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 5860.

Fouillet et al., "Digital microfluidic design and optimization of classic and new fluidic functions for lab on a chip systems", Microfluid Nanofluid, vol. 4, 2008, 159-165.

Hua et al., "Rapid Detection of Methicillin-Resistant Staphylococcus Aureus (MRSA) Using Digital Microfluidics", 12th Intl Conference on Miniaturized Systems for Chemistry and Life Sciences, Proc. µTAS, Oct. 12-16, 2008.

Jary et al., "SmartDrop, Microfluidics for Biology", Forum 4i 2009, Grenoble, France; Flyer distributed at booth, May 14, 2009.

Jun et al., "Valveless Pumping using Traversing Vapor Bubbles in Microchannels", J. Applied Physics, vol. 83, No. 11, Jun. 1998, pp. 5658-5664.

Kim et al., "MEMS Devices Based on the Use of Surface Tension", Proc. Int. Semiconductor Device Research Symposium (ISDRS'99), Charlottesville, VA, Dec. 1999, pp. 481-484.

Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.

Kim et al., "Micromachines Driven by Surface Tension", AIAA 99/3800, 30th AIAA Fluid Dynamics Conference, Norfolk, VA, (Invited lecture), Jun. 1999, pp. 1-6.

Kleinert et al., "Electric Field-Assisted Convective Assembly of Large-Domain Colloidal Crystals", The 82nd Colloid & Surface Science Symposium, ACS Division of Colloid & Surface Science, North Carolina State University, Raleigh, NC. www.colloids2008.org., Jun. 15-18, 2008.

Lee et al., "Microactuation by Continuous Electrowetting Phenomenon and Silicon Deep Rie Process", Proc. Mems (DSC—vol. 66) ASME Int. Mechanical Engineering Congress and Exposition, Anaheim, CA, Nov. 1998, 475-480.

Lee et al., "Liquid Micromotor Driven by Continuous Electrowetting", Proc. IEEE Micro Electro Mechanical Systems Workshop, Heidelberg, Germany, Jan. 1998, pp. 538-543.

Lee et al., "Theory and Modeling of Continuous Electrowetting Microactuation", Proc. Mems (MEMS—vol. 1), ASME Int. Mechanical Engineering Congress and Exposition, Nashville, TN, Nov. 1999, pp. 397-403.

Marchand et al., "Organic Synthesis in Soft Wall-Free Microreactors: Real-Time Monitoring of Fluorogenic Reactions", Analytical Chemistry, vol. 80, Jul. 2, 2008, 6051-6055.

Millington et al., "Digital Microfluidics: a novel platform for multiplexed detection of LSDs with potential for newborn screening", Association of Public Health Laboratories Annual Conference, San Antonio, TX, Nov. 4, 2008.

Millington et al., "Digital Microfluidics: A Novel Platform for Multiplexing Assays Used in Newborn Screening", Proceedings of the 7th International And Latin American Congress. ORAL PRESENTATIONS. Rev Invest Clin; vol. 61 (Supl. 1), 2009, 21-33.

Paik et al., "A digital-microfluidic approach to chip cooling", IEEE Design & Test of Computers, vol. 25, Jul. 2008, 372-381.

Paik et al., "Adaptive Cooling of Integrated Circuits Using Digital Microfluidics", IEEE Transactions on VLSI, vol. 16, No. 4, 2008, 432-443.

Paik et al., "Adaptive Cooling of Integrated Circuits Using Digital Microfluidics", accepted for publication in IEEE Transactions on VLSI Systems, 2007, and Artech House, Norwood, MA, 2007.

Paik, "Adaptive Hot-Spot Cooling of Integrated Circuits Using Digital Microfluidics", Dissertation, Dept. of Electrical and Computer Engineering, Duke University, Apr. 25, 2006, 1-188.

Paik et al., "Adaptive hot-spot cooling of integrated circuits using digital microfluidics", Proceedings Asme International Mechanical Engineering Congress and Exposition, Orlando, Florida, USA. IMECE2005-81081, Nov. 5-11, 2005, 1-6.

Paik et al., "Coplanar Digital Microfluidics Using Standard Printed Circuit Board Processes", 9th International Conference on Miniaturized Systems for Chemistry and Life Sciences (MicroTAS), Boston, MA; POSTER, 2005.

Paik et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.

Paik et al., "Droplet-Based Hot Spot Cooling Using Topless Digital Microfluidics on a Printed Circuit Board", Int'l Workshops on Thermal Investigations of ICs and Systems (THERMINIC), 2005, 278-83.

Paik et al., "Electrowetting-based droplet mixers for microfluidic systems", Lab on a Chip (LOC), vol. 3. (more mixing videos available, along with the article, at LOC's website), 2003, 28-33.

Paik et al., "Programmable Flow-Through Real Time PCR Using Digital Microfluidics", 11th International Conference on Miniaturized Systems for Chemistry and Life Sciences, Paris, France, Oct. 7-11, 2007, 1559-1561.

Paik et al., "Programmable flow-through real-time PCR using digital microfluidics", Proc. Micro Total Analysis Systems (µTAS), Handout, 2007.

Paik et al., "Programmable flow-through real-time PCR using digital microfluidics", Proc. Micro Total Analysis Systems (µTAS), Poster, 2007.

Paik et al., "Rapid Droplet Mixers for Digital Microfluidic Systems", Masters Thesis, Duke Graduate School., 2002, 1-82.

Paik et al., "Rapid droplet mixers for digital microfluidic systems", Lab on a Chip, vol. 3. (More mixing videos available, along with the article, at LOC's website.), 2003, 253-259.

Paik et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.

Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.

Pamula et al., "A droplet-based lab-on-a-chip for colorimetric detection of nitroaromatic explosives", Proceedings of Micro Electro Mechanical Systems, 2005, 722-725.

Pamula et al., "Cooling of integrated circuits using droplet-based microfluidics", Proc. ACM Great Lakes Symposium on VLSI, Apr. 2003, 84-87.

Pamula et al., "Digital microfluidic lab-on-a-chip for protein crystallization", 5th Protein Structure Initiative "Bottlenecks" Workshop, NIH, Bethesda, MD, Apr. 13-14, 2006, I-16.

Pamula et al., "Digital Microfluidics Platform for Lab-on-a-chip applications", Duke University Annual Post Doctoral Research Day, 2002.

Pamula et al., "Microfluidic electrowetting-based droplet mixing", IEEE, 2002, 8-10.

Pollack et al., "Electrowetting-based actuation of liquid droplets for microfluidic applications", Appl. Phys. Letters, vol. 77, No. 11, Sep. 11, 2000, 1725-1726.

Pollack, "Electrowetting-based Microactuation of Droplets for Digital Microfluidics", PhD Thesis, Department of Electrical and Computer Engineering, Duke University, 2001.

Pollack et al., "Electrowetting-Based Microfluidics for High-Throughput Screening", smallTalk 2001 Conference Program Abstract, San Diego, Aug. 27-31, 2001, 149.

Pollack et al., "Investigation of electrowetting-based microfluidics for real-time PCR applications", Proc. 7th Int'l Conference on Micro Total Analysis Systems (mTAS), Squaw Valley, CA, Oct. 5-9, 2003, 619-622.

Pollack, "Lab-on-a-chip platform based digital microfluidics", The 6th International Electrowetting Meeting, Aug. 20-22, 2008, 16.

Ren et al., "Automated electrowetting-based droplet dispensing with good reproducibility", Proc. Micro Total Analysis Systems (mTAS), 7th Int. Conf.on Miniaturized Chem and Biochem Analysis Systems, Squaw Valley, CA, Oct. 5-9, 2003, 993-996.

Ren et al., "Automated on-chip droplet dispensing with volume control by electro-wetting actuation and capacitance metering", Sensors and Actuators B: Chemical, vol. 98, Mar. 2004, 319-327.

Ren et al., "Design and testing of an interpolating mixing architecture for electrowetting-based droplet-on-chip chemical dilution", Transducers, 12th International Conference on Solid-State Sensors, Actuators and Microsystems, 2003, 619-622.

Ren et al., "Dynamics of electro-wetting droplet transport", Sensors and Actuators B (Chemical), vol. B87, No. 1, Nov. 15, 2002, 201-206.

Ren et al., "Micro/Nano Liter Droplet Formation and Dispensing by Capacitance Metering and Electrowetting Actuation", IEEE-NANO, 2002, 369-372.

Rival et al., "Towards Single Cells Gene Expression on EWOD Lab on Chip", ESONN 2008, Grenoble, France; Poster presented, Aug. 26, 2008.

Rival et al., "Towards single cells gene expression on EWOD lab on chip", ESONN, Grenoble, France, abstract in proceedings, Aug. 2008.

Rouse et al., "Digital microfluidics: a novel platform for multiplexing assays used in newborn screening", Poster 47, 41st AACC's Annual Oak Ridge Conference Abstracts, Clinical Chemistry, vol. 55, 2009, 1891.

Sherman et al., "Flow Control by Using High-Aspect-Ratio, In-Plane Microactuators", Sensors and Actuators, vol. 73, 1999, pp. 169-175.

Sherman et al., "In-Plane Microactuator for Fluid Control Application", Proc. IEEE Micro Electro Mechanical Systems Workshop, Heidelberg, Germany, Jan. 1998, pp. 454-459.

Sista et al., "96-Immunoassay Digital Microfluidic Multiwell Plate", Proc. µTAS, Oct. 12-16, 2008.

Sista, "Development of a Digital Microfluidic Lab-on-a-Chip for Automated Immunoassays with Magnetically Responsive Beads", PhD Thesis, Department of Chemical Engineering, Florida State University, 2007.

Sista et al., "Development of a digital microfluidic platform for point of care testing", Lab on a chip, vol. 8, Dec. 2008, First published as an Advance Article on the web, Nov. 5, 2008, 2091-2104.

Sista et al., "Heterogeneous immunoassays using magnetic beads on a digital microfluidic platform", Lab on a Chip, vol. 8, Dec. 2008, First published as an Advance Article on the web, Oct. 14, 2008, 2188-2196.

Sista et al., "Spatial multiplexing of immunoassays for small-volume samples", 10th PI Meeting IMAT, Bethesda, 2009.

Srinivasan et al., "3-D imaging of moving droplets for microfluidics using optical coherence tomography", Proc. 7th International Conference on Micro Total Analysis Systems (mTAS), Squaw Valley, CA, Oct. 5-9, 2003, 1303-1306.

Srinivasan et al., "A digital microfluidic biosensor for multianalyte detection", Proc. IEEE 16th Annual Intl Conf. on Micro Electro Mechanical Systems Conference, 2003, 327-330.

Srinivasan, "A Digital Microfluidic Lab-on-a-Chip for Clinical Diagnostic Applications", Ph.D. thesis, Dept of Electrical and Computer Engineering, Duke University, 2005.

Srinivasan et al., "An integrated digital microfluidic lab-on-a-chip for clinical diagnostics on human physiological fluids", Lab on a Chip, vol. 4, 2004, 310-315.

Srinivasan et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct. 5-9, 2003, 1287-1290.

Srinivasan et al., "Digital Microfluidic Lab-on-a-Chip for Protein Crystallization", The 82nd ACS Colloid and Surface Science Symposium, 2008.

Srinivasan et al., "Digital Microfluidics: a novel platform for multiplexed detection of lysosomal storage diseases for newborn screening", AACC Oak Ridge Conference Abstracts, Clinical Chemistry, vol. 54, 2008, 1934.

Srinivasan et al., "Droplet-based microfluidic lab-on-a-chip for glucose detection", Analytica Chimica Acta, vol. 507, No. 1, 2004, 145-150.

Srinivasan et al., "Low cost digital microfluidic platform for protein crystallization", Enabling Technologies for Structural Biology, NIGMS Workshop, Bethesda, MD., Mar. 4-6, 2009, J-23.

Srinivasan et al., "Protein Stamping for Maldi Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.

Srinivasan et al., "Scalable Macromodels for Microelectromechanical Systems", Technical Proc. 2001 Int. Conf. on Modeling and Simulation of Microsystems, 2001, 7275.

Su et al., "Yield Enhancement of Digital Microfluidics-Based Biochips Using Space Redundancy and Local Reconfiguration", Proc. Design, Automation and Test in Europe (DATE) Conf., IEEE, 2005, 1196-1201.

Sudarsan et al., "Printed circuit technology for fabrication of plastic based microfluidic devices", Analytical Chemistry vol. 76, No. 11, Jun. 1, 2004, Previously published online, May 2004, 3229-3235.

Thwar et al., "DNA sequencing using digital microfluidics", Poster 42, 41st AACC's Annual Oak Ridge Conference Abstracts, Clinical Chemistry vol. 55, 2009, 1891.

Wang et al., "Droplet-based micro oscillating-flow PCR chip", J. Micromechanics and Microengineering, vol. 15, 2005, 1369-1377.

Wang et al., "Efficient in-droplet separation of magnetic particles for digital microfluidics", Journal of Micromechanics and Microengineering, vol. 17, 2007, 2148-2156.

Xu et al., "A Cross-Referencing-Based Droplet Manipulation Method for High-Throughput and Pin-Constrained Digital Microfluidic Arrays", Proceedings of conference on Design, Automation and Test in Europe, Apr. 2007.

Xu et al., "Automated Design of Pin-Constrained Digital Microfluidic Biochips Under Droplet-Interference Constraints", ACM Journal on Emerging Technologies is Computing Systems, vol. 3(3), 2007, 14:1-14:23.

Xu et al., "Automated solution preparation on a digital microfluidic lab-on-chip", PSI Bottlenecks Workshop, 2008.

Xu et al., "Automated, Accurate and Inexpensive Solution-Preparation on a Digital Microfluidic Biochip", Proc. IEEE Biomedical Circuits and Systems Conference (BioCAS), 2008, 301-304.

Xu et al., "Defect-Aware Synthesis of Droplet-Based Microfluidic Biochips", IEEE, 20th International Conference on VLSI Design, 2007.

Xu et al., "Design and Optimization of a Digital Microfluidic Biochip for Protein Crystallization", Proc. IEEE/ACM International Conference on Computer-Aided Design (ICCAD), Nov. 2008, 297-301.

Xu et al., "Digital Microfluidic Biochip Design for Protein Crystallization", IEEE-NIH Life Science Systems and Applications Workshop, Lisa, Bethesda, MD, Nov. 8-9, 2007, 140-143.

Xu et al., "Droplet-Trace-Based Array Partitioning and a Pin Assignment Algorithm for the Automated Design of Digital Microfluidic Biochips", CODES, 2006, 112-117.

Xu et al., "Integrated Droplet Routing in the Synthesis of Microfluidic Biochips", IEEE, 2007, 948-953.

Xu et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.

Xu et al., "Parallel Scan-Like Testing and Fault Diagnosis Techniques for Digital Microfluidic Biochips", Proceedings of the 12th IEEE European Test Symposium (ETS), Freiburg, Germany, May 20-24, 2007, 63-68.

Yao et al., "Spot Cooling Using Thermoelectric Microcooler", Proc. 18th Int. Thermoelectric Conf, Baltimore, VA, pp. 256-259, Aug. 1999.

Yi et al., "Channel-to-droplet extractions for on-chip sample preparation", Solid-State Sensor, Actuators and Microsystems Workshop (Hilton Head '06), Hilton Head Island, SC, Jun. 2006, 128-131.

Yi et al., "Characterization of electrowetting actuation on addressable single-side coplanar electrodes", Journal of Micromechanics and Microengineering, vol. 16, Oct. 2006, 2053-2059.

Yi et al., "EWOD Actuation with Electrode-Free Cover Plate", Digest of Tech. papers, 13th International Conference on Solid-State Sensors, Actuators and Microsystems (Transducers '05), Seoul, Korea, Jun. 5-9, 2005, 89-92.

Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.

Yi, "Soft Printing of Biological Liquids for Micro-arrays: Concept, Principle, Fabrication, and Demonstration", Ph.D. dissertation, UCLA, 2004.

Yi et al., "Soft Printing of Droplets Digitized by Electrowetting", Transducers 12th Intl Conf. on Solid State Sensors, Actuators and Microsystems, Boston, Jun. 8-12, 2003, 1804-1807.

Yi et al., "Soft Printing of Droplets Pre-Metered by Electrowetting", Sensors and Actuators A: Physical, vol. 114, Jan. 2004, 347-354.

Zeng et al., "Actuation and Control of Droplets by Using Electrowetting-on-Dielectric", Chin. Phys. Lett., vol. 21(9), 2004, 1851-1854.

Zhao et al., "Droplet Manipulation and Microparticle Sampling on Perforated Microfilter Membranes", J. Micromech. Microeng., vol. 18, 2008, 1-11.

Zhao et al., "In-droplet particle separation by travelling wave dielectrophoresis (twDEP) and EWOD", Solid-State Sensor, Actuators and Microsystems Workshop (Hilton Head '06), Hilton Head Island, SC, Jun. 2006, 181-184.

Zhao et al., "Micro air bubble manipulation by electrowetting on dielectric (EWOD): transporting, splitting, merging and eliminating of bubbles", Lab on a chip, vol. 7, 2007, First published as an Advance Article on the web, Dec. 4, 2006, 273-280.

Zhao et al., "Microparticle Concentration and Separation byTraveling-Wave Dielectrophoresis (twDEP) for Digital Microfluidics", J. Microelectromechanical Systems, vol. 16, No. 6, Dec. 2007, 1472-1481.

PCT International Search Report and Written Opinion for PCT/US2009/044305 dated Apr. 1, 2010.

* cited by examiner

*Primary Examiner* — Christopher A Hixson
(74) *Attorney, Agent, or Firm* — William A. Barrett; Ward & Smith, P.A.

(57) ABSTRACT

The invention provides droplet actuators and droplet actuator techniques. Among other things, the droplet actuators and methods are useful for manipulating beads on a droplet actuator, such as conducting droplet operations using bead-containing droplets on a droplet actuator. For example, beads may be manipulated on a droplet actuator in the context of executing a sample preparation protocol and/or an assay protocol. An output of the methods of the invention may be beads prepared for execution of an assay protocol. Another output of the methods of the invention may be results of an assay protocol executed using beads. Among the methods described herein are methods of concentrating beads in droplets, methods of washing beads, methods of suspending beads, methods of separating beads, methods of localizing beads within a droplet, methods of forming emulsions in which droplets include beads, methods of loading beads into a droplet operations gap of a droplet actuator, methods of organizing beads in a monolayer, and methods of capturing, trapping or restraining beads.

42 Claims, 25 Drawing Sheets

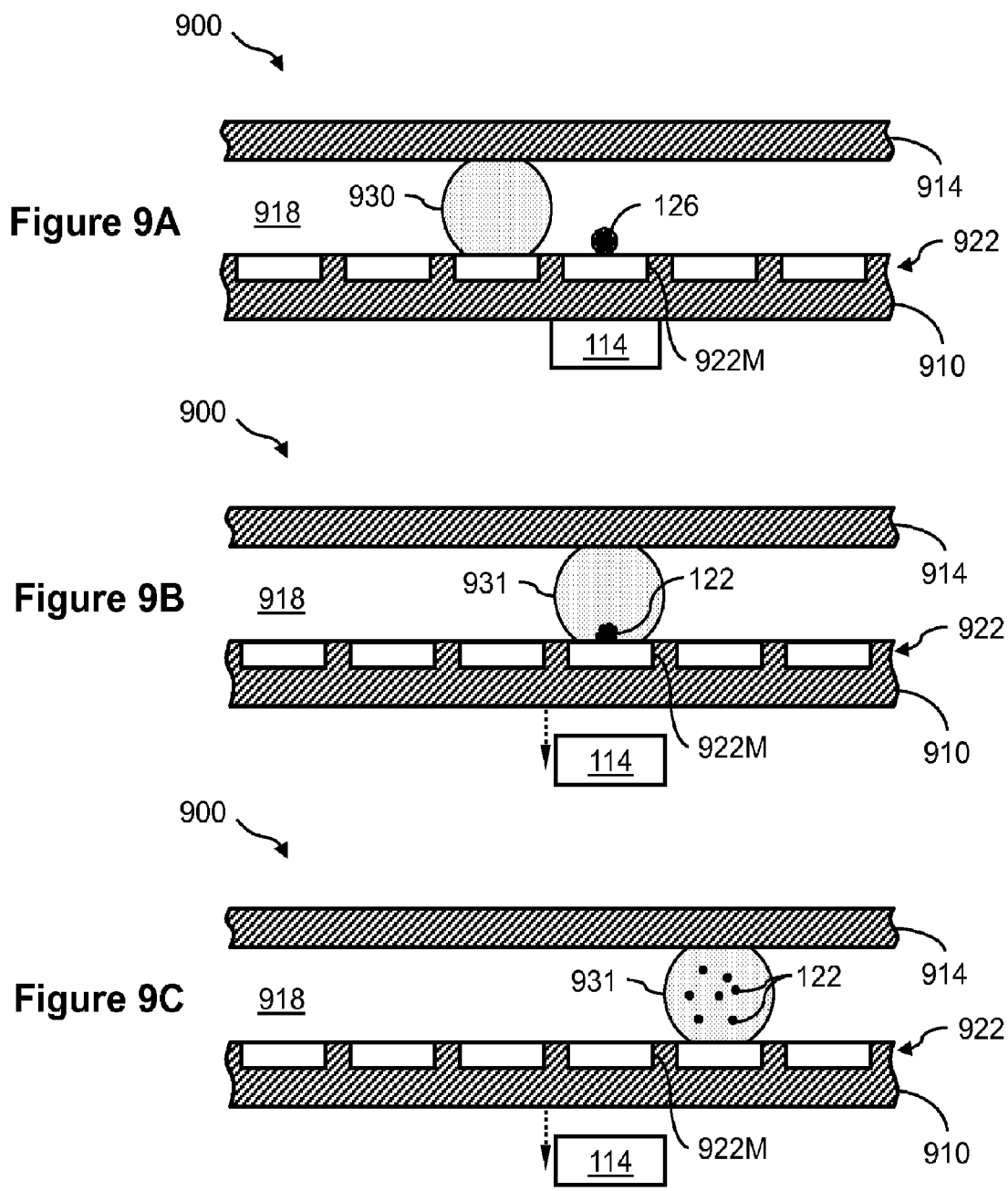

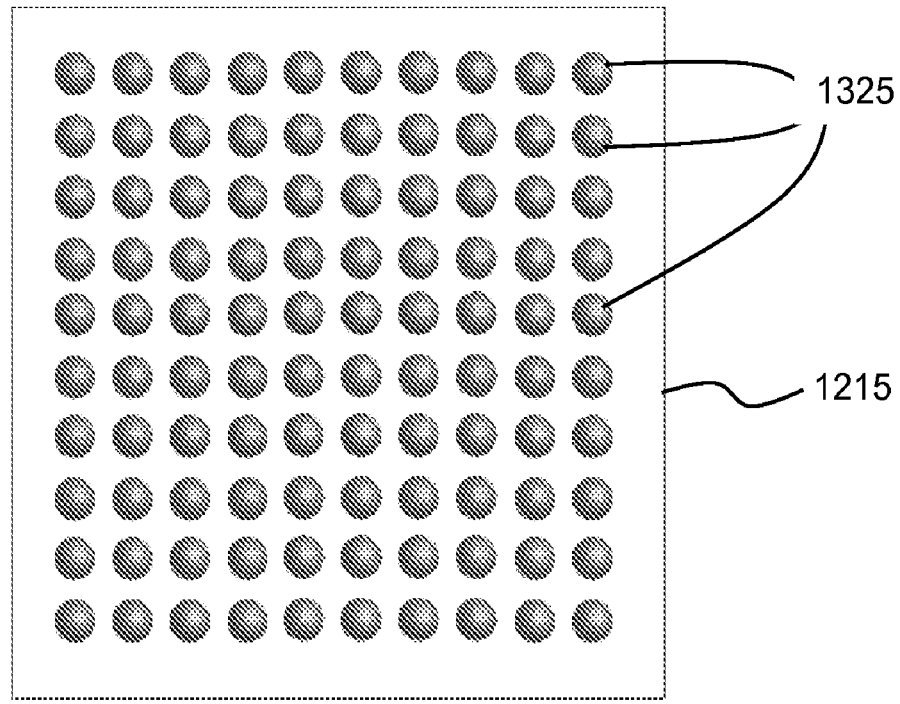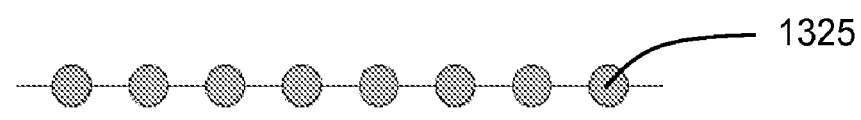
Figure 14

METHOD OF REDUCING LIQUID VOLUME SURROUNDING BEADS

1 RELATED APPLICATIONS

This application is a 371 of International Application No. PCT/US2009/044305, entitled "Droplet Actuator Devices and Methods for Manipulating Beads" filed on May 18, 2009, the application of which claims priority to the following U.S. patent application Nos. 61/075,250, entitled "Manipulating Beads in a Droplet Actuator," filed on Jun. 24, 2008; 61/053,693, entitled "Bead handling on a droplet actuator," filed on May 16, 2008; 61/082,314, entitled "Bead Handling on a Droplet Actuator," filed on Jul. 21, 2008; 61/085,773, entitled "Droplet Actuator Devices and Methods for Handling Beads," filed on Aug. 1, 2008; 61/160,607, entitled "Droplet Actuator Devices and Methods for Manipulating Beads," filed on Mar. 16, 2009; the entire disclosures of each of these applications is incorporated herein by reference.

This patent application is also a continuation in part of U.S. patent application Ser. No. 11/639,663, entitled "Droplet-Based Affinity Assays," filed Dec. 15, 2006, (issued on Jul. 23, 2013 as U.S. Pat. No. 8,492,168), the application of which claims priority to and incorporates by reference related provisional U.S. Patent Application Nos. 60/745,058, entitled "Filler Fluids for Droplet-Based Microfluidics" filed on Apr. 18, 2006; 60/745,039, entitled "Apparatus and Methods for Droplet-Based Blood Chemistry," filed on Apr. 18, 2006; 60/745,043, entitled "Apparatus and Methods for Droplet-Based PCR," filed on Apr. 18, 2006; 60/745,059, entitled "Apparatus and Methods for Droplet-Based Immunoassay," filed on Apr. 18, 2006; 60/745,914, entitled "Apparatus and Method for Manipulating Droplets with a Predetermined Number of Cells" filed on Apr. 28, 2006; 60/745,950, entitled "Apparatus and Methods of Sample Preparation for a Droplet Microactuator," filed on Apr. 28, 2006; 60/746,797 entitled "Portable Analyzer Using Droplet-Based Microfluidics," filed on May 9, 2006; 60/746,801, entitled "Apparatus and Methods for Droplet-Based Immuno-PCR," filed on May 9, 2006; 60/806,412, entitled "Systems and Methods for Droplet Microactuator Operations," filed on Jun. 30, 2006; and 60/807,104, entitled "Method and Apparatus for Droplet-Based Nucleic Acid Amplification," filed on Jul. 12, 2006.

2 BACKGROUND

Droplet actuators are used to conduct a wide variety of droplet operations. A droplet actuator typically includes one or more substrates forming a droplet operations surface or droplet operations gap. The gap between the substrates is typically filled with a filler fluid that is immiscible with the liquid that is to be subjected to droplet operations. Droplet operations are controlled by electrodes associated with one or both of the substrates. There is a need for modified droplet actuators and droplet actuator techniques for manipulating beads on a droplet actuator.

3 SUMMARY OF THE INVENTION

The invention provides a method of reducing a liquid volume surrounding one or more magnetically responsive beads. The method may include providing a droplet including one or more magnetically responsive beads. The method may include exposing the magnetically responsive beads in the droplet to a first region of a magnetic field. The method may include separating the droplet from the first region of the magnetic field, the magnetically responsive beads remaining in the magnetic field. The droplet may include a wash buffer. The droplet may include one or more target substances for which at least a subset of the one or more beads has affinity. The magnetically responsive beads may be surrounded by liquid from the droplet.

The magnetically responsive beads may be separated from the droplet while exposing the magnetically responsive beads in the droplet to a first region of a magnetic field and/or while the droplet is being separated from the first region of the magnetic field. Separating the droplet from the first region of the magnetic field may include magnetically attracting beads from a droplet positioned at least partially in a droplet operations gap of a droplet actuator through an opening in a substrate of the droplet actuator to a locus which may be exterior to the droplet operations gap. The magnetically responsive beads may be snapped out of or otherwise removed from the droplet when the droplet is in the first region of the magnetic field. During the separation, the droplet may, in some embodiments, be restrained from following the magnetically responsive beads by a surface property of an underlying substrate. The surface property of the underlying substrate may cause the droplet to remain in a substantially stationary position during the separation; and/or may cause the droplet to move closer to the region of the magnetic field during the separation; and/or may cause the droplet to move further from the region of the magnetic field during the separation. The surface property of the underlying substrate may be mediated by an electrode, such as an electrode underlying the substrate (e.g., an electrowetting electrode and/or a dielectrophoresis electrode arrangement). The droplet may be surrounded by a liquid filler fluid that may be substantially immiscible with the droplet.

The magnetically responsive beads may remain in the first region of the magnetic field in some cases. In other cases, the magnetically responsive beads may be caused by the magnetic field to relocate from the first region of the magnetic field to a second region of the magnetic field. Exposing the magnetically responsive beads in the droplet to a first region of a magnetic field may include transporting the droplet into the first region of the magnetic field and/or transporting the first region of the magnetic field into proximity with the magnetically responsive beads. Separating the droplet from the first region of the magnetic field may include transporting the droplet away from the first region of the magnetic field and/or moving the first region of the magnetic field away from the droplet.

The method may be used for concentrating a target substance on the magnetic bead by contacting the magnetic bead with a sample droplet. The sample droplet may be separated from the first region of the magnetic field, the magnetically responsive beads remaining in the magnetic field. The method may include washing the magnetic bead by contacting the magnetic bead with a wash droplet. The method may include separating the wash droplet from the first region of the magnetic field, the magnetically responsive beads remaining in the magnetic field.

Providing a droplet including magnetically responsive beads may include providing the droplet in a droplet operations gap of a droplet actuator, wherein the droplet is subject to one or more droplet operations. Exposing the magnetically responsive beads in the droplet to a first region of a magnetic field may include transporting the droplet using electrode-mediated droplet operations into the first region of the magnetic field and/or transporting the first region of the magnetic field into proximity with the magnetically responsive beads. Separating the droplet from the first region of the magnetic field may include transporting the droplet using electrode-mediated droplet operations away from the first region of the magnetic field and/or transporting the first region of the magnetic field away from the magnetically responsive beads. The one or more droplet operations may be mediated by one or more electrodes. Following separating the droplet from the first region of the magnetic field, the droplet may be subjected to one or more additional assay or sample preparation steps and/or may be presented to a detector or detection window for detection of a property of and/or signal from the droplet.

The magnetically responsive beads remaining in the magnetic field may be positioned in a droplet atop an electrowetting electrode. In some cases, the footprint of the droplet is smaller than the footprint of the electrowetting electrode. The magnetically responsive beads may be subjected to an assay protocol. In this and other methods described herein, an output of an assay may include human-readable results of an assay protocol. Further, in this and other methods described herein, execution of one or more steps of the method may be controlled by a computer.

The invention provides a system programmed to execute any of the methods of the invention. The system may include a computer or computer processor or controller coupled to one or more droplet actuators and programmed to execute one or more steps of any of the methods of the invention.

The invention provides a method of merging a first droplet with a second droplet. The method may include providing a droplet actuator substrate may include electrowetting electrodes arranged to mediate one or more droplet operations, each electrowetting electrode having a footprint. The method may include providing atop an electrode a first droplet having a footprint which may be smaller than the footprint of the electrode. The method may include transporting a second droplet along the electrowetting electrodes into contact with the first droplet. The first droplet may include beads, which may in some instances be magnetically responsive. The first droplet may be provided by magnetically attracting a component of a droplet onto the electrode. The first droplet may be transported into position atop the electrode by a magnetic field acting on the magnetically responsive beads. The first droplet may be broken off of another droplet by a magnetic field acting on the magnetically responsive beads. In one embodiment, the first droplet may be formed by providing a third droplet on the electrode and merging the third droplet with a fourth droplet may include magnetically responsive beads to yield the first droplet. In another embodiment, the first droplet may be formed by merging a third droplet with a fourth droplet including magnetically responsive beads to yield the first droplet, and magnetically attracting the first droplet onto the electrode. In various embodiments, a droplet may be retained in position by a magnetic field acting on magnetically responsive beads within the droplet.

The invention provides a method of conducting one or more steps of an assay. The method may include arraying on a substrate a sample liquid, and one or more reagent liquids. The method may include using a magnetic field, gravity, and/or centrifugal force to move beads having affinity for a target substance in the sample liquid into and/or through the sample liquid and the reagent liquids to conduct the assay. In some cases, the method includes using gravity, and/or centrifugal force, and/or a magnetic field to move beads having affinity for a target substance in the liquid into and/or through the sample liquid and the reagent liquids to conduct one or more steps of a sample preparation protocol and/or an assay. The arraying may, in some cases, be mediated at least in part by one or more electrodes associated with the substrate. Where a magnetic field is used, it may be moved along a path of liquid operations electrodes and/or along a path intersecting a path of liquid operations electrodes. The sample liquid may be arrayed atop and maintained in position by an electrode underlying the substrate. The one or more reagent liquids may be arrayed atop and maintained in position by an electrode underlying the substrate. The sample liquid and one or more reagent liquids may be arrayed such that movement of the magnetic field along a straight line will cause the one or more beads to move through the sample liquid and one or more reagent liquids.

The method may include repeating movements of the magnetic field along a path, and the sample liquid and/or one or more reagent liquids is moved into the path between such repeating movements of the magnetic field along a path. The repeating movements of the magnetic field along a path may include repeatedly transporting a droplet around a loop path and/or may include back and forth movements along a non-looping path.

In the various assays described herein, the one or more reagents may include any reagents suitable for conducting any assay. Examples include reagents for conducting an immunoassay, an enzymatic assay, a nucleic acid assay, etc.

Further, in the various assays described herein, the method may include using a magnetic field to move magnetically responsive beads into a detection liquid may include reagents for producing a signal indicative of the presence and/or quantity of the target substance. The detection liquid may be in contact with or in sensing proximity to a sensor when the magnetically responsive beads may be moved into the detection liquid. The detection liquid may be transported into contact, or sensing proximity, with a sensor after the magnetically responsive beads may be moved into the detection liquid. In any of the techniques described herein, the arraying, providing or otherwise disposing a droplet or liquid on a substrate may include arraying in one or more channel and/or on an open substrate and/or in a droplet operations gap.

The invention provides a method of removing one or more beads from a position in which the one or more beads is restrained by a force. The method may include providing a first droplet including the one or more beads. The method may further include exposing the one or more beads to a force which acts on the one or more beads in a first direction. The method may include transporting the droplet in a second direction, causing the droplet to move the beads in the second direction, against the force which acts on the one or more beads in the first direction. In some cases, the droplet has a interfacial tension which is sufficiently high to prevent the first force from causing the one or more beads to leave the droplet during the transporting step. The first force may, in some instances, include a magnetic force and at least a subset of the one or more beads may include magnetically responsive beads. The magnetic force may include a magnetic field emitted by a magnetic field emitting device (e.g., a permanent magnet or an electromagnet) positioned in proximity to the droplet. In certain embodiments, the first force may include a centrifugal force and/or a gravitational force. In certain embodiments, the second force may include an electrowetting force, a dielectrophoretic force, and/or a frictional force. The second direction may be partially or completely opposite, opposed to, or against the first direction. The second force may be in any direction which partially or completely acts against the first force.

In certain embodiments, the method may include forming the first droplet by combining a second droplet may include the one or more beads and having a interfacial tension which may be not sufficiently high to prevent the first force from causing the one or more beads to leave the second droplet, and a third droplet having a interfacial tension which may be sufficiently high to raise the interfacial tension of the second droplet to a level which may be sufficiently high to prevent the first force from causing the one or more beads to leave the combined first droplet.

The invention provides a method of positioning a droplet including magnetically responsive beads atop an electrode in a droplet operations gap of a droplet actuator. The method may include using a magnetic field to attract the droplet with the beads to a position atop an electrode. The droplet may have a droplet footprint which is substantially smaller than the electrode footprint. For example, in certain embodiments, the droplet footprint area may be less than about 75%, or less than about 50%, or less than about 25% of the electrode footprint area. The droplet may be substantially surrounded in the droplet operations gap by a liquid filler fluid that may be immiscible with the droplet. The technique may be useful for retaining droplets in place during shipment. Magnets may, in some cases, be removed prior to use in order to free the droplets for operation. Thus, for example, the invention may include a shipping packaging component including magnets coupled to a droplet actuator including one or more magnetic bead-containing droplets retained in place by magnets on the packaging component. The packaging component and the droplet actuator may be separated to free the droplets prior to execution of a protocol on the droplet actuator.

The invention also includes a droplet actuator with a substrate, one or more electrodes associated with the substrate and configured to effect one or more droplet operations on a surface of the substrate, one or more bead binding sites on the droplet operations surface atop one or more of the electrodes. The bead binding sites may include one or more beads bound thereto. The bead binding sites may include an array of multiple bead binding sites on the droplet operations surface atop a droplet operations electrode. The bead binding sites on the droplet operations surface may include one or more recessed areas. A droplet may be positioned atop the bead binding sites. The droplet may include one or more beads having affinity for the bead binding sites. One or more of the bead binding sites may include a substance that has an affinity for one or more of the beads. In some cases, a droplet actuator may include two or more electrodes, each associated with bead binding sites. The bead binding sites of each electrode having affinity for a different bead-type, e.g., the bead type may include a different bead binding modality as well as affinity for a different target substance. A magnetic field emitting device may underly one or more of the bead binding sites.

The invention provides a method of arraying beads on a substrate. The method may, for example, include providing a droplet actuator with a substrate, one or more electrodes associated with the substrate and configured to effect one or more droplet operations on a surface of the substrate, and one or more bead binding sites on the droplet operations surface atop one or more of the electrodes. The method may also include providing on the substrate a droplet may include beads, and transporting the droplet onto the one or more bead binding sites causing one or more beads to bind to one or more bead binding sites. The one or more bead binding sites may include an array of bead binding sites on the droplet operations surface atop a droplet operations electrode. Causing one or more beads to bind to one or more bead binding sites may include causing the multiple beads to be arrayed in a monolayer the droplet operations surface atop a droplet operations electrode. The one or more bead binding sites on the droplet operations surface may include one or more recessed areas. Causing one or more beads to bind to one or more bead binding sites may include causing the one or more beads to settle in and/or bind to the recessed areas. One or more of the bead binding sites may include a substance that has an affinity for one or more of the beads. Causing one or more beads to bind to one or more bead binding sites may include causing the one or more beads to bind to the substance. In some cases, a subset of the beads binds to a first set of one or more bead binding sites and another subset of the beads does not bind to the first set of one or more bead binding sites. In some cases, a first subset of the beads having affinity for a first target substance binds to a first set of one or more bead binding sites and a second subset of the beads having affinity for a second target substance does not bind to the first set of one or more bead binding sites. In some cases, the second subset of the beads having affinity for a second target substance binds to a second set of one or more bead binding sites. This may involve transporting the droplet with the second subset of the beads to a second set of one or more bead binding sites having affinity for the subset of the beads that does not bind to the first set of one or more bead binding sites. In some cases, the second set of one or more bead binding sites may be atop a second electrode, and here as in all other instances of droplet transport described herein, the transport may be electrode mediated, such as electrowetting mediated and/or dielectrophoresis mediated. Causing one or more beads to bind to one or more bead binding sites may include magnetically attracting the one or more beads to the one or more bead binding sites, and/or may include agitating the droplet to cause the beads to spread into multiple bead binding sites.

The invention also provides a droplet actuator with one or more substrates arranged to form a droplet operations gap, one or more electrodes arranged to conduct one or more droplet operations in the droplet operations gap, and a reservoir in fluid communication with the droplet operations gap having two or more liquid paths extending from the reservoir into the droplet operations gap. In some cases, each liquid path enters the droplet operations gap at an opening locus which may be substantially aligned with an electrode. In some cases, the reservoir is mounted directly on or formed in or on a droplet actuator substrate. The electrode onto which the liquid flows from the reservoir may be across the droplet operations gap from the opening locus.

One or more bead binding sites may be included on a surface of the droplet operations gap. One or more of the bead binding sites may be at a bead binding locus of the droplet operations gap which is atop an electrode. The bead binding locus may be aligned with the opening locus. The bead binding locus may be across the droplet operations gap from the opening locus. A magnetic field producing device may be arranged to attract one or more beads from the opening locus to a surface locus which may be atop an electrode across the droplet operations gap from the opening locus. The reservoir may include a liquid therein, such as a sample or reagent liquid. For example, the sample may include one or more nucleic acid targets for amplification, and multiple sub-samples may be loaded through the fluid paths in order to conduct PCR, such as digital PCR and/or end-point PCR. The liquid may flow through one or more of the openings into the droplet operations gap. In some cases liquid in the reservoir flows through two or more (e.g., 2, 3, 4, 5, 6, 7, 8, 9, 10, 15, 20, 25, 50, 75, 100 or more) of the openings into the droplet operations gap. The liquid in the reservoir that flows into the droplet operations gap may be attracted otherwise facilitated in its entry into the droplet operations gap by an activated electrode associated with a region of the substrate underlying the opening locus. The liquid may include magnetically responsive beads. The magnetically responsive beads may be attracted by a magnetic field to an edge of the liquid which may be in the droplet operations gap. The magnetically responsive beads may be arranged in a monolayer at an edge of the liquid which may be in the droplet operations gap. The magnetically responsive beads may be bound to one or more bead binding sites on a surface of the droplet operations gap.

The invention provides a method of distributing a liquid in a droplet actuator. The method may include may make use of a droplet actuator with one or more substrates arranged to form a droplet operations gap, one or more electrodes arranged to conduct one or more droplet operations in the droplet operations gap, and a reservoir in fluid communication with the droplet operations gap having two or more liquid paths extending from the reservoir into the droplet operations gap. The method may include providing a liquid in the reservoir, and flowing liquid from the reservoir through the two or more liquid paths into the droplet operations gap. The method may include dispensing two or more droplets from the liquid, at least one from each of the liquid paths. The method may include merging one or more droplets with the liquid flowed from the reservoir through the two or more liquid paths into the droplet operations gap. In some cases, the method may include retracting liquid from the droplet operations gap through the fluid paths and into the reservoir. Flowing liquid from the reservoir through the two or more liquid paths into the droplet operations gap may include, in each instance, flowing the liquid onto an electrode underlying the substrate. The electrode underlying the substrate may be situated at a position which may be across the droplet operations gap from a locus at which a liquid path enters the droplet operations gap. The liquid may include one or more beads. The method further may include causing the one or more beads to bind to one or more bead binding sites on a surface of the droplet operations gap. The one or more bead binding sites may be located atop an electrode. The electrode may be across the droplet operations gap from a locus at which a liquid path enters the droplet operations gap. The beads may include magnetically responsive beads. The method further may include magnetically attracting the magnetically responsive beads to a surface of the droplet operations gap. The surface of the droplet operations gap may be located atop an electrode. The electrode may be across the droplet operations gap from a locus at which a liquid path enters the droplet operations gap. The method further may include transporting one or more beads which may be not substantially magnetically responsive away from the locus of the substrate which may be atop the electrode which may be across the droplet operations gap from the opening. The method further may include attracting the magnetically responsive beads to an edge of the liquid which may be in the droplet operations gap. The method further may include arranging the magnetically responsive beads in a monolayer at an edge of the liquid which may be in the droplet operations gap. The method further may include binding the magnetically responsive beads to one or more bead binding sites on a surface of the droplet operations gap. Flowing liquid from the reservoir through the two or more openings into the droplet operations gap may be mediated at least in part by an electrode underlying the opening. The magnetically responsive beads may be arranged substantially in a monolayer at an edge of the liquid which may be in the droplet operations gap.

The invention provides a method of depositing beads on a substrate. The method may make use of a droplet actuator including one or more droplet actuator substrates arranged to form a droplet operations gap, one or more electrodes arranged to conduct one or more droplet operations in the droplet operations gap, and one or more liquid paths extending from the droplet operations gap, through the droplet actuator substrate, and to an exterior of the droplet operations gap. The method may include providing a deposition substrate arranged to receive liquid from the one or more openings, providing one or more droplets may include beads in the droplet operations gap, flowing liquid from the one or more droplets through the one or more liquid paths and onto the deposition substrate, and causing one or more beads to travel from within a droplet in the droplet operations gap, through one or more of the liquid paths, and into proximity with, or onto, the deposition substrate. In some cases, the method may include retracting liquid from the one or more droplets into the droplet operations gap. The deposition substrate may be associated with electrodes configured for conducting one or more droplet operations on the deposition substrate.

Flowing liquid from the one or more droplets through the one or more liquid paths and onto the deposition substrate may include, in each instance, flowing the liquid onto an electrode underlying the deposition substrate. The liquid may include one or more beads. The method further may include causing the one or more beads to bind to one or more bead binding sites on a surface of the deposition substrate. The one or more bead binding sites may be located atop an electrode. The beads may include magnetically responsive beads. The method further may include magnetically attracting the magnetically responsive beads to a surface of the deposition substrate. The method further may include attracting the magnetically responsive beads to an edge of the liquid which may be in contact with the deposition substrate. The method further may include arranging the magnetically responsive beads in a monolayer at an edge of the liquid which may be in contact with the deposition substrate. The method further may include binding the magnetically responsive beads to one or more bead binding sites on a surface of the deposition substrate.

The invention provides a droplet actuator device with a first substrate including a first sieve electrode, and a second substrate may include a droplet operations electrode. The first substrate and second substrate may be arranged such that a droplet positioned on the sieve electrode will move through the sieve electrode and onto the droplet operations electrode upon deactivation of the sieve electrode and activation of the droplet operations electrode. The droplet operations electrode may include a second sieve electrode. The first sieve electrode and the second sieve electrode may be vertically aligned. The droplet actuator device may include a third substrate may include a second droplet operations electrode, wherein the second substrate and third substrate may be arranged such that a droplet positioned on the second sieve electrode will move through the second sieve electrode and onto the second droplet operations electrode upon deactivation of the second sieve electrode and activation of the second droplet operations electrode. The droplet actuator device may include a top substrate arranged to form a droplet operations gap between the top substrate and the first substrate. The droplet operations gap may be sealed and filled with a liquid filler fluid. One or more of the sieve electrodes may include a mesh electrode, a screen electrode, an electrode having one or more openings therein. A sieve electrodes may include an electrode having one or more openings therein, e.g., an array of openings therein. The openings have a size which may be selected to permit beads having a first size to pass through the openings while restraining beads having a second, larger size from passing through the openings. The droplet operations electrode on the second substrate may be part of an arrangement of electrodes on the second substrate, and the arrangement of droplet operations electrodes may be configured for conducting one or more droplet operations on the second substrate. The arrangement of electrodes on a second substrate may include a second sieve electrode that may be not vertically aligned with the first sieve electrode on the first substrate. The device may include any number of substrates, and droplets may be passed from substrate-to-substrate and/or passed back and forth among substrates. For example, a third substrate may be provided including a second droplet operations electrode, wherein the second substrate and third substrate may be arranged such that a droplet positioned on the second sieve electrode will move through the second sieve electrode and onto the second droplet operations electrode upon deactivation of the second sieve electrode and activation of the second droplet operations electrode.

The invention provides a method of transporting a droplet from a first droplet actuator substrate to a second droplet actuator substrate. The method may make use of a droplet actuator device with a first substrate including a first sieve electrode, a droplet positioned on the sieve electrode, and a second substrate including a droplet operations electrode. The method may include activating the droplet operations electrode to cause the droplet to move through the sieve electrode and onto the droplet operations electrode.

The droplet operations electrode may include a second sieve electrode. The droplet actuator further may include a third substrate with a second droplet operations electrode. The method further may include activating the second droplet operations electrode to cause the droplet to move through the second sieve electrode and onto the second droplet operations electrode.

The droplet actuator further may include a top substrate arranged to form a droplet operations gap between the top substrate and the first substrate. The droplet operations gap may be sealed and filled with a liquid filler fluid.

One or more of the sieve electrodes may include a mesh, a screen, and/or one or more openings therein. Openings in the first sieve electrode have a size which may be selected to restrain first beads having a first size from passing through the openings.

The droplet on the first sieve electrode may include first beads. The method may include transporting the droplet through the first sieve electrode while retaining the first beads from passing through the sieve electrode to yield a droplet lacking first beads. The method may include solubilizing the first beads restrained by the sieve electrode in another droplet, yielding a droplet may include the first beads. Solubilizing the first beads restrained by the sieve electrode in another droplet may include transporting a droplet using electrode mediated droplet operations onto the sieve electrode to solubilize the first beads therein. The droplet including first beads may be removed from the droplet actuator and/or used for conducting one or more steps of an assay using the droplet including first beads. The droplet lacking first beads may be removed from the droplet actuator and/or used for conducting one or more steps of an assay using the droplet lacking first beads.

Openings in the first sieve electrode have a size which may be selected to permit first beads having a first size to pass through the openings and restrain second beads having a second, larger size from passing through the openings. The droplet on the first sieve electrode may include first beads and second beads. The method may include transporting the droplet through the first sieve electrode with first beads while retaining the second beads from passing through the sieve electrode to yield a droplet including first beads. The second beads restrained by the sieve electrode may be solubilized in another droplet, yielding a droplet including second beads. Solubilizing the second beads restrained by the sieve electrode in another droplet may include transporting a droplet using electrode mediated droplet operations onto the sieve electrode to solubilize the second beads therein. The droplet including second beads may be removed from the droplet actuator and/or used for conducting one or more steps of an assay using the droplet including second beads. The droplet including first beads may be removed from the droplet actuator and/or used for conducting one or more steps of an assay using the droplet including first beads.

The method may further include transporting the droplet having first beads through a second sieve electrode having openings sized to restrain the first beads, yielding a droplet lacking first beads and second beads. The first beads restrained by the sieve electrode may be solubilized in another droplet, yielding a droplet including first beads. Solubilizing the first beads restrained by the sieve electrode in another droplet may include transporting a droplet using electrode mediated droplet operations onto the sieve electrode to solubilize the first beads therein. The droplet including first beads may be removed from the droplet actuator and/or used for conducting one or more steps of an assay using the droplet including first beads. The droplet lacking first beads and second beads may be removed from the droplet actuator and/or used for conducting one or more steps of an assay using the droplet lacking first beads and second beads.

Positioning a droplet on a sieve electrode may include providing a droplet on an electrode adjacent to the sieve electrode; and deactivating the adjacent electrode and activating the sieve electrode to cause the droplet to move from the adjacent electrode onto the sieve electrode.

The invention provides a method of separating beads from a droplet. The droplet may include first beads having a first size. The method may include transporting the droplet through a first sieve electrode including first openings having a size which may be selected to restrain first beads from passing through the first openings to yield a droplet lacking first beads. The first beads restrained by the sieve electrode may be solubilized in another droplet, yielding a droplet including first beads. Solubilizing the first beads restrained by the sieve electrode in another droplet may include transporting a droplet using electrode mediated droplet operations onto the sieve electrode to solubilize the first beads therein. The droplet including first beads may be removed from the droplet actuator and/or used for conducting one or more steps of an assay using the droplet including first beads. The droplet lacking first beads may be removed from the droplet actuator and/or used for conducting one or more steps of an assay using the droplet lacking first beads.

The droplet may include further including second beads having a second size. The first openings have a size which may be selected to permit second beads to pass through the first openings to yield a droplet lacking first beads and including second beads. The method further may include transporting the droplet lacking first beads and including second beads through a second sieve electrode sieve electrode may include openings having a size which may be selected to restrain second beads from passing through the openings to yield a droplet lacking second beads. The second beads restrained by the sieve electrode may be solubilized in another droplet, yielding a droplet including second beads. Solubilizing the second beads restrained by the sieve electrode in another droplet may include transporting a droplet using electrode mediated droplet operations onto the sieve electrode to solubilize the second beads therein. The droplet including second beads may be removed from the droplet actuator and/or used for conducting one or more steps of an assay using the droplet including second beads. The droplet lacking second beads may be removed from the droplet actuator and/or used for conducting one or more steps of an assay using the droplet lacking second beads.

The invention provides a method of providing sub-droplets. The method may make use of a droplet actuator including one or more substrates arranged to form a droplet operations gap, and associated with at least one electrode arranged for conducting one or more droplet operations in the droplet operations gap. The method may include providing a droplet in the droplet operations gap in proximity to the electrode. The droplet may be surrounded by a liquid filler fluid which may be substantially immiscible with the droplet. The droplet may have a interfacial tension and position selected such that activation of the electrode causes the droplet to break apart into sub-droplets. The method may thus include activating the electrode and causing the droplet to break apart into sub-droplets. The sub-droplets together with surrounding filler fluid may constitute an emulsion. Causing the droplet to break apart into sub-droplets may produce at least tens of sub-droplets, at least hundreds of sub-droplets, at least thousands of sub-droplets, at least tens of thousands of sub-droplets, or more. The sub-droplets may include beads. The method may in some cases include flowing the sub-droplets away from the electrode in the filler fluid. In some cases, the sub-droplets may be sorted to identify sub-droplets with predetermined numbers or types of beads. The method may include combining at least a subset of the sub-droplets atop or otherwise associated with the electrode with a droplet having a interfacial tension selected to render a interfacial tension in a resulting combined droplet sufficiently high that activation of the electrode does not cause the resulting combined droplet to break apart into sub-droplets.

4 DEFINITIONS

As used herein, the following terms have the meanings indicated.

"Activate" with reference to one or more electrodes means effecting a change in the electrical state of the one or more electrodes which, in the presence of a droplet, results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Corp., Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in U.S. Patent Publication No. 20050260686, entitled, "Multiplex flow assays preferably with magnetically responsive beads as solid phase," published on Nov. 24, 2005, the entire disclosure of which is incorporated herein by reference for its teaching concerning magnetically responsive materials and beads. Whether magnetically responsive or non-responsive, beads can be buoyant or non-buoyant relative to droplets and/or filler fluids. In some cases, beads may be exceptionally dense and subject to gravity. Beads themselves may also be magnetic, i.e., the beads may produce a magnetic field. Certain properties of beads, such as magnetic properties may be adjustable or reversible by mechanisms such as addition or removal of a bead component, activation of an electrode in the vicinity of the bead, and/or exposure of a bead to a magnetic field. Beads may be pre-coupled with a biomolecule (ligand). The ligand may, for example, be an antibody, protein or antigen, DNA/RNA probe or any other molecule with an affinity for the desired target substance. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. Patent Application No. 61/047,789, entitled "Droplet Actuator Devices and Droplet Operations Using Beads," filed on Apr. 25, 2008; U.S. Patent Application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference.

"Divot" means any recessed or area in a droplet actuator surface. A divot may be present on electrodes, sidewalls of electrodes or any other structures (such as gaskets or spacers) present within a droplet operations gap, on a droplet operations surface, and/or in or on a reservoir associated with a droplet actuator. Any shape is suitable, examples include sections of spheres, ellipsoids, paraboloids, hyperboloids, cylinders, cones, cubes, discs, depressions, and the like. The depth of the divot may be only a fraction of the thickness of the material in which it exists; or it may occupy the entire thickness; or it may occupy two or more layers of materials. For example, one or more divots may be provided in a dielectric layer or hydrophobic layer in a droplet operations surface. A divot may be hydrophobic or hydrophilic in nature and may also be coated with materials. As an example, a divot may be coated with a material that serves the purpose of binding to a bead or other substance. Multiple divots may be provided as arrays in any pattern, e.g., checkerboard, star shaped, circular, linear, etc.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator. For examples of droplet fluids that may be subjected to droplet operations using the approach of the invention, see International Patent Application No. PCT/US 06/47486, entitled, "Droplet-Based Biochemistry," filed on Dec. 11, 2006. In various embodiments, a droplet may include a biological sample, such as whole blood, lymphatic liquid, serum, plasma, sweat, tear, saliva, sputum, cerebrospinal liquid, amniotic liquid, seminal liquid, vaginal excretion, serous liquid, synovial liquid, pericardial liquid, peritoneal liquid, pleural liquid, transudates, exudates, cystic liquid, bile, urine, gastric liquid, intestinal liquid, fecal samples, liquids containing single or multiple cells, liquids containing organelles, fluidized tissues, fluidized organisms, liquids containing multi-celled organisms, biological swabs and biological washes. A droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids. A droplet may include precipitates, such as amorphous or crystalline precipitates, which may be pre-existent in the liquid of the droplet, formed, dissolved, and reformed over time and/or due to chemical changes in the droplet. The droplet may be a material which can become a liquid with changes in temperature, pressure, electric field, agitation, etc., whereupon it becomes subject to one or more droplet operations. Conversely, droplets may be solidified.

"Droplet Actuator" means a device for manipulating droplets. For examples of droplet actuators, see U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al.; Pollack et al., International Patent Application No. PCT/US2006/047486, entitled "Droplet-Based Biochemistry," filed on Dec. 11, 2006; and Roux et al., U.S. Patent Pub. No. 20050179746, entitled "Device for Controlling the Displacement of a Drop Between two or Several Solid Substrates," published on Aug. 18, 2005; the disclosures of which are incorporated herein by reference. Certain droplet actuators will include a substrate, droplet operations electrodes associated with the substrate, one or more dielectric and/or hydrophobic layers atop the substrate and/or electrodes forming a droplet operations surface, and optionally, a top substrate separated from the droplet operations surface by a gap. One or more reference electrodes may be provided on the top and/or bottom substrates and/or in the gap. In various embodiments, the manipulation of droplets by a droplet actuator may be electrode mediated, e.g., electrowetting mediated or dielectrophoresis mediated or Coulombic force mediated. Examples of other methods of controlling liquid flow that may be used in the droplet actuators of the invention include devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed in droplet actuators of the invention.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; elongating or extending a droplet; retaining a droplet in position; incubating a droplet; heating a droplet; vaporizing a droplet; cooling a droplet; disposing of a droplet; solidifying a droplet, transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be partially or fully electrode-mediated. In some cases, droplet operations are further facilitated by the use of hydrophilic and/or hydrophobic regions on surfaces and/or by physical obstacles. Droplet operations may be partially or completely magnetically mediated, taking advantage of magnetic properties of the droplet and/or magnetic properties of particles or substances within the droplet.

"Filler fluid" means a liquid associated with a droplet operations substrate of a droplet actuator, which liquid is sufficiently immiscible with a droplet phase to render the droplet phase subject to electrode-mediated droplet operations. The filler fluid may, for example, be a low-viscosity oil, such as silicone oil. Other examples of filler fluids are provided in International Patent Application No. PCT/US2006/047486, entitled, "Droplet-Based Biochemistry," filed on Dec. 11, 2006; International Patent Application No. PCT/US2008/072604, entitled "Use of additives for enhancing droplet actuation," filed on Aug. 8, 2008; and U.S. Patent Publication No. 20080283414, entitled "Electrowetting Devices," filed on May 17, 2007; the entire disclosures of which are incorporated herein by reference. The filler fluid may fill the entire gap of the droplet actuator or may coat one or more surfaces of the droplet actuator. Filler fluid may be conductive or non-conductive. Two or more immiscible filler fluids may be used, e.g., a three phase system including two substantially immiscible filler fluids, which are each also substantially immiscible with droplet. A filler fluid can also be a solid, such as a wax. Upon heating the wax liquefies and permits execution of one or more droplet operations. The filler fluid may be a material which can become a liquid with changes in temperature, pressure, electric field, agitation, etc.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a splitting operation on a droplet, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, $CoO$, $NiO$, $Mn_2O_3$, $Cr_2O_3$, and $CoMnP$.

"Target substance" means a substance that is selected for collection within and/or removal from a source liquid. Examples include substances found in environmental samples, water samples, soil samples, biological samples, diagnostic samples, whole blood, lymphatic liquid, serum, plasma, sweat, tear, saliva, sputum, cerebrospinal liquid, amniotic liquid, seminal liquid, vaginal excretion, serous liquid, synovial liquid, pericardial liquid, peritoneal liquid, pleural liquid, transudates, exudates, cystic liquid, bile, urine, gastric liquid, intestinal liquid, fecal samples, liquids containing single or multiple cells, liquids containing organelles, fluidized tissues, fluidized organisms, liquids containing multi-celled organisms, biological swabs and biological washes. The target substances may in some cases be waste substances or interfering substances (e.g., substances that interfere with assays for other substances), and in some cases they may be analytes.

"Washing" with respect to washing a bead or surface means reducing the amount and/or concentration of one or more substances in contact with the bead or surface or exposed to the bead or surface from a droplet in contact with the bead or surface. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a bead or surface, where the droplet includes an initial amount and initial concentration of a substance. The washing operation may proceed using a variety of droplet operations. The washing operation may yield a droplet including the bead or exposed to the surface, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," granted on Oct. 21, 2008, the entire disclosure of which is incorporated herein by reference. It should be noted that in any embodiment which discusses washing of beads or surfaces, an alternative method may be performed by replacing wash droplets with droplets including one or more target substances having affinity for the magnetically responsive beads or surfaces. In this alternative method, the amount and/or concentration of one or more target substances bound to the bead or surface may be increased by successive exposure to multiple droplets including such target substances. This target substance capture operation may yield a droplet including the bead or exposed to the surface, where the droplet has a total amount and/or concentration of the target substance which is greater than the initial amount and/or concentration of the substance. Similarly, the bead or surface may have a total amount and/or concentration of the target substance which is greater than the initial amount and/or concentration of the substance present on the bead or surface. Capture of target substance on a surface or bead may, in certain embodiments, be followed by a washing method, e.g., as described above.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

5 BRIEF DESCRIPTION OF THE DRAWINGS

FIGS. 1A, 1B, 1C, and 1D illustrate top views of an example of a portion of a droplet actuator and show a method of separating and washing beads using a stationary magnet.

FIGS. 2A, 2B, 2C, and 2D illustrate top views of an example of a portion of a droplet actuator and show another method of separating and washing beads using a stationary magnet.

FIGS. 3A, 3B, 3C, 3D, and 3E illustrate top views of an example of a portion of a droplet actuator and show another method of washing beads using a movable magnet.

FIGS. 4A, 4B, 4C, 4D, and 4E illustrate top views of an example of a portion of a droplet actuator and show another method of washing beads using a movable magnet.

FIGS. 8A, 8B, 8C, and 8D illustrate top views of an electrode arrangement on a droplet actuator and demonstrate a method of re-suspending beads into solution from a stationary magnet.

FIGS. 9A, 9B, and 9C illustrate side views of an example of a portion of a droplet actuator and show and show a method of re-suspending beads into solution from a movable magnet.

FIGS. 10A, 10B, 10C, and 10D illustrate side views of an example of a portion of a droplet actuator and show a method of removing beads from a droplet actuator gap 1018 of the droplet actuator.

FIGS. 11A, 11B, 11C, and 11D illustrate top views of an example of a portion of a droplet actuator and show a method of particle separation by a method of separating magnetically responsive beads from non-magnetically responsive beads by (1) chemically aggregating the non-magnetically responsive beads; and (2) aggregating the magnetically responsive beads using magnetic forces.

Figure 12:
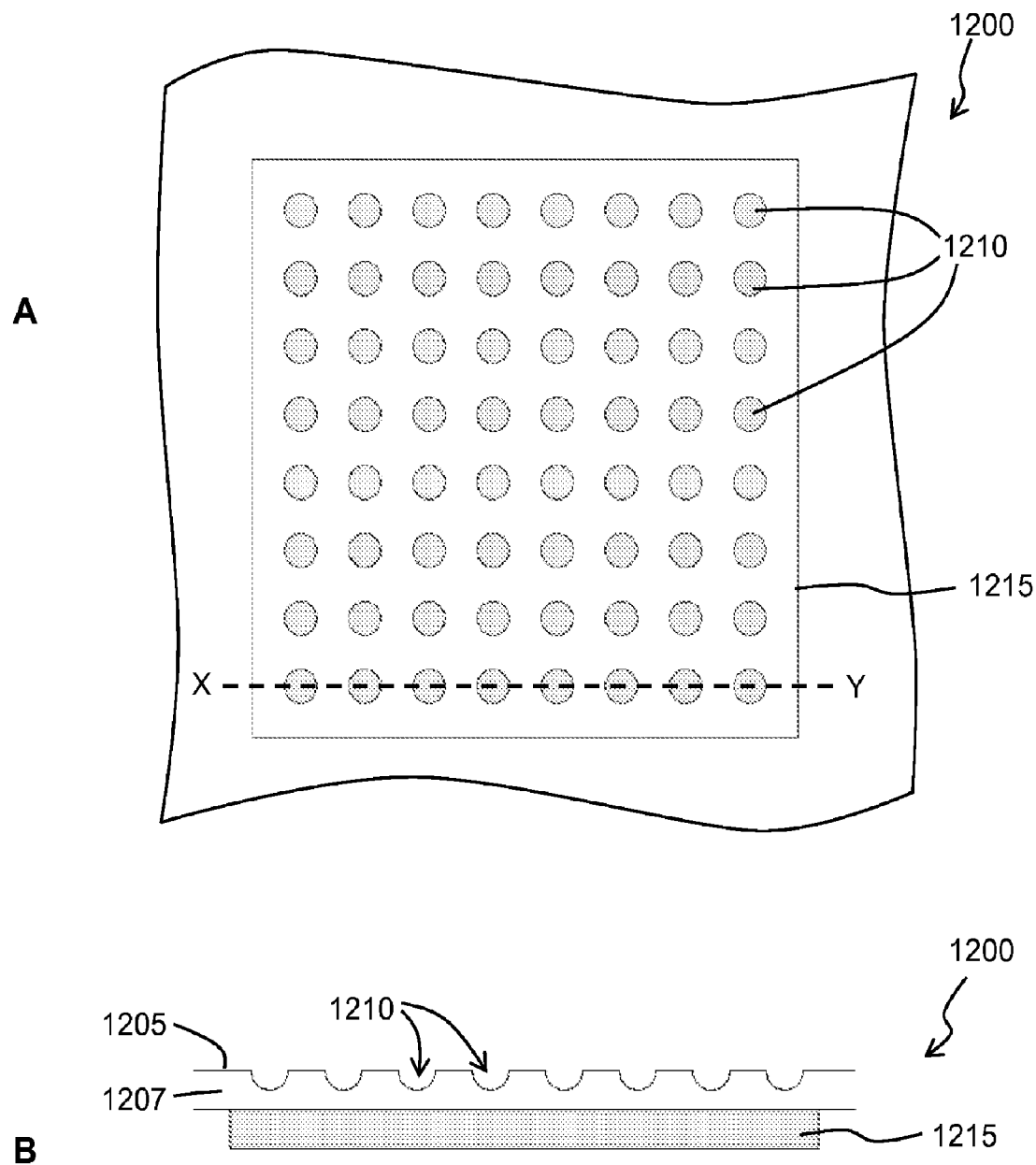

FIGS. 12A and 12B illustrate a region/cross-section of droplet actuator substrate that has recessed areas on the droplet operations surface for capturing beads.

Figure 13:
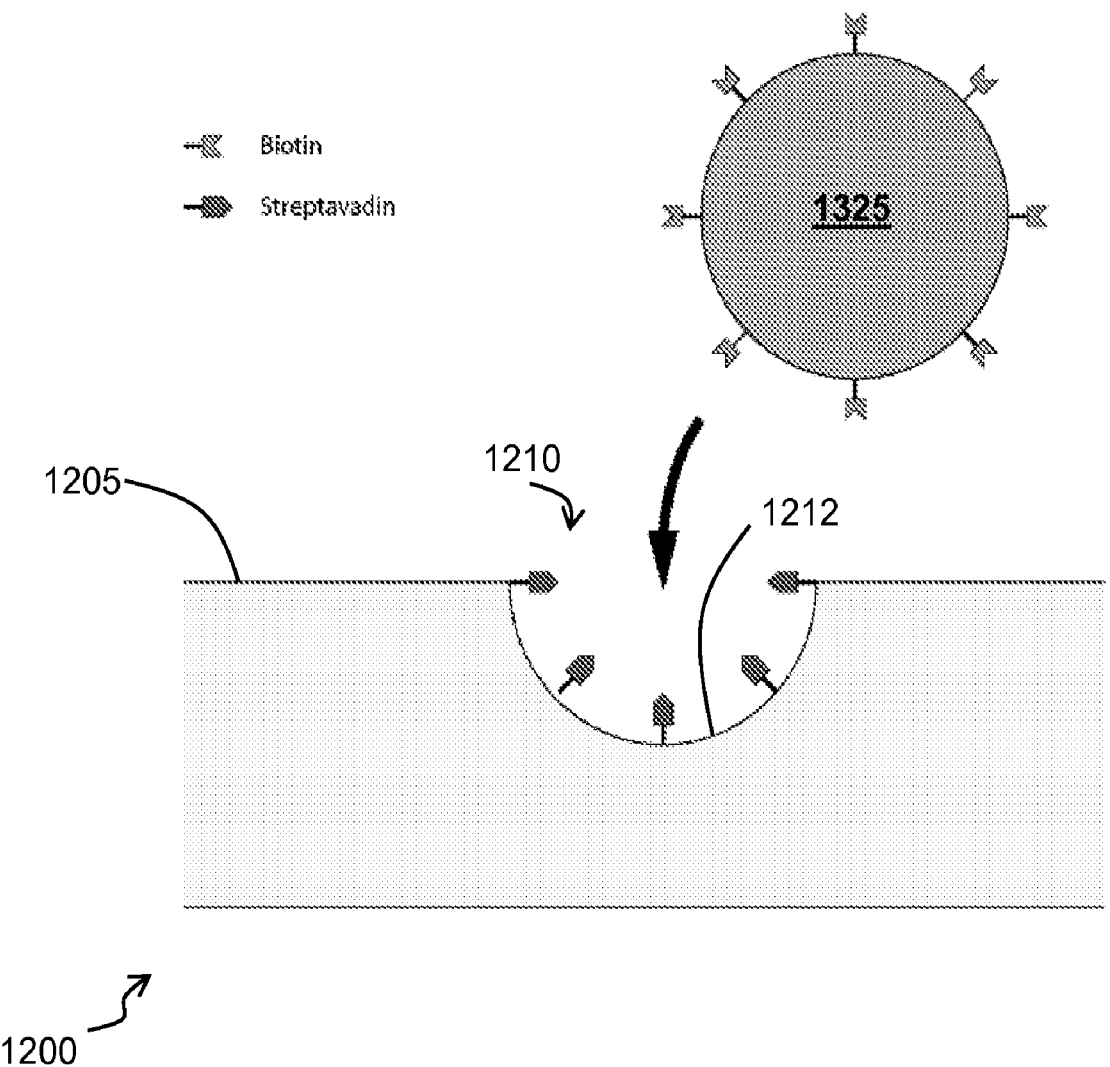

FIG. 13 is illustrative of embodiments in which a surface of divots includes a substance that has an affinity for the bead.

FIGS. 14A and 14B illustrate a top view and side view, respectively, of the droplet actuator substrate that has beads arrayed in divots.

Figure 15:
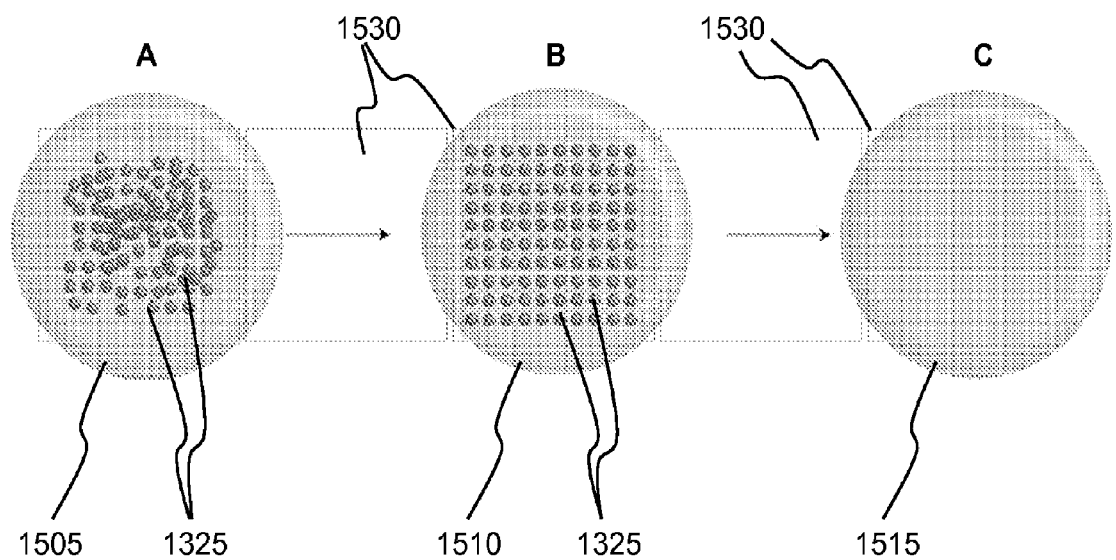

FIG. 15 illustrates steps A, B and C of a method of arraying beads on a surface of a droplet actuator.

Figure 16:
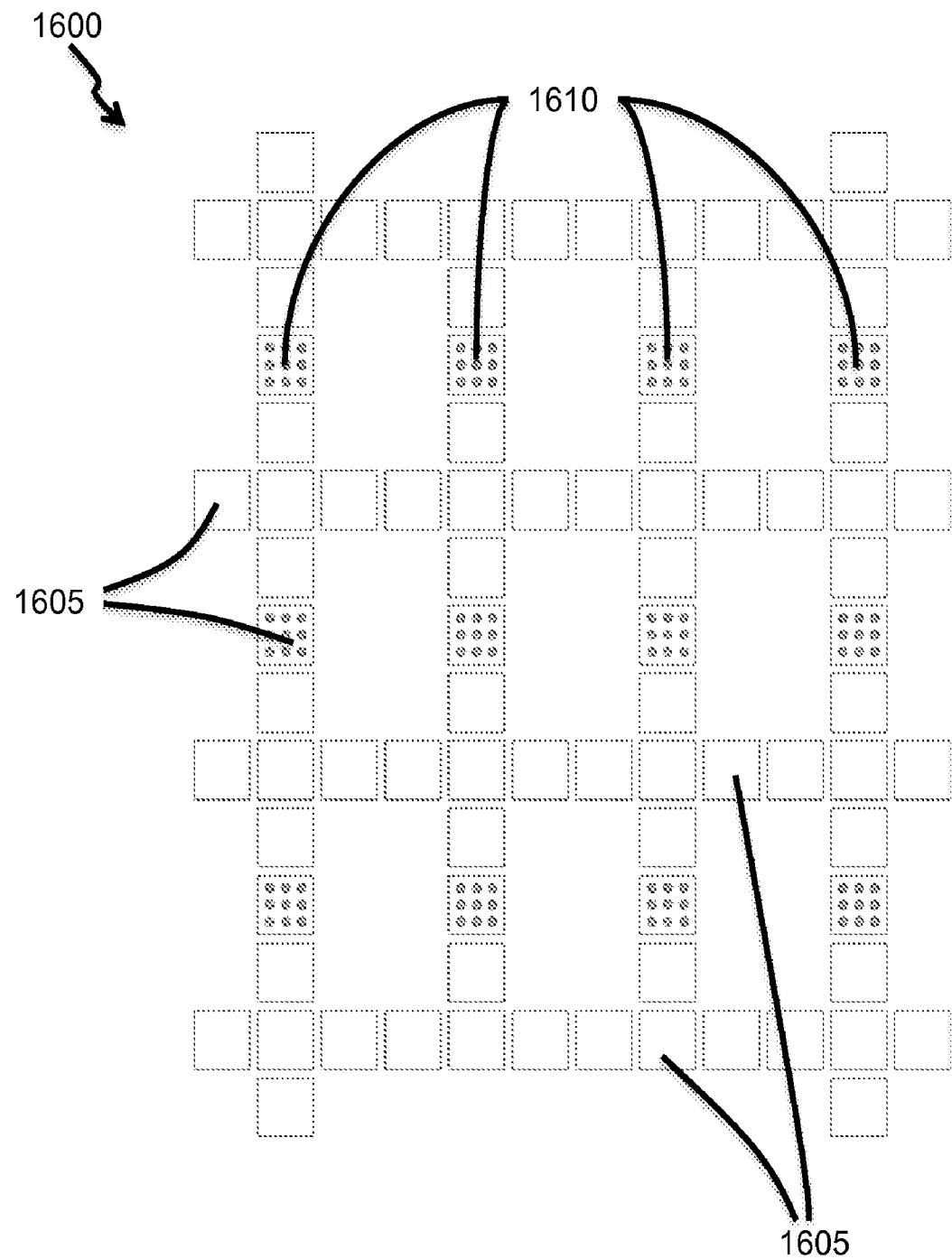

FIG. 16 illustrates an aspect of the invention in which a droplet actuator surface includes one or more paths or arrays of electrodes, including certain electrodes that have surface divots for immobilizing beads.

Figure 17:
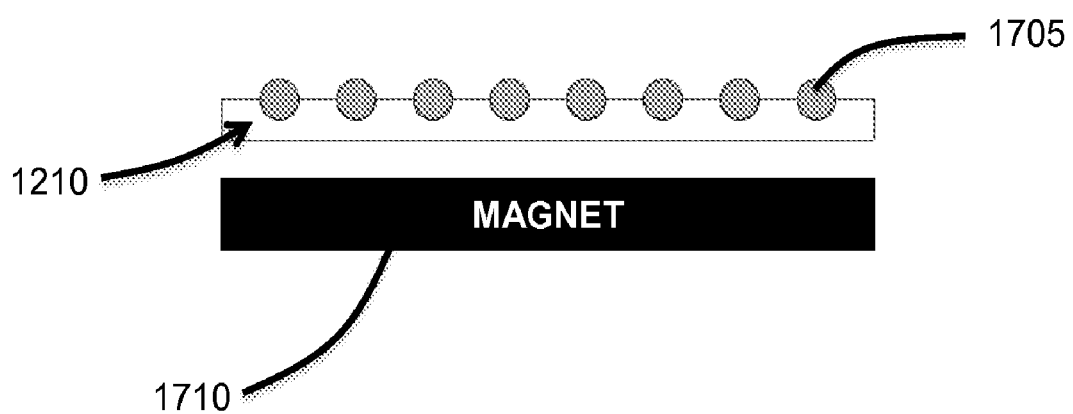

FIG. 17 illustrates an embodiment in which a magnet is used in combination with magnetically responsive beads in order to settle the magnetically responsive beads into the divots.

Figure 18:
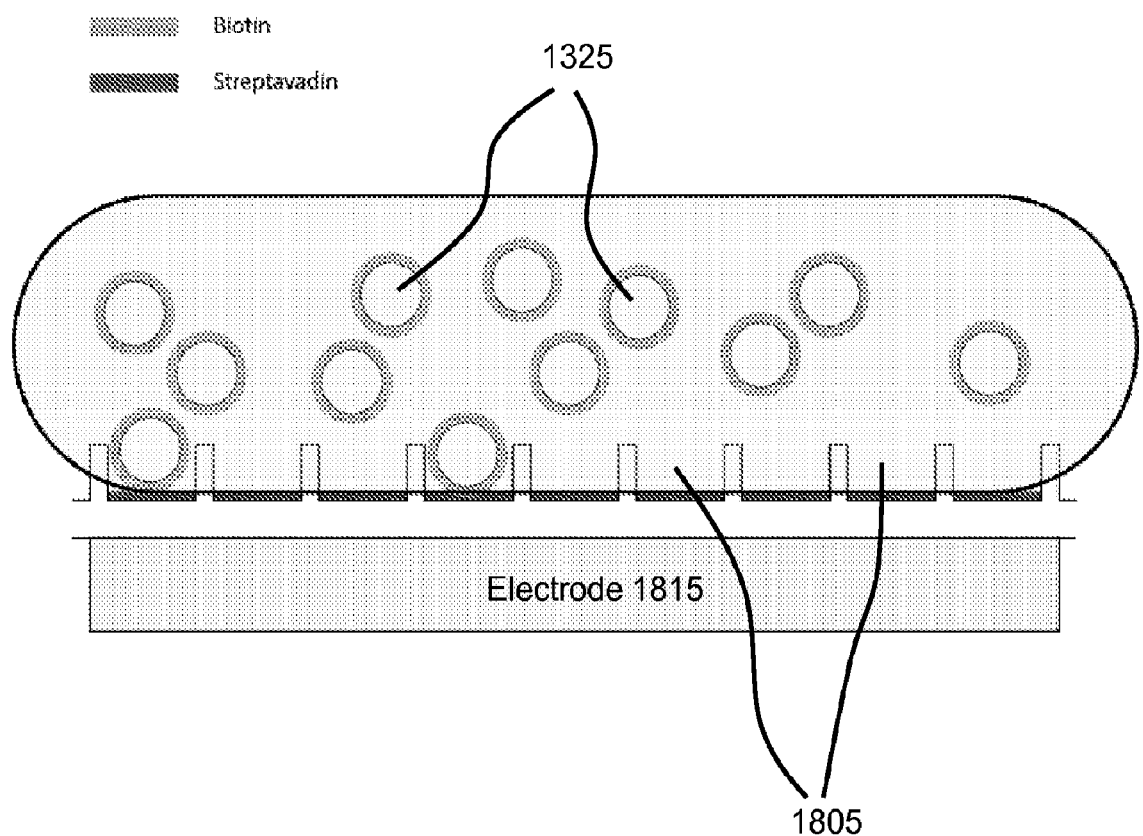

FIG. 18 illustrates a side view of a partial cross-section of an embodiment in which a path or grid of recessed areas is provided on the droplet operations surface in association with electrode.

Figure 19:
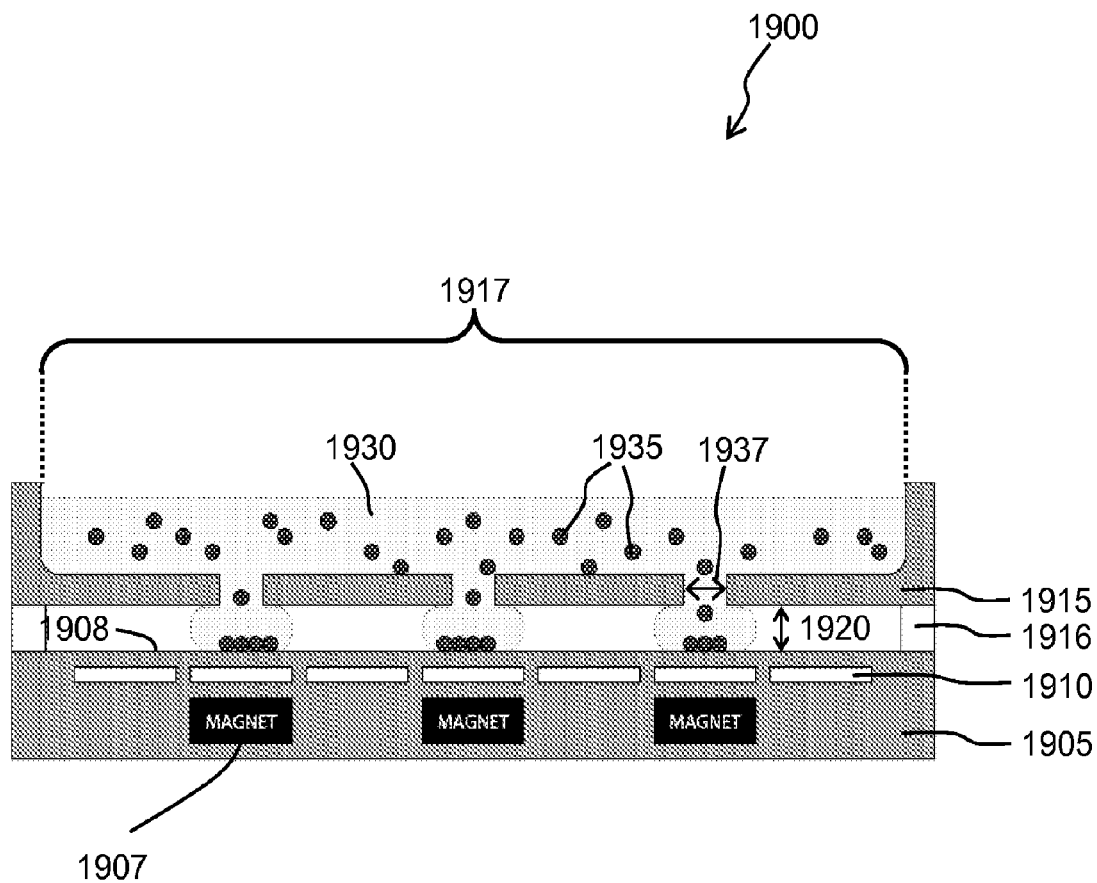

FIG. 19 illustrates a cross-section of an embodiment in which beads are loaded from a reservoir onto a droplet actuator.

Figure 20:
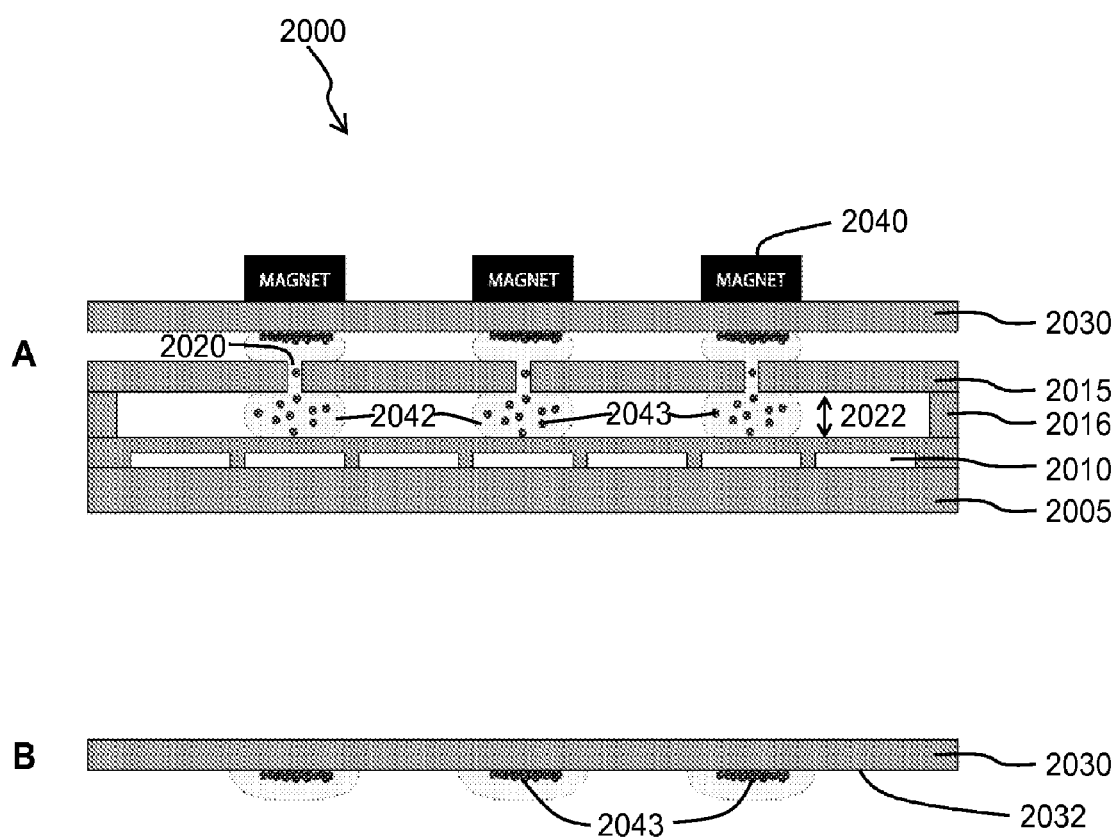

FIGS. 20A and 20B illustrate a bead stamping embodiment of the invention; and

Figure 21:
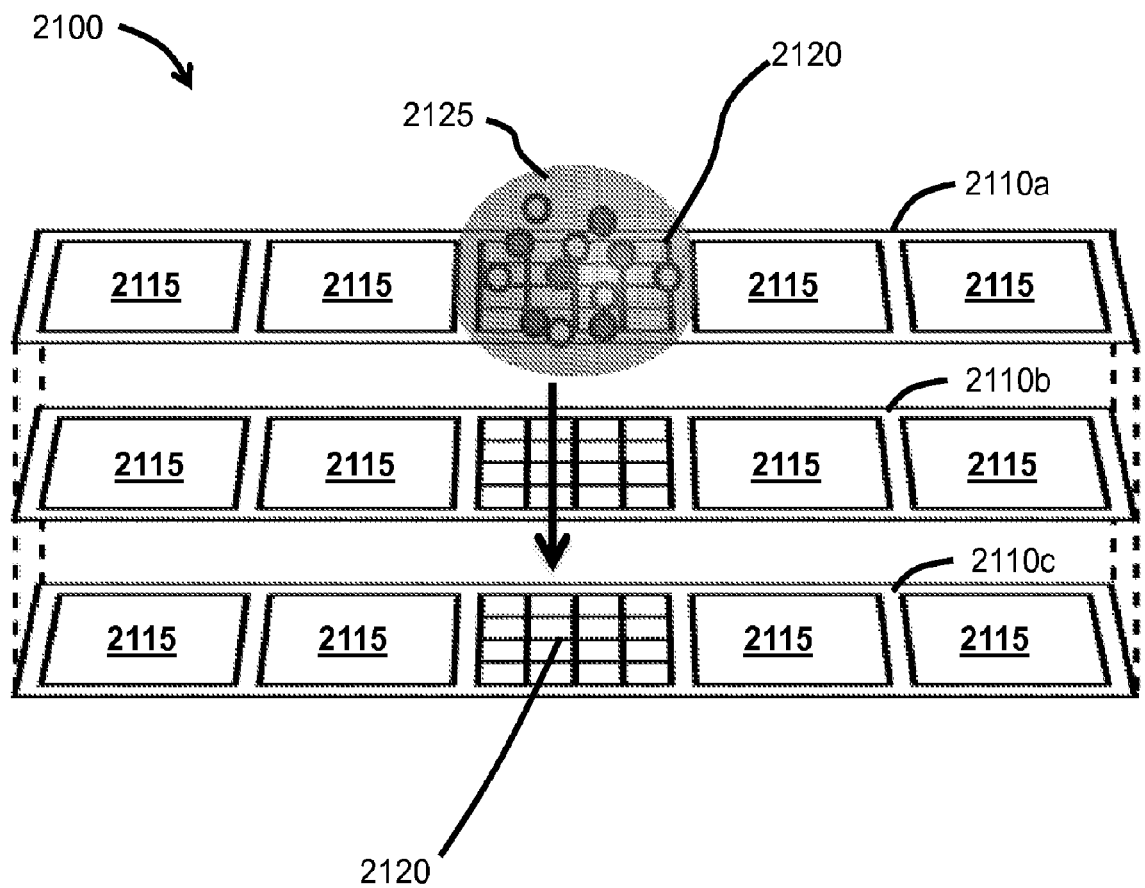

FIG. 21 illustrates a bead sorting embodiment of the invention that includes sieve electrodes.

Figure 22:
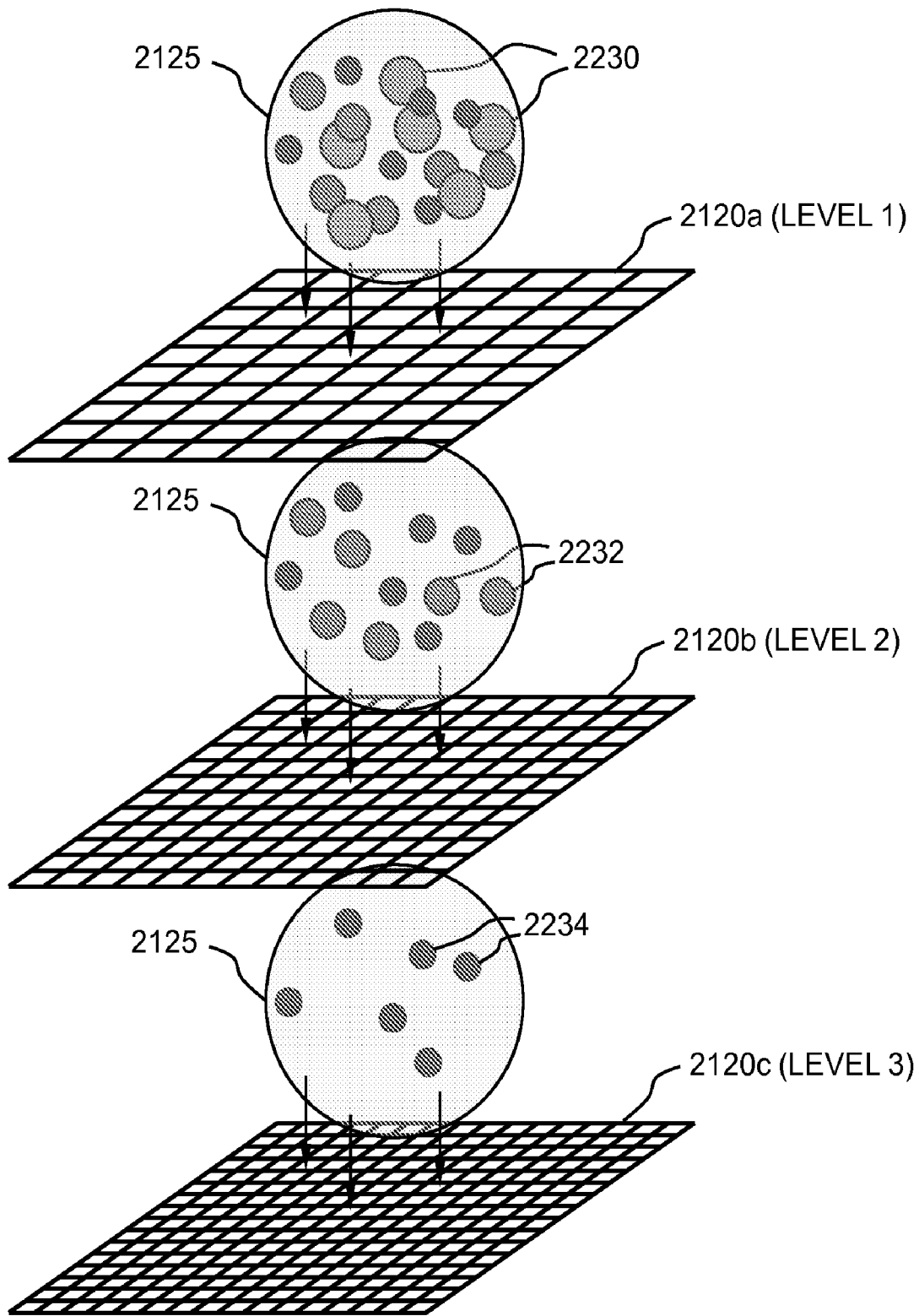

FIG. 22 illustrates additional aspects of a bead sorting embodiment of the invention that includes sieve electrodes.

Figure 23:
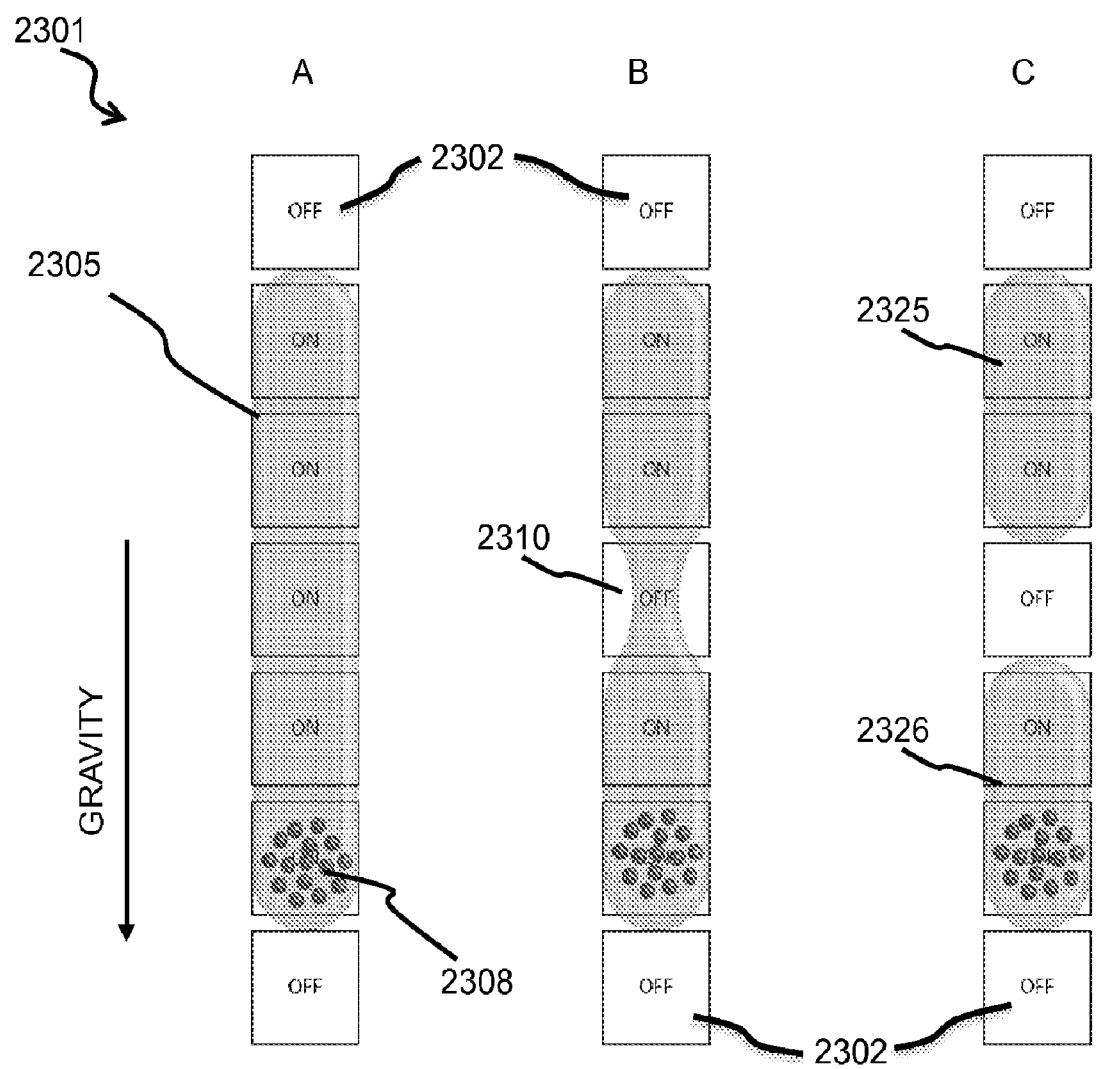

FIG. 23 illustrates a gravity-based bead concentration technique.

Figure 24:
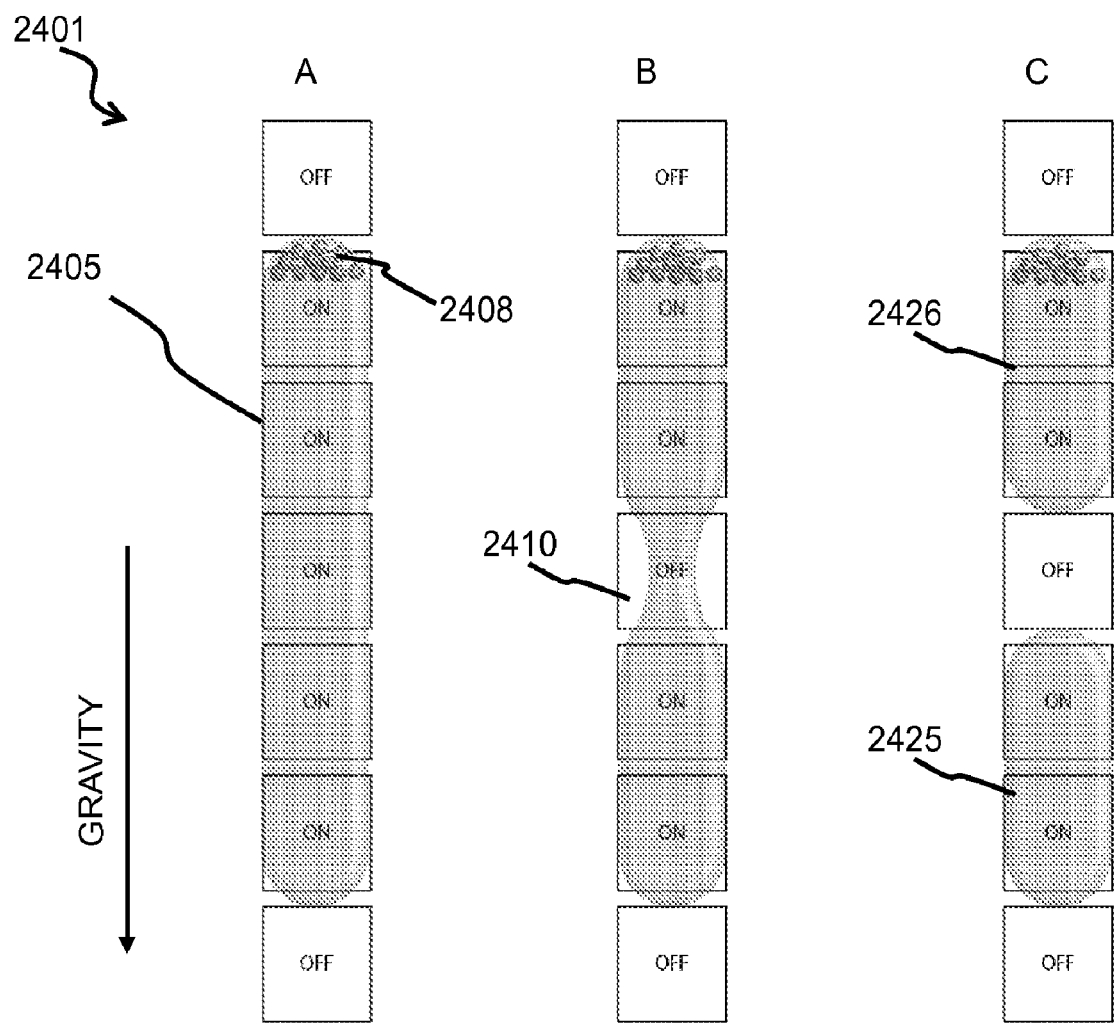

FIG. 24 illustrates a buoyancy-based bead concentration technique.

Figure 25:
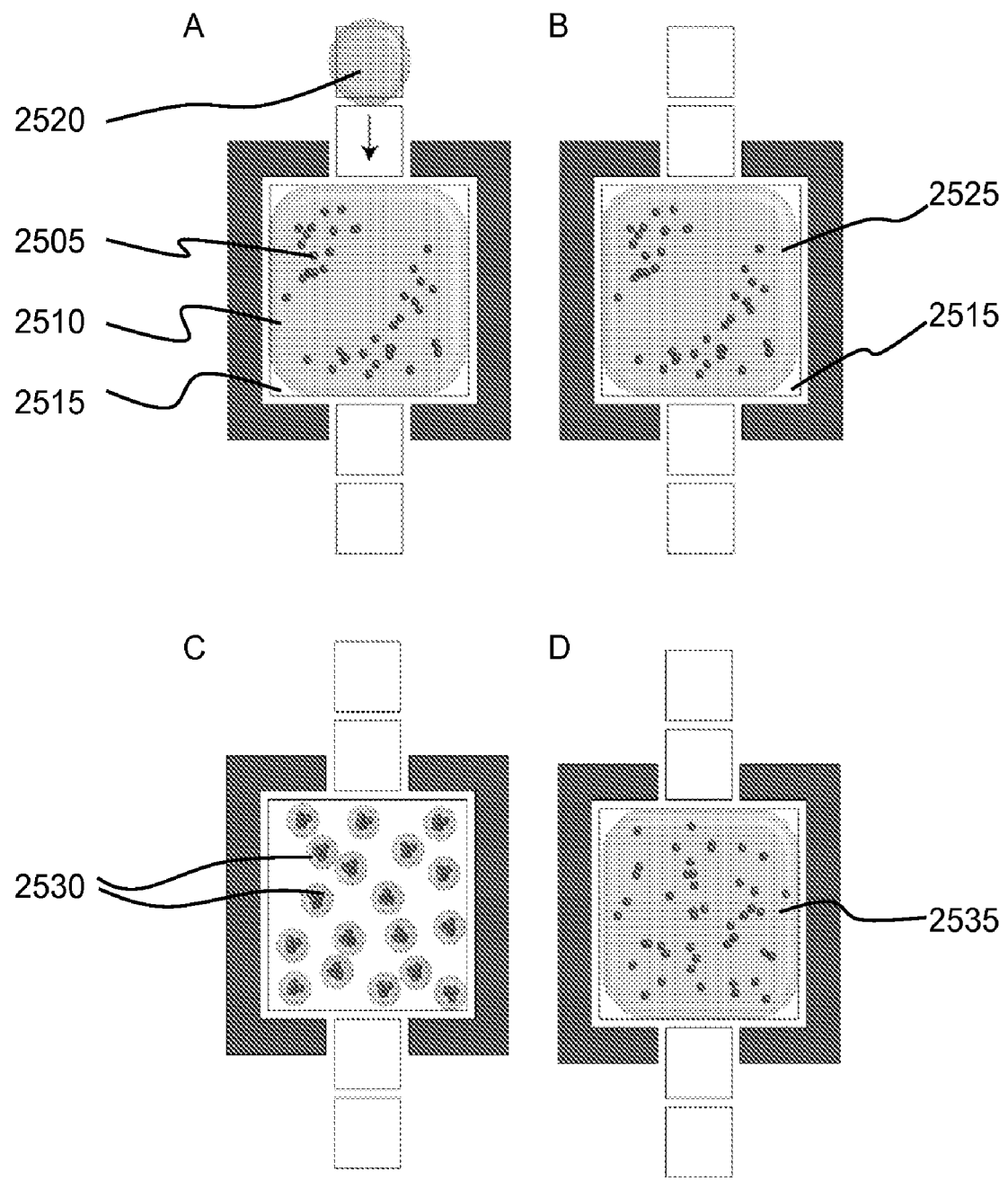

FIG. 25 illustrates an emulsion technique making use of beads.

6 DESCRIPTION

The invention provides droplet actuators and droplet actuator techniques. Among other things, the droplet actuators and methods are useful for manipulating beads on a droplet actuator, such as conducting droplet operations using bead-containing droplets on a droplet actuator. For example, beads may be manipulated on a droplet actuator in the context of executing a sample preparation protocol and/or an assay protocol. An output of the methods of the invention may be beads prepared for execution of an assay protocol. Another output of the methods of the invention may be results of an assay protocol executed using beads. Among the methods described herein are methods of concentrating beads in droplets, methods of washing beads, methods of suspending beads, methods of separating beads, methods of localizing beads within a droplet, methods of forming emulsions in which droplets include beads, methods of loading beads into a droplet operations gap of a droplet actuator, methods of organizing beads in a monolayer, and methods of capturing, trapping or restraining beads.

The methods of the invention may be optimized by adjusting properties of the system, including for example, interfacial tension of the droplet, magnetic bead properties and concentration, and pull force of the magnet exerted on the magnetically responsive beads. Certain methods of the invention may make use of magnets that are held in a stationary position, while bead-containing droplets and/or wash droplets are transported into and/or out of magnetic fields. Other methods of the invention may provide bead-containing droplets and/or wash droplets that are held in a stationary position, while movable magnets are used for manipulating the beads. Additionally, various combinations of low and high interfacial tension fluids, as well as methods of changing interfacial tension are used.

6.1 Separating and/or Washing Beads

FIGS. 1A-1D illustrate top views of an electrode arrangement 100 on a droplet actuator. The figures illustrate a method of separating beads from a bead-containing droplet and washing the beads. The method makes use of a stationary magnet arranged to retain beads as a bead-containing droplet is transported away from the magnetic field. Bead-containing droplets and wash droplets are transported into and out of the magnet field of the magnet using droplet operations mediated by electrodes.

A droplet actuator may include an arrangement of droplet operations electrodes 100 (e.g., electrowetting electrodes). Shown in FIG. 1 as a linear path of electrodes, any arrangement is suitable which is configured to conduct one or more droplet operations on a droplet operations surface of the droplet actuator. Magnet 114 is arranged in sufficient proximity to droplet operations electrodes 100 and the droplet operations surface in order to produce a magnetic field which will immobilize, substantially immobilize or otherwise restrain movement of magnetically responsive beads in a droplet on the droplet operations surface. As shown, magnet 114 is arranged such that the magnetic field will immobilize or substantially immobilize or otherwise restrain movement of magnetically responsive beads atop a certain droplet operations electrode 110 (e.g., droplet operations electrode 110M). As with other magnets described herein, magnet 114 may be any device which emits a suitable magnetic field, such as a permanent magnet or electromagnet. Droplet actuator may include a droplet 118 on a droplet operations surface that may be subjected to droplet operations (e.g., transported) using droplet operations electrodes 100.

Droplet 118 may be formed using a buffer having an interfacial tension which is sufficiently low to permit magnetic beads 122 to remain behind atop magnet 114 when bead-containing droplet 118 is transported away from magnet 114. The transporting away may be mediated by the electrodes, e.g., by electrowetting-mediated or dielectrophoresis-mediated droplet operations. In order to enhance the "snapping off" of beads from a droplet that is being transported away from magnetically restrained beads, higher surfactant concentrations may be used. The magnetic bead concentration and the pull force of the magnet may be relatively high.

In general, the following parameters may be adjusted so that transport of a magnetically responsive bead-containing droplet away from the magnetic field will leave behind a highly concentrated droplet including the magnetically responsive beads, which is essentially snapped off as the bead-containing droplet moves away from the magnetic field: interfacial tension of the droplet, magnetic bead properties and concentration, and pull force of the magnet exerted on the magnetically responsive beads. For example, the surfactant may be Tween 20, and the concentration of Tween 20 may range from about 0.02% to about 0.1%. Of course, the required concentration will vary depending on the surfactant type. The desired interfacial tension range may typically be in the range of about 1 dynes/cm to about 4 dynes/cm. The magnetic bead concentration range is typically from about 10 mg/mL to about 30 mg/mL. Pull force of the magnet may typically range from about 5 lbs to about 100 lbs.

Droplet 118 may include one or more beads 122. Beads 122 may be magnetically responsive beads. Beads 122 may include one or more target substances adhered thereto. In some cases, droplet 118 includes a liquid having an interfacial tension that is sufficiently low that beads 122 remain behind when droplet 118 is transported away from electrode 110M.

Figure 1A:
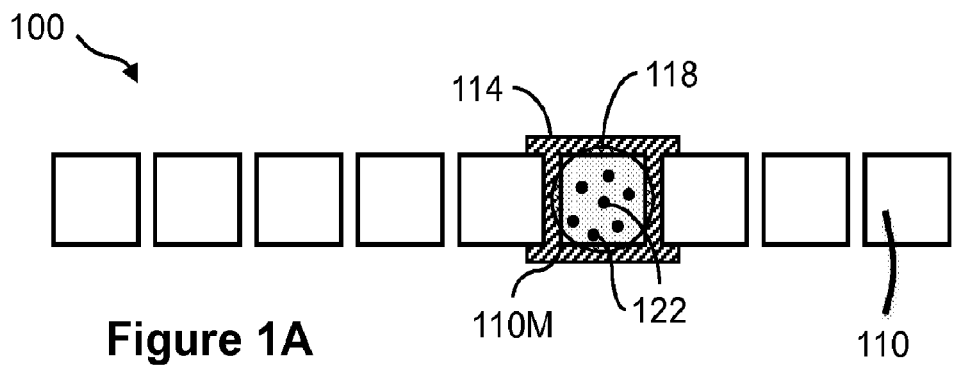

The following steps are illustrative of a method of separating beads from a droplet and washing the beads:

In FIG. 1A, bead-containing droplet 118 with magnetically responsive beads 122 is positioned at droplet operations electrode 110M. Magnetically responsive beads 122 are attracted to magnet 114. Electrode 110M may or may not be activated.

Figure 1B:
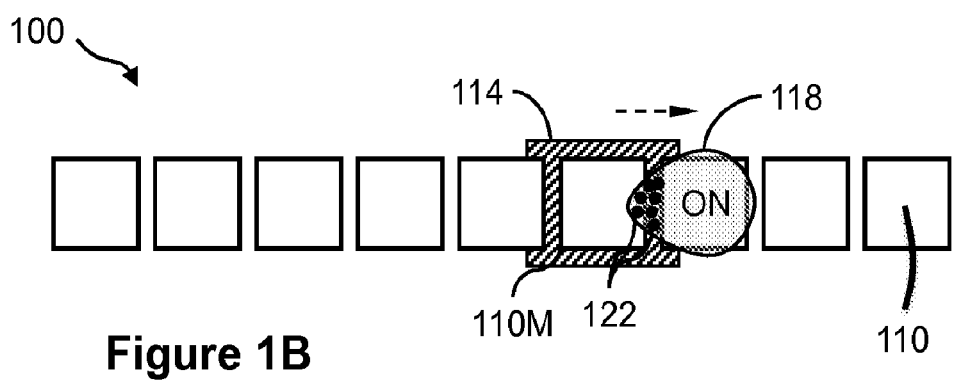

In FIG. 1B, droplet 118 is transported using droplet operations away from droplet operations electrode 110M and onto an adjacent activated droplet operations electrode 110, which is activated. Electrode 110M is deactivated and the adjacent activated droplet operations electrode 110 is activated to cause transport of droplet 118 onto the adjacent activated electrode. As droplet 118 moves away from droplet operations electrode 110M onto the adjacent activated electrode 110, a concentration of beads 122 is formed at the side of droplet 118 that is closest to magnet 114. As droplet 118 is transported away from magnet 114, sub-droplet 126 including the magnetically restrained beads 122 breaks away from droplet 118. The transporting of droplet 118 may be electrode mediated, e.g., electrowetting mediated and/or dielectrophoresis mediated.

In some embodiments, the droplet includes a quantity of magnetically responsive beads to cause the beads to break away from the droplet and immobilize on the electrode atop the magnet. This phenomenon may occur when the droplet is brought into the vicinity of the magnetic field. It is not necessary for the bead droplet to traverse the length of the magnet. In a related embodiment, two or more droplets, each including a low concentration of magnetic beads may be merged together to yield a droplet a sufficiently quantity of magnetically responsive beads to cause the beads to break away from the droplet and immobilize on the electrode atop the magnet. For example, the two or more droplets may be combined on the electrode which has the maximum magnetic gradient. The increased quantity of magnetic beads may break away from the droplet, e.g., when the droplet is transported away from the magnet. The transporting away from the magnet may be conducted using, for example, droplet operations mediated by electrodes.

Figure 1C:
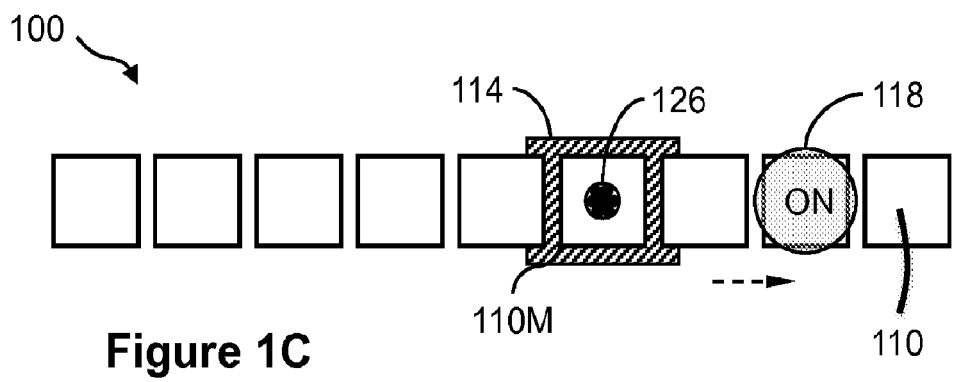

FIG. 1C shows droplet 118 transported using droplet operations further away from droplet operations electrode 110M to another droplet operations electrode 110. The concentration of beads 122 in droplet 126 has broken away or "snapped off" from droplet 118. This breaking away of the small sub-droplet occurs because of (1) the magnetically restrained concentration of beads 122 at one side of droplet 118, (2) the low interfacial tension of droplet 118, and (3) a suitably strong magnetic force that is provided by magnet 114, which is attracting beads 122. When beads 122 snap off of droplet 118, a relatively small and highly concentrated bead-containing droplet 126 remains behind at droplet operations electrode 110M and held in place or restrained by magnet 114. The volume of bead-containing droplet 126 is typically just large enough to encapsulate beads 122. For example, bead-containing droplet 126 may be from about ⅕th to about ¹⁄₂₀th the volume of the original droplet 118, depending on the concentration of beads 122. Beads 122 are separated from the original bead-containing droplet 118 to form a substantially bead-free droplet 118.

Figure 1D:
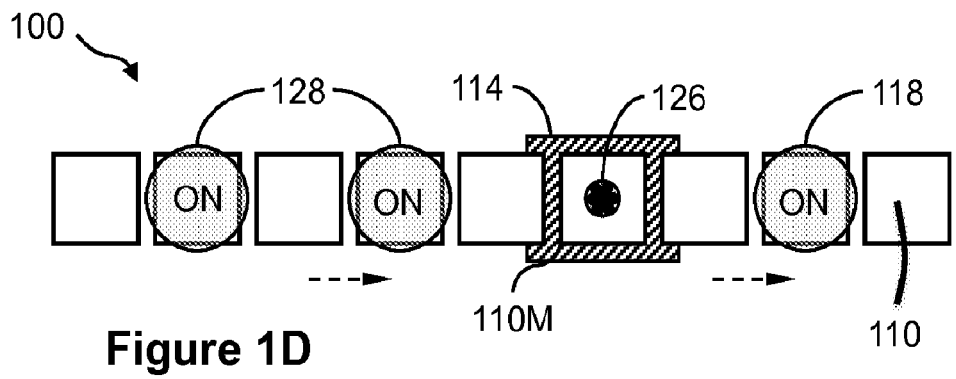

FIG. 1D illustrates a bead washing step in which one or more wash droplets 128 is/are transported into contact with bead-containing droplet 126. Each wash droplet 128 merges with and dilute the contents of bead-containing droplet 126. One or more of such wash droplets 128 may merge with bead-containing droplet 126, yielding a 1×, 2×, 3×, or larger droplet. As described above with respect to droplet 118, the merged droplet (not shown) is then transported away from beads 122, leaving behind a bead-containing droplet 126. This bead-containing droplet 126 may have a reduced amount and/or concentration of one or more substances in contact with beads 122 or exposed to beads 122 from the liquid portion of droplet 126. The merge and split operations are facilitated by selection of a low interfacial tension of wash droplets 126 relative to the magnetic attraction between magnet 114 and beads 122 at droplet operations electrode 110M.

This method of bead washing is particularly effective because a large amount of the initial droplet is removed in the first step, leaving only a small amount of the initial droplet to be washed away using, for example, a merge-and-split droplet washing protocol. In this method of the invention, an effective bead washing operation of the beads 122 within bead-containing droplet 126 is provided by use of, for example, 10, 9, 8, 7, 6, 5, 4, 3, 2 or 1 wash droplets 128 only. This is a significant improvement over existing bead washing methods that may require many more droplet operations to achieve the same washing effectiveness. Thus, for example, in one embodiment, the method of the invention removes about 95, 96, 97, 98, 99, 99, 99.9, 99.99, 99.999, 99.9999, or 99.99999 percent of unwanted molecules in the droplet surrounding beads by use of only 10, 9, 8, 7, 6, 5, 4, 3, 2 or 1 wash droplets.

In a related embodiment, the inventors have discovered that the snapping off of magnetically responsive beads may be controlled by controlling the shape of a droplet. As an example, beads in a droplet in a droplet operations gap may snap off in the presence of a magnet when the droplet is permitted to take on an energetically favorable shape, given the forces within the gap acting on the droplet, such as interfacial tension and capillary forces. Snapping off may occur, for example, when the size of the droplet is larger than the size or number of electrodes that are controlling the droplet or when no electrodes are controlling the droplet. The droplet may be stationary in the vicinity of the magnet or may be undergoing a droplet operation, such as transported away from the magnet, when the snapping off occurs. To illustrate, all other parameters being equal, a 2× droplet may be provided in which the beads will snap off from the droplet when it is subjected to electrowetting by a single (1×) electrode, but will not snap off from the droplet when it is subjected to electrowetting by two such electrodes. Similarly, droplet may be provided in which the beads will not snap off from the droplet when it is subjected to electrowetting by an electrode that has a certain footprint that is sufficiently close to the footprint of the droplet, but will snap off from the droplet when it is subjected to electrowetting by an electrode having a smaller footprint. Depending on the size of the one or more electrodes acting on the droplet, the electrowetting force may dominate the magnetic force, and the magnetically responsive beads will be retained in the droplet; or vice versa, the magnetic force may dominate the electrowetting force, and the magnetically responsive beads will be removed from the droplet.

FIGS. 2A-2D illustrate top views of an electrode arrangement 100 on a droplet actuator. The figures illustrate a method of separating beads from a bead-containing droplet and washing the beads. The method is similar to the method described above with respect to FIGS. 1A-1E, except that, droplets 118 are replaced with an elongated droplet or droplet 130. Droplet 118 illustrated FIGS. 1A, 1B, 1C, and 1D is approximately a 1× droplet, meaning that its footprint is similar to or approximately equal to the area of one droplet operations electrode 110. Droplet 130 of FIGS. 2A, 2B, 2C, and 2D is a 3× droplet, meaning that its footprint is approximately 3 times the area of one droplet operations electrode 110. Like droplet 118, droplet 130 may be formed of low interfacial tension wash liquid. Droplet 130 is not limited to being a 3× droplet; any suitably sized slug may be used, e.g., 2×, 3×, 4×, 5×, or larger.

Figure 2A:
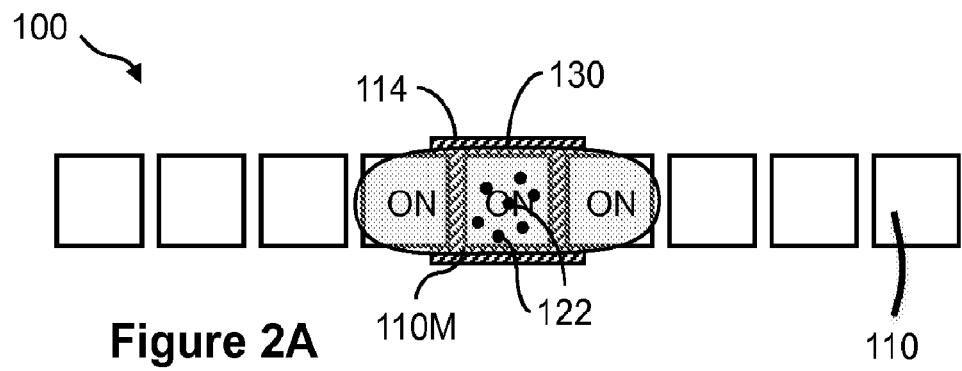
Figure 2B:
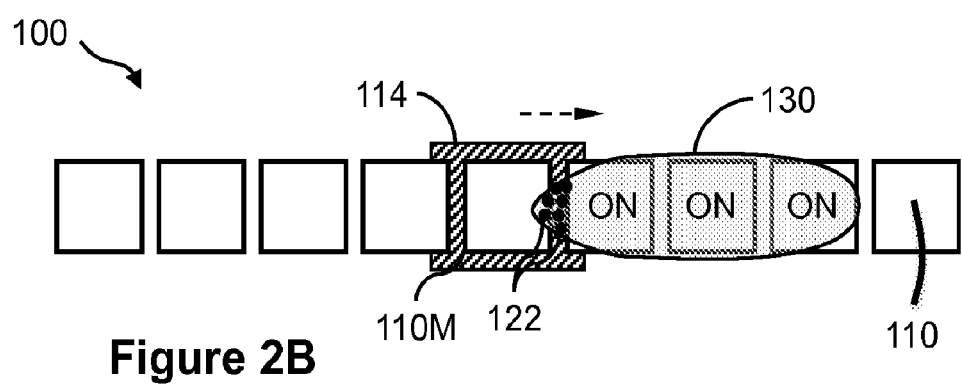
Figure 2C:
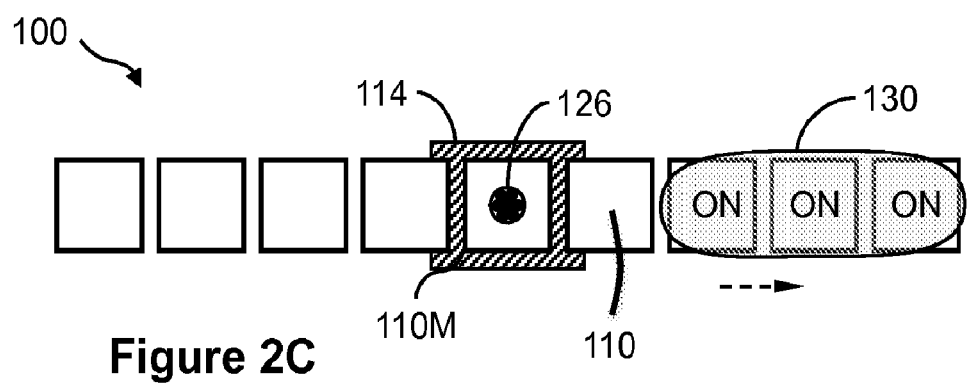

FIGS. 2A, 2B, and 2C show a method of separating beads 122 from droplet 130. A highly concentrated bead-containing droplet 126 remains at droplet operations electrode 110M. Droplet 126 is essentially restrained from being transported due to the influence of the magnetic field of magnet 114 on beads 122. A substantially bead-free droplet 130 is also formed when the beads break away from the parent droplet to form droplet 126. The effect can be enhanced by increasing the bead concentration or bead mass within a droplet, e.g., by merging several droplets with a low mass of magnetic beads to increase the mass of magnetic beads as described previously.

Figure 2D:
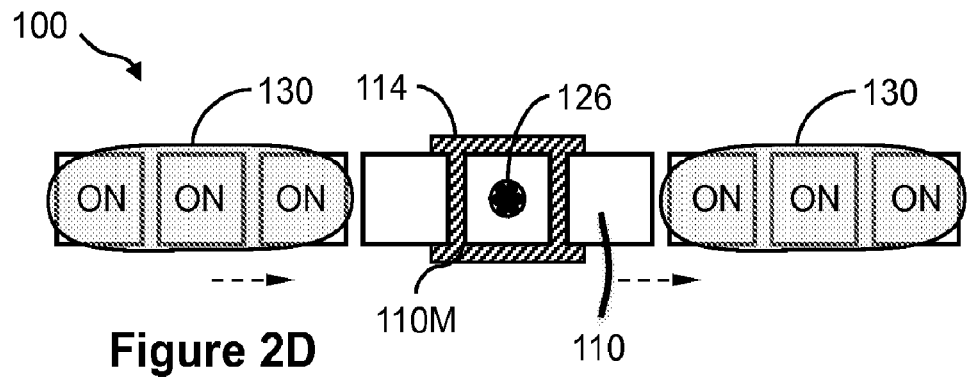

FIG. 2D shows a process of washing beads in bead-containing droplet 126. The process is analogous to the washing process described with respect to FIG. 1D, except that droplet 130 is a 3× droplet. The elongated wash droplets 130 are particularly effective in washing away unbound materials because, among other things, large dilution factors can be achieved by diluting the unbound materials using fewer washes when compared to washing with a 1× droplet.

As compared with existing bead washing techniques, the number of droplet operations required for effective washing is significantly reduced. Thus, for example, in one embodiment, the method of the invention removes about 95, 96, 97, 98, 99, 99, 99.9, 99.99, 99.999, 99.9999, or 99.99999 percent of unwanted molecules in the droplet surrounding in the bead-containing droplet in a method that makes use of 10, 9, 8, 7, 6, 5, 4, 3, 2 or 1 wash droplets, where each wash droplet is a 1×, 2×, 3×, 4×, 5×, or larger wash droplet.

FIGS. 3A-3E illustrate top views of an electrode arrangement 100 of droplet actuator of FIGS. 1A through 1D and show a method of washing beads using a movable magnet. "Movement" of the magnet, as discussed herein, is relative to the droplets arranged on the droplet actuator. It will be appreciated that either the magnet or the droplet actuator or both may be the moving part. Thus, the movable magnet may actually be in a fixed position, and the droplet actuator may be moved; the droplet actuator may be in a fixed position, and the magnet may be moved; or both the droplet actuator and the magnet may be moved. In this and other moveable magnet embodiments, the moveable magnet may, for example, be located above the top substrate, below the bottom substrate, in a groove or slot within or partially within the top substrate and/or bottom substrate, and/or in the droplet operations gap. Further, in an alternative embodiment, the moveable magnet may be replaced with a series of electromagnets that may be switched on/off in series, so as to pass the magnetically responsive beads from magnet-to-magnet. As with the examples already discussed, parameters such as interfacial tension of the droplet, magnetic bead properties and concentration, and pull force of the magnet exerted on the magnetically responsive beads, may be adjusted to facilitate or optimize the operations described. Where a moving magnet is used with stationary droplets, any means for forcing droplets to remain substantially in position during washing may be employed. For example, the droplets may be held stationary by electrowetting, dielectrophoresis and/or capillary forces.

As illustrated in FIGS. 3A-3E, magnet 114 is movable relative to droplet operations electrodes 100. Magnet 114 is movable along the path of droplet operations electrode arrangement 100. As magnet 114 moves along the path of droplet operations electrode arrangement 100, beads 122 are pulled by the magnetic force of magnet 114 through wash droplet 130. Further, in some cases, beads 122 may be pulled out of droplet 130 to form a sub-droplet 326 including substantially all of beads 122. Droplet 130 is positioned relative to magnet 114 using droplet operations atop three of the droplet operations electrodes in electrode arrangement 100. Droplet 130 may be retained in place atop these droplet operations electrodes 100 or moved as beads 122 pass through droplet 130.

In another embodiment, droplet can be moved in the forward direction while the magnet is moved in the opposite direction. This ensures effective removal of the unbound material in less time when compared to washing using a stationary droplet or a stationary magnet. In another embodiment, both droplet and the magnet can be moved in the forward direction, with one of them moving faster than the other. This approach may improve washing efficiency by enhancing resuspension of magnetic beads within the droplet and improving removal of unbound material trapped within the interstices of the magnetic beads.

Figure 3A:
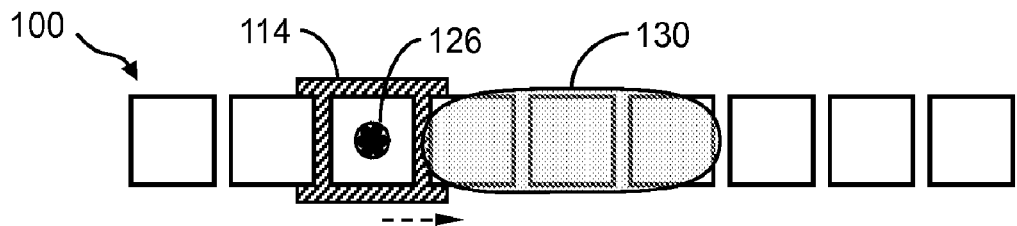

The following steps illustrate a method of washing the beads and separating beads from a droplet:

FIG. 3A shows bead-containing droplet 126 restrained in place atop an electrode of electrode path 100 by the magnetic field of magnet 114. Beads 122 of bead-containing droplet 126 are the target of the wash operation. Droplet 130 is also provided on the electrode path 100. Droplet 130 may be a wash droplet, or in alternative embodiments, may be a droplet including a target substance having affinity for beads 122.

Figure 3B:
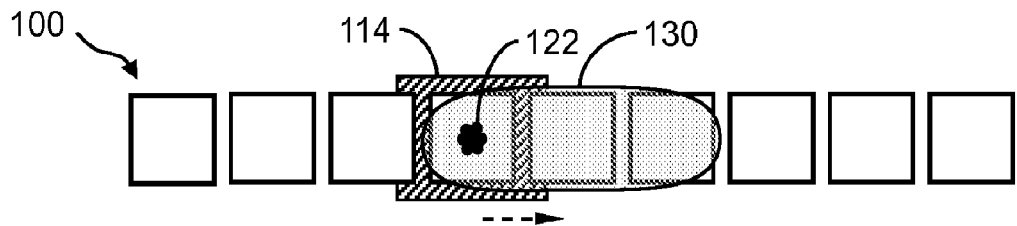

FIG. 3B shows droplet 126 pulled along electrode arrangement 100 by magnet 114 into contact with droplet 130 and merging with droplet 130 to initiate the wash operation. Beads 122 are thus exposed to wash droplet 130.

Figure 3C:
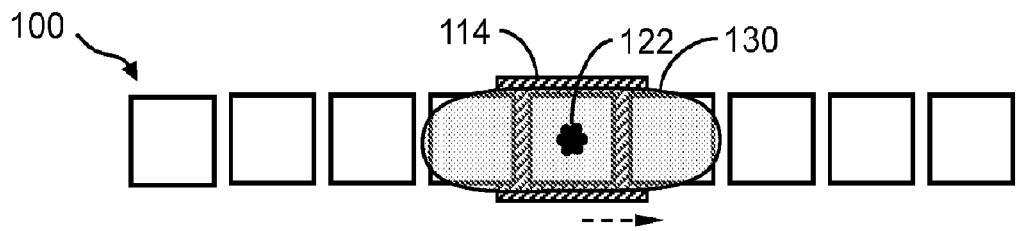
Figure 3D:
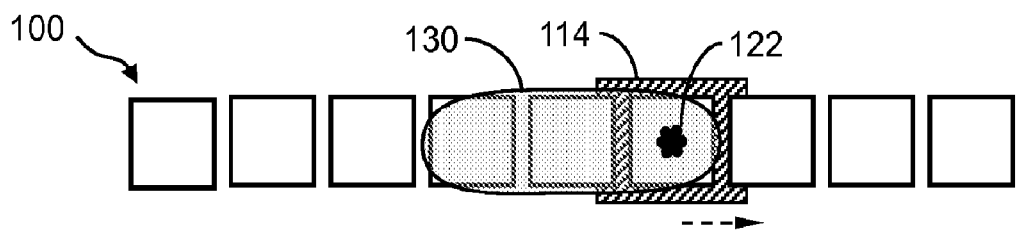

FIGS. 3C and 3D show magnet 114 moved further along electrode arrangement 100, pulling beads 122 through the length of elongated droplet 130.

Figure 3E:
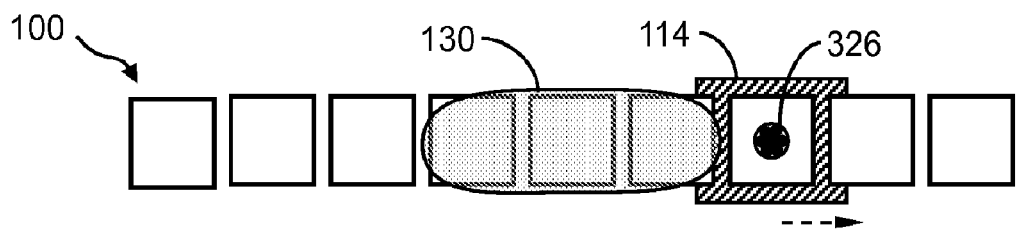
Figure 4A:
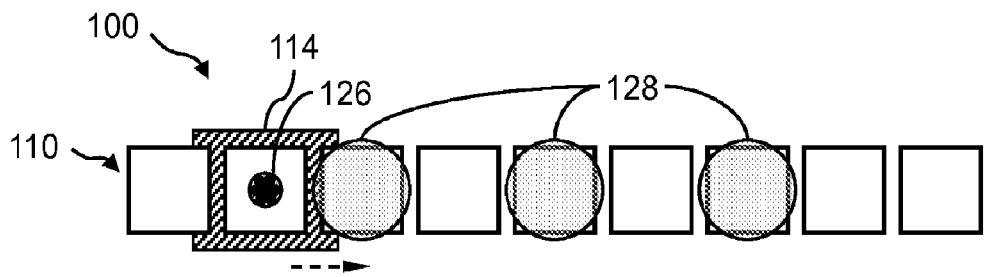
Figure 4B:
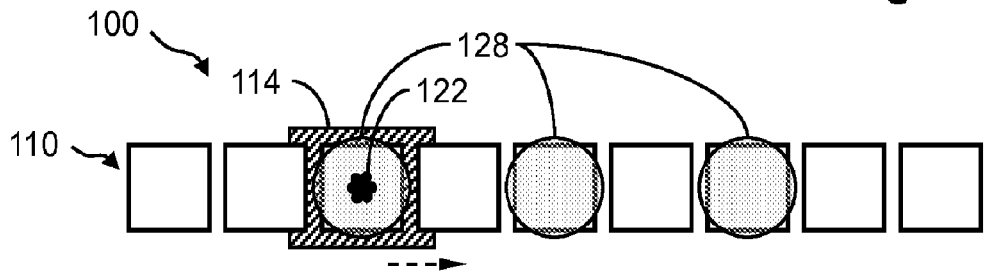
Figure 4C:
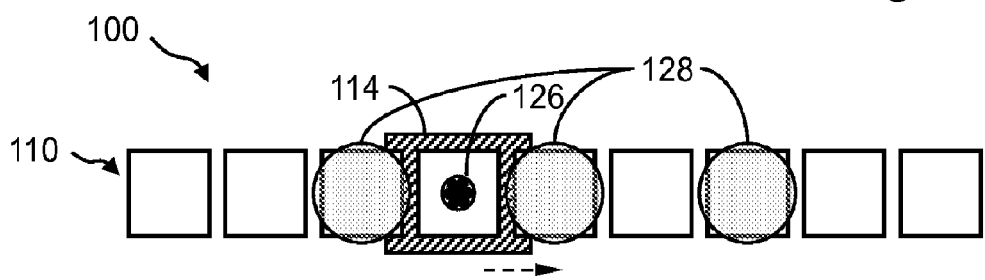
Figure 4D:
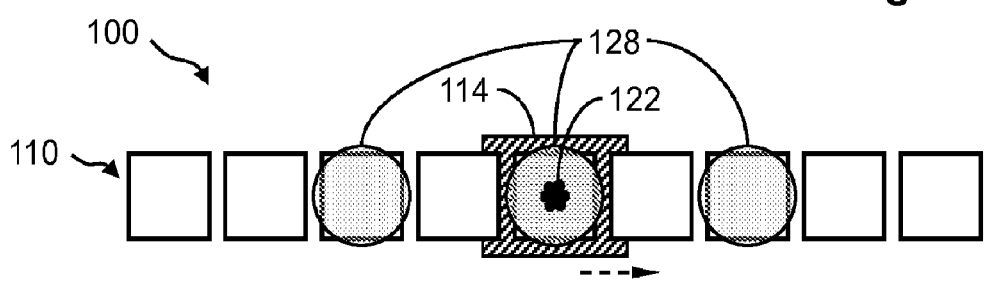
Figure 4E:
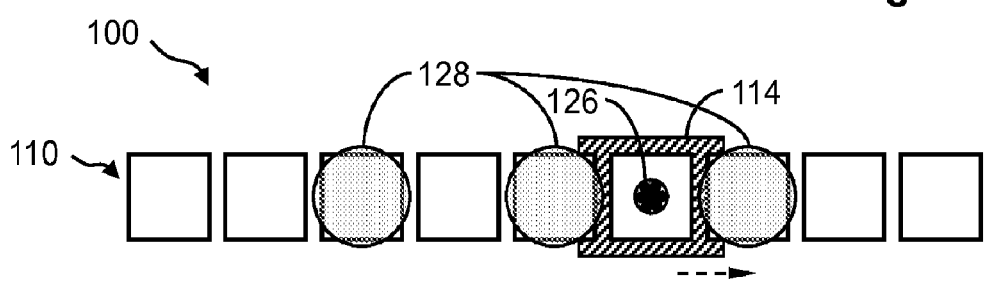

FIG. 3E shows magnet 114 moved further along electrode arrangement 100, pulling beads 122 out of droplet 130. Droplet 326 is formed including substantially all of magnetically responsive beads 122. This step illustrates how beads may be pulled out of the droplet by moving the magnet. The droplet split operation may enhanced by providing droplet 130 with an appropriate interfacial tension which allows beads 122 to be easily extracted from droplet 130 using the magnetic force of magnet 114.

In one embodiment, the method of the invention removes about 95, 96, 97, 98, 99, 99, 99.9, 99.99, 99.999, 99.9999, or 99.99999 percent of unwanted molecules in the droplet surrounding beads by use of only 10, 9, 8, 7, 6, 5, 4, 3, 2 or 1 wash droplets, where the wash droplet is a 1×, 2×, 3×, 4×, or 5× wash droplet, and a magnet is used to move the beads through the one or more wash droplets or a combination of magnet movement and wash droplet movement is used to wash the beads.

FIGS. 4A-4E illustrate a method of the invention in which the bead-containing droplets and/or wash droplets are held in a stationary position, while movable magnets are used for manipulating the beads. The steps shown in FIGS. 4A through 4E are substantially the same as those that are described in FIGS. 3A through 3E except that, instead of washing beads 122 using, for example, a 3× slug of liquid, multiple stationary 1× wash droplets are used. Droplet 130 of FIGS. 3A through 3E is replaced with multiple stationary wash droplets 128, which are low interfacial tension wash liquid, such as low interfacial tension supernatant. Magnet 114, which is holding a concentration of beads 122 or bead-containing droplet 126, may be moved in a direction which is along droplet operations electrodes 100. In doing so, a droplet merge and split operation occurs at each encounter with a wash droplet 128. With each encounter with a wash droplet 128, beads 122 experience a washing event. These droplet merge and split operations are enhanced by the low interfacial tension of each wash droplet 128, which is selected to allow beads 122 to be easily introduced into and extracted from each wash droplet 128 using the magnetic force of magnet 114. In another embodiment, both the magnet and the wash droplets can be moved in opposite directions enhancing the wash efficiency and reducing the total time for washing.

Figure 5:
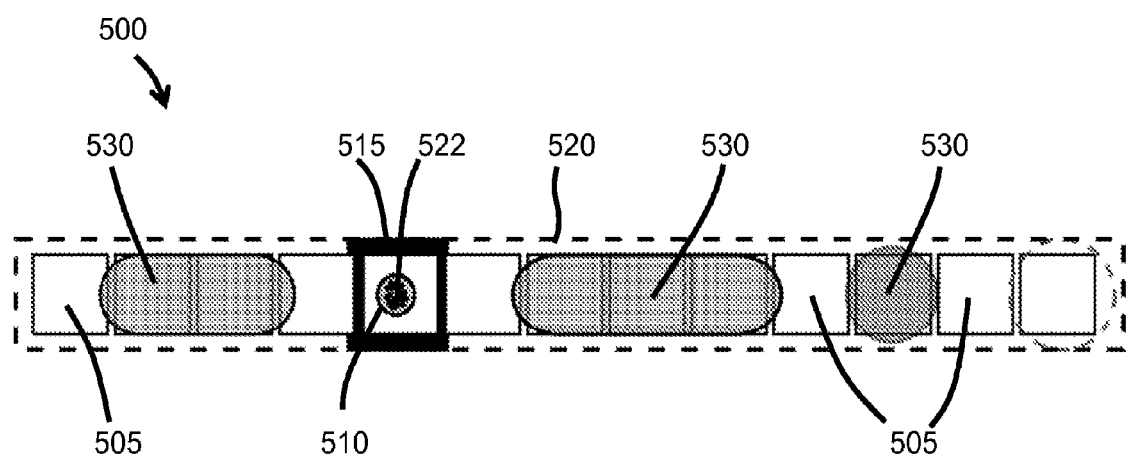
FIG. 5 illustrates an embodiment in which one or more steps of an assay may be performed by using a moving magnet or a moving droplet-containing device relative to a fixed magnet.

FIG. 5 illustrates an embodiment in which one or more steps of an assay may be performed by using a moving magnet or a moving droplet-containing device relative to a fixed magnet. In this approach, the magnetically responsive beads may be moved by a magnet through a series of droplets that include one or more sample droplets and reagent droplets in accordance with an assay protocol. The figure illustrates a configuration 500 of electrodes 505 arranged to mediate droplet operations on a droplet operations substrate of a droplet actuator. Droplet 510 including magnetically responsive beads 522 is positioned on the droplet operations surface. A magnet 515 is associated with the droplet operations substrate in a manner which enables magnet 515 to attract magnetically responsive beads 522 in droplet 515 on the droplet operations surface. Magnet 515 is moveable along a path 520. As illustrated, path 520 generally coincides with a path of electrodes 505. One or more sample and/or reagent droplets 530 are disposed atop electrodes 505 and subject to one or more droplet operations mediated by electrodes 505. In operation, magnet 515 may be moved through droplets 530 to conduct steps of an assay. Magnet 515 may, in one embodiment, be moved linearly through droplets 530 to conduct the assay. In another embodiment, magnet 515 may be moved back and forth at one or more points in the path through droplets 530, e.g., to agitate beads 522 in the sample droplet to effect greater capture of sample material, and/or in a wash droplet to increase the effectiveness of washing. As illustrated, the path through droplets 530 is one-dimensional; however, it will be appreciated that the path may be 2-dimensional or even three dimensional. In one embodiment, the path is a loop, such as a circular loop. In another embodiment, the path is a spiral. The path may or may not be aligned with a corresponding path of electrodes. In one embodiment, for example, the path intersects multiple electrode paths but does not itself follow an electrode path. Electrode configuration 500 may be part of a larger electrode configuration on a droplet actuator, which may be used to position droplets using electrode-mediated droplet operations.

As an example of an immunoassay may be performed in which beads are pulled using a magnet through multiple droplets is an immunoassay. In one non-limiting example, the immunoassay may be a sandwich ELISA, in which a magnet is used to pull a droplet through a series of droplets as follows:
  one or more sample droplets to capture the target substance,
  or more wash droplets to remove unbound substances,
  one or more droplets including primary antibodies that bind specifically to the target substance,
  one or more droplets including enzyme-linked secondary antibodies specific to the primary antibodies,
  one or more droplets that include the chemical which is converted by the enzyme to produce a signal, such as a fluorescent, luminescent or electrochemical signal.

In a similar embodiment, the interfacial tension of the droplet, bead properties and concentration are adjusted to permit an immunoassay to be performed using gravity to pull beads through the droplets. In this embodiment, reagents may be provided in a tube or column separated by an immiscible liquid. A sample may be injected into the top of the tube. Beads may be added to the sample and permitted to settle, dropping through the sample and the various reagent droplet. A signal from the beads may be detected. The beads may be made of a dense material, such as copper, lead or another heavy metal.

Figure 6:
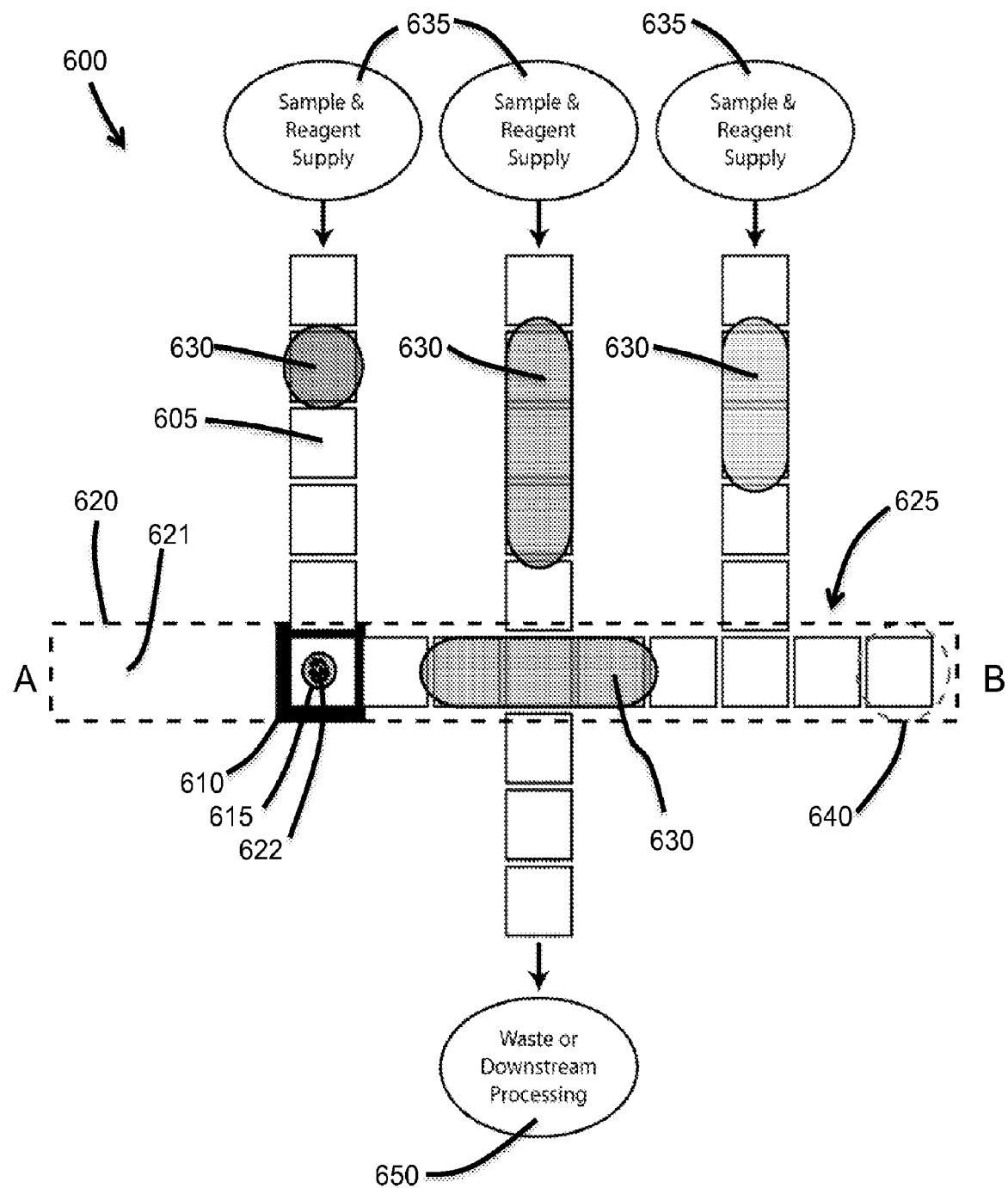
FIG. 6 illustrates an embodiment in which a magnet may be moved back and forth along a path, and droplet operations may be used to position one or more new droplets along the magnet's path between each instance in which the magnet is moved across the magnet path.

FIG. 6 illustrates an embodiment that is similar to the embodiment illustrated in FIG. 5. In the FIG. 5 embodiment, the magnetically responsive beads may be moved by a magnet through a series of droplets positioned on a droplet actuator surface along a path that corresponds with the path of a magnet; in the FIG. 6 embodiment, the magnet may be moved back and forth along a path, and droplet operations may be used to position one or more new droplets along the magnet's path between each instance in which the magnet is moved across the magnet path. It will be appreciated that in various alternative embodiments, the magnet may be moved along paths that do not follow electrode paths, e.g., the magnet may move along a path that intersects one or more electrode paths and/or travels along segments of one or more electrode paths.

As illustrated, a configuration 600 of electrodes 605 arranged to mediate droplet operations on a droplet operations substrate of a droplet actuator. Droplet 615 including magnetically responsive beads 622 is positioned on the droplet operations surface. A magnet 610 is associated with the droplet operations substrate in a manner which enables magnet 610 to attract magnetically responsive beads 622 in droplet 615 on the droplet operations surface. Magnet 610 is moveable along a path 620. As illustrated, path 620 generally coincides with an electrode path 625. A region 621 of path 620 is outside the path of electrodes. Region 621 may be configured to permit magnet 610 to be moved a sufficient distance from path 625 and nearby electrodes so that one or more magnetically responsive bead-containing droplets may be transported on path 625 and nearby electrodes without undue interference from magnet 610. Electrode configuration 600 is associated with one or more sample & reagent supplies 635, such as on-actuator or off-actuator liquid reservoirs. Droplets 630 may be dispensed from sample and reagent supplies 635 and transported using droplet operations onto electrode path 625, which is in the path 620 of magnet 610. A detection window 640 or other detector may be provided for detection of a signal from or property of a droplet on the droplet actuator.

In operation, one or more first droplets 630 may be transported using droplet operations onto electrode path 625. Magnet 610 may be moved along path 620 in an A-to-B direction through the one or more first droplets 630 to effect a first step in an assay. First droplets 630 may be removed from path 625 and transported using one or more droplet operations to waste or to downstream processing. One or more second droplets 630 may be transported using droplet operations onto electrode path 625. Magnet 610 may be moved along path 620 in a B-to-A direction through the one or more second droplets 630 to effect a second step in an assay. Second droplets 630 may be removed from path 625 and transported using one or more droplet operations to waste or to downstream processing 650. This process may be repeated until the assay is complete. A droplet emitting a detectable sample may be transported into detection window 640 and/or into contact with or proximity to a sensor using magnet 610 and/or using droplet operations. A sensor may be used to sense one or more properties of the droplet, and results of the sensing may be used to provide assay results. In one embodiment, a detection droplet including a detection reagent is positioned using a magnetic field in a detection window, and beads ready for detection are moved into the detection window and into the detection droplet. Following detection, the detection droplet may be transported via droplet operations mediated by the electrodes to waste or further downstream processing.

In another similar embodiment, a mixture of magnetic beads each labeled with different target antibodies specific to a particular analyte can be moved through several sample droplets to effectively bind the analytes to the target antibodies. Incubation can be improved by shuttling the mixture of magnetic beads through the sample droplets several times in order to ensure that all the analyte is captured. The sample may, for example, be a single large slug spanning several electrodes or several unit sized droplets. In another similar embodiment, different sets of magnetic beads each labeled with a set of target antibodies specific to a particular analyte are immobilized at different electrodes on the droplet actuator which are held stationary. A sample droplet containing a mixture of "n" analytes is passed through the droplets containing different bead sets. The supernatant from the first bead set would contain "n minus 1" analytes which is the sample droplet for the second bead set. Similarly the supernatant from the second bead set would have "n minus 2" analytes and so on.

Figure 7A:
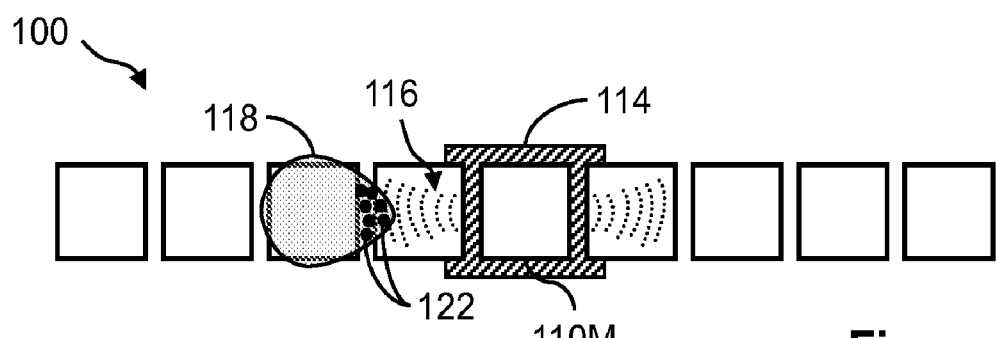
FIGS. 7A and 7B illustrate top views of an example of a portion of a droplet actuator and show a method of separating beads when both the magnet and droplet are stationary.
Figure 7B:
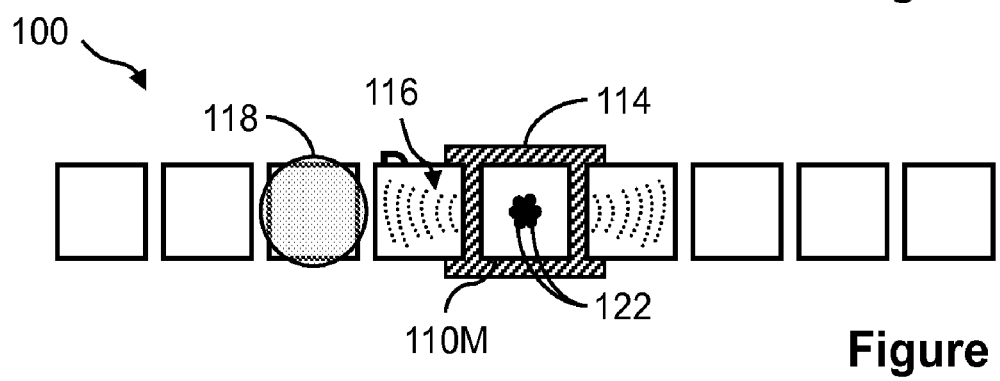

FIGS. 7A and 7B illustrate top views of an electrode arrangement 100 on a droplet actuator and demonstrate another method of removing beads from a droplet. In this embodiment, the interfacial tension of bead-containing droplet 118, magnetic bead 122 properties and concentration, and pull force of magnet 114 exerted on magnetically responsive beads 122 are selected to cause beads 122 to be pulled out of droplet 118 as droplet 118 approaches magnet 114. FIG. 7A shows that as droplet 118 is transported using droplet operations along electrode arrangement 100 into proximity with magnet 114, magnetically responsive beads are attracted by the magnetic field of magnet 110. FIG. 7B shows droplet 118 substantially lacking in magnetically responsive beads 122, which have been pulled out of droplet 118 and are resting atop magnet 114.

As with other examples using magnets described herein, magnet 114 may be a permanent magnet, an electromagnet, or any other magnetic field generating substance or device. An electromagnet may be activated to pull beads 122 out of droplet 118. A permanent magnet may pull beads beads 122 out of droplet 118 when the droplet and permanent magnet are moved into sufficient proximity with one another, by moving the droplet, the permanent magnet, or both.

In another embodiment, a droplet is provided with magnetically responsive beads in the presence of a magnetic field. The droplet has sufficiently high interfacial tension to retain the beads in the droplet. In other words, the bead-retaining force of the interfacial tension is greater than the bead-attracting force of the magnet on the beads, thereby retaining the beads in the droplet. A low interfacial tension droplet may be merged with the bead-containing droplet, causing the interfacial tension of the bead-containing droplet to decrease to a point at which the bead-retaining force of the interfacial tension is less than the bead-attracting force of the magnet on the beads, thereby causing the beads to break away from the droplet. In another embodiment, the temperature of the droplet can be increased which further reduces the interfacial tension of the droplet facilitating snapping off the beads from the droplet as the droplet is brought in the vicinity of the magnetic field. In another embodiment, the magnet could be a stationary electromagnet, and the magnetic field could be dynamically varied to ensure the snapping of the magnetic beads.

6.2 Re-Suspending Beads

FIGS. 8A-8D illustrate top views of an electrode arrangement 100 on a droplet actuator and demonstrate a method of re-suspending beads into solution from a stationary magnet. In this embodiment, the interfacial tension of droplet 810, magnetic bead 122 properties and concentration, and pull force of magnet 114 exerted on magnetically responsive beads 122 are selected to permit droplet 810 to merge with bead-containing droplet 126 and pull beads 122 away from magnet 114. The parameters are adjusted so that the interfacial tension of droplet 812 is greater than the bead-attracting force of magnet 114 on beads 122 retaining the magnetic beads within the droplet.

Figure 8A:
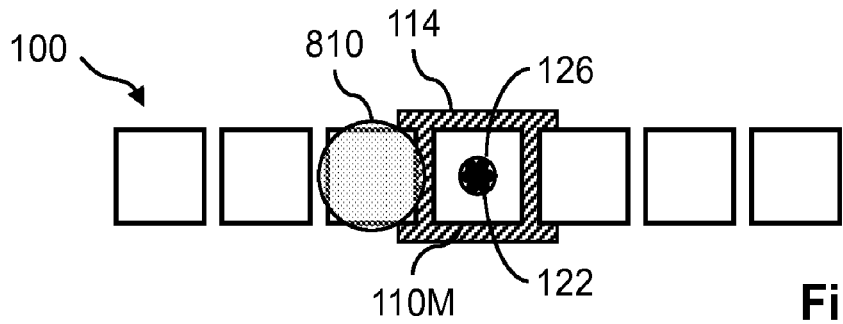
Figure 8B:
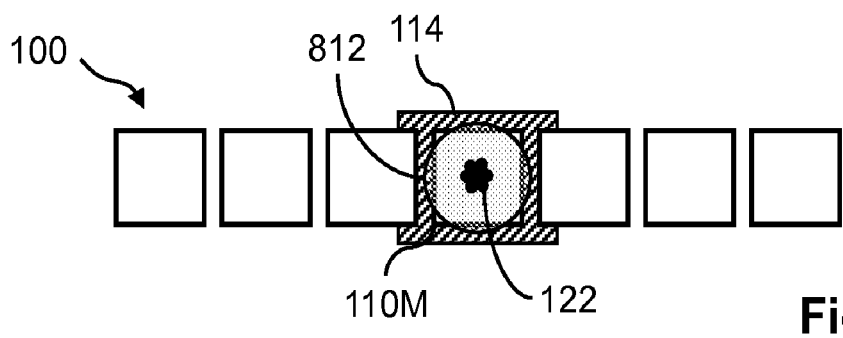
Figure 8C:
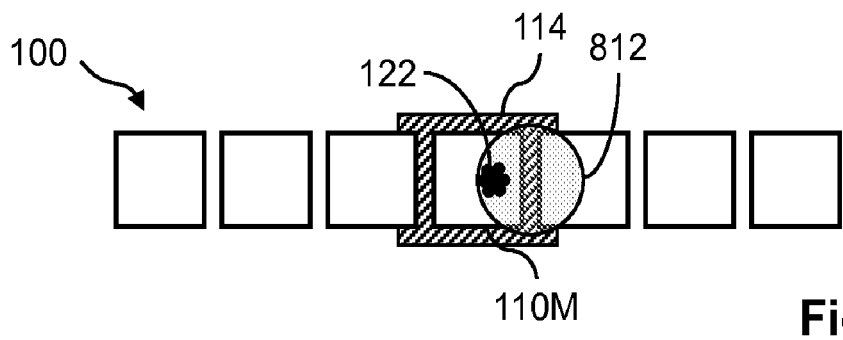
Figure 8D:
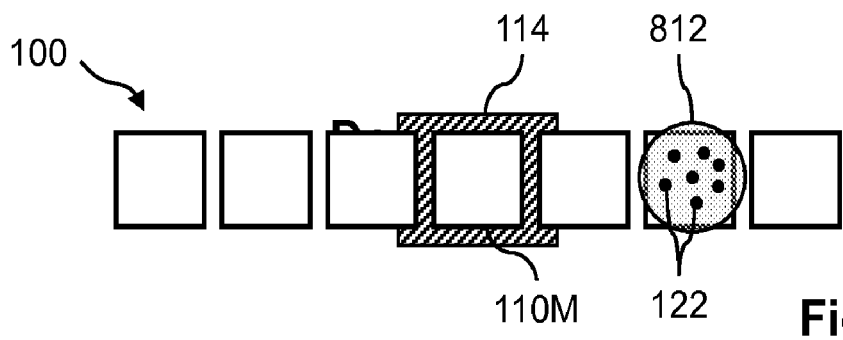

FIG. 8A shows droplet 810 positioned on electrode arrangement 100 and a bead-containing droplet 126 positioned atop electrode 110M. Bead-containing droplet 126 is retained in position by electrowetting or any other means, while the beads are immobilized by the magnetic field of magnet 114. FIG. 8B shows droplet 810 transported via droplet operations mediated by electrodes of electrode configuration 110 into contact with and merged with bead-containing droplet 126 yielding merged droplet 812. FIG. 8C shows droplet 812 being transported using droplet operations away from electrode 110M. Because droplet 810 is formed of a relatively high interfacial tension liquid, the interfacial tension of droplet 812 overcomes the pull on beads 122 of the magnetic field, permitting beads 122 to be transported away from magnet 114. FIG. 8D shows droplet 812 with beads 122 transported away from electrode 110M.

In general, the following parameters may be adjusted so that transport of a magnetically responsive bead-containing droplet away from the magnetic field will move the magnetically responsive beads away from the magnetic field: interfacial tension of the droplet, magnetic bead properties and concentration, and pull force of the magnet exerted on the magnetically responsive beads. For example, the surfactant may be Tween 20, and the concentration of Tween 20 may greater than about 0.02%. Of course, the required concentration will vary depending on the surfactant type. The desired interfacial tension range may be greater than about 4 dynes/cm. The magnetic bead concentration range is typically from about 10 mg/mL to about 30 mg/mL. Pull force of the magnet may typically range from about 5 lbs to about 100 lbs. In one embodiment, the buffer may include 0.05M Tris HCl, 0.1M NaCl, 0.1 mg/mL BSA and about 0.02% Tween 20.

FIGS. 9A-9C illustrate side views of a section 900 of a droplet actuator. Section 900 shows bottom substrate 910 separated from a top substrate 914 by droplet operations gap 918. Magnet 114 is associated with bottom substrate 910. In FIG. 9A, droplet 930 is positioned in droplet operations gap 918 atop an electrode of electrode arrangement 922, and a bead-containing droplet 126 including beads 122 is positioned atop another one of the electrodes of electrode arrangement 922. Droplet 126 has a footprint which is smaller than the footprint of the underlying electrode, and is held in place by the magnetic attraction of magnet 114 for beads 122. In FIG. 9B, droplet 930 has been transported into contact with and merged with droplet 126 to form merged droplet 931, and magnet 114 is being moved away from magnetically responsive beads 122 to release magnetically responsive beads 122 from the magnetic field. FIG. 9C shows beads 122 resuspended in droplet 931 and transported along electrode path 922.

In another embodiment, a change in magnetic field gradient may be provided at droplet operations electrode 922M by tilting magnet 114. In yet another embodiment, magnet 114 may be a stationary electromagnet that may be turned off and on for controlling the amount of magnetic force that is present at droplet operations electrode 922M. In yet another embodiment, a moveable magnetic shield may be interposed between magnet 114 and beads 122 to release beads 122 into droplet 931.

FIGS. 10A-10D illustrate side views of a section 1000 of a droplet actuator and a method of removing beads from a droplet actuator gap 1018 of the droplet actuator. Section 1000 includes bottom substrate 1010 separated from top substrate 1014 by droplet operations gap 1018. An electrode arrangement 1026 is associated with bottom substrate 1010 and configured to mediate droplet operations in droplet operations gap 1018. Reservoir electrode 1022 is included in electrode arrangement 1026. As with other examples described herein employing two substrates separated to form a droplet operations gap, the electrode arrangement may include any arrangement suitable for conducting droplet operations in the droplet operations gap, e.g., electrodes associated with the top substrate, the bottom substrate, between the substrates, and combinations of the foregoing. Further, as with other embodiments making use of a droplet operations gap, the gap may be partially or completely filled with a filler fluid that is substantially immiscible with droplets subject to droplet operations in the gap. In the embodiment illustrated here, top substrate 1014 includes an opening 1040 providing a liquid path from within droplet operations gap 1018 to a locus which is exterior to droplet operations gap 1018. Section 1000 also shows a quantity of droplet 1030 atop reservoir electrode 1022, exposed to or extending into opening 1040.

In the non-limiting example illustrated, opening 1040 is located across droplet operations gap from reservoir electrode 1022. Opening 1040 may be generally centrally aligned with electrode 1022. Electrode 1022 may, when activated, determine the approximate footprint of droplet 1030. Opening 1040 may be arranged relative to the approximate footprint of droplet 1030 to provide a relatively direct path to magnet 114 from any location within droplet 1030. The dimensions of opening 1040 may be modified to facilitate movement of beads from any location within droplet 1030 to magnet 114. For example, opening 1040 may have the shape of a cross-section of an inverted cone. Moreover, in various embodiments, two or more openings 1030 may be provided in substrate 1014. In one example, the openings are arranged in the footprint of a multiwall plate. Corresponding magnets or magnetic field generating configurations may also be provided.

Figure 10A:
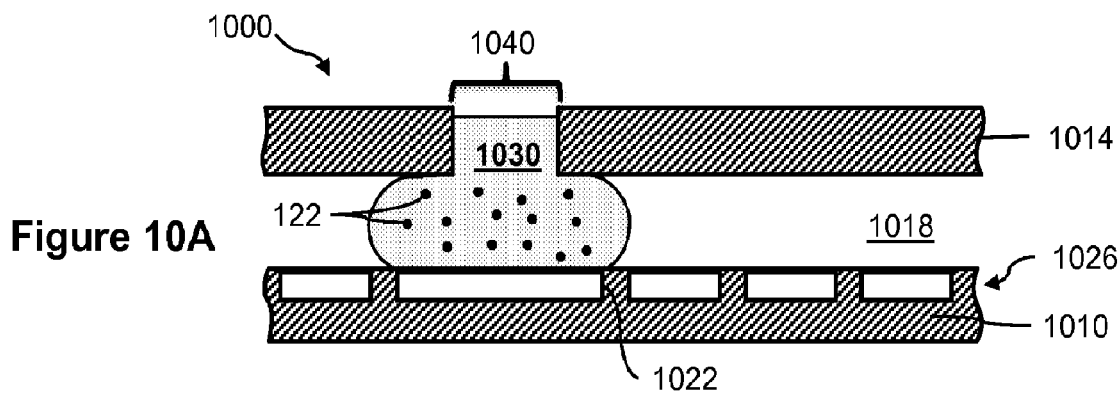
Figure 10B:
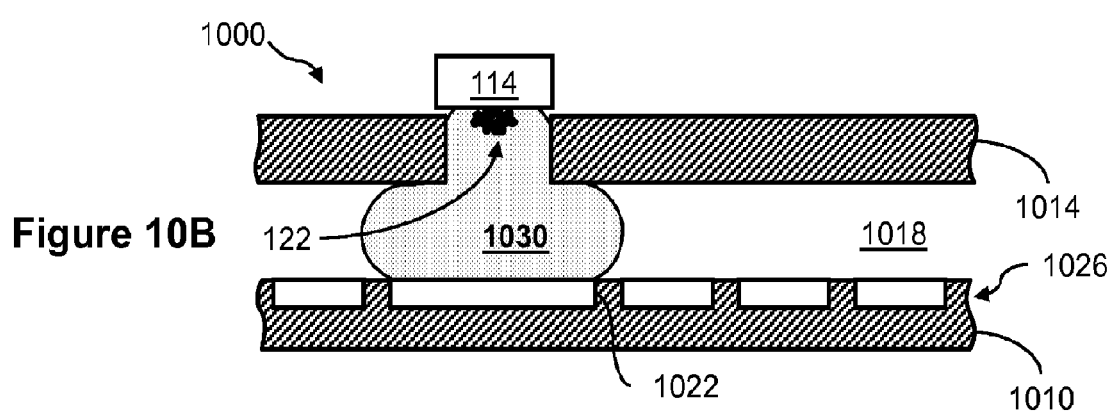
Figure 10C:
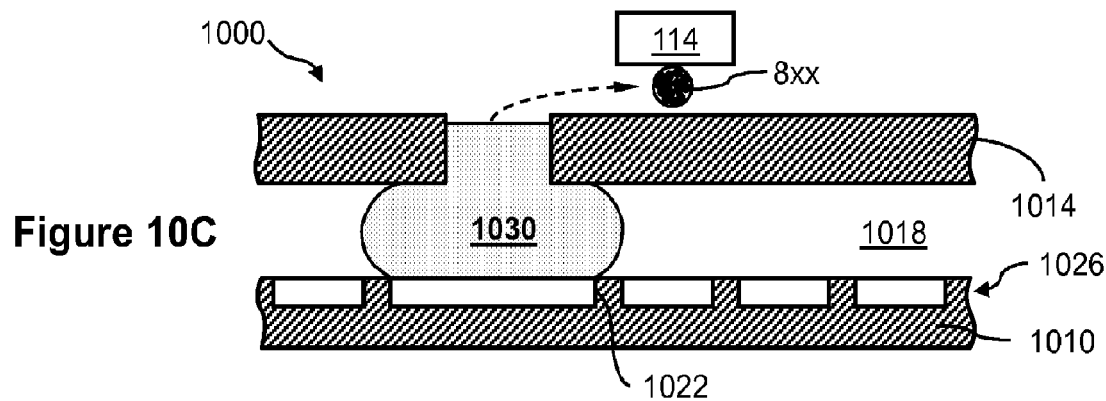

As illustrated, magnet 114 is movable relative to the opening in top substrate 1014. Magnet 114 may, for example, be robotically controlled. In one embodiment, magnet 114 is an electromagnet, so that its magnetic force may be turned off and on. Pollack et al., International Patent App. No. PCT/US09/36449, entitled "Reagent and Sample Preparation and Loading on a Fluidic Device," filed on Mar. 9, 2009, incorporated herein by reference, describes certain magnetic devices and droplet actuators suitable for execution of the methods described herein. In operation, magnet 114 may be used to remove magnetically responsive beads from and/or introduce magnetically responsive beads into a droplet actuator using a movable magnet, e.g., using the following steps:

FIG. 10A illustrates beads 122 in the absence of a magnetic field are suspended within droplet 1030 at electrode 1022. FIG. 10B shows magnet 114 placed in sufficient proximity to the opening 1040 in top substrate 1014 to cause beads 122 within droplet 1030 to be attracted to magnet 114. A concentration of beads 122 is formed on magnet 114 at the opening in top substrate 1014. FIG. 10C shows magnet 114, which is still activated, moved away from the opening in top substrate 1014. Beads 122 are lifted out of droplet 1030, usually surrounded by some residual liquid, and carried away by magnet 114. In this manner, beads 122 may be removed from droplet actuator. The interfacial tension of droplet 1030 may, in some cases, be adjusted to a interfacial tension that permits beads 122 to be easily extracted from droplet 1030 with minimal loss of liquid from droplet 1030. In one embodiment, the droplet actuator is used to prepare beads for analysis, e.g., by conducting one or more steps of a sample preparation protocol and/or an immunoassay, and beads are removed as described here and deposited in another instrument to complete the analysis.

Figure 10D:
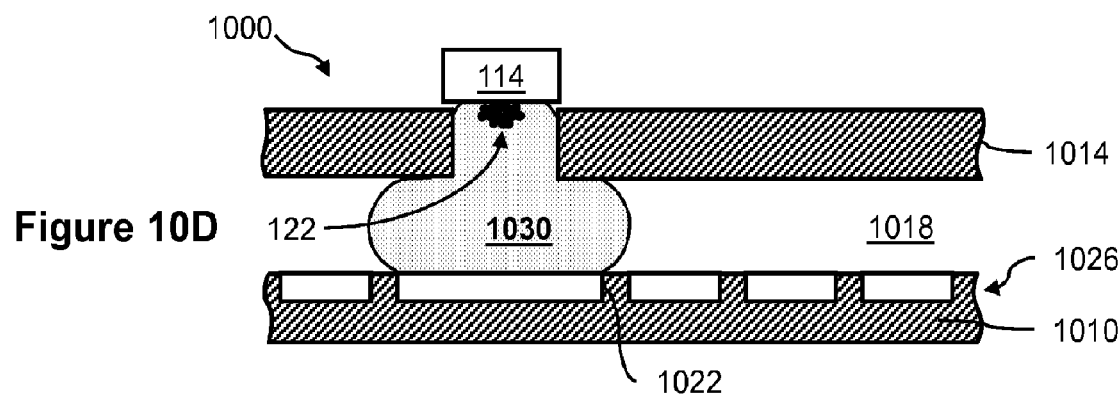

FIG. 10D shows placement of beads 122 into opening 1040 so that the beads may be released into droplet 1030 in droplet actuator gap 1018. Magnet 114, which is still activated, is repositioned in close proximity to the opening in top substrate 1014 (which may be the same opening from which the beads are extracted or a different opening). Beads 122 that are concentrated on the surface of magnet 114 are brought into contact with droplet 1030. Subsequently, magnet 114 may be deactivated, thereby releasing beads 122 into droplet 1030.

Alternatively, beads 122 may be introduced into another region of droplet operations gap 1018, into another reservoir in fluid communication with droplet operations gap 1018, into a reservoir or droplet operations gap of another droplet actuator, or into another analytical or bead-handling handing device altogether. The introduction of beads 122 into droplet 1030 is enhanced by selecting a relatively low interfacial tension for droplet 1030, allowing beads 122 to be easily introduced. When introducing beads from a magnet which is not an electromagnet, it may be helpful to increase the interfacial tension of the droplet into which the beads are introduced in order to permit the interfacial tension of the droplet to overcome the forces of the magnet thereby retaining the beads in the droplet when the magnet is moved away.

In another embodiment, a droplet containing magnetically responsive beads can be transported to an electrode which is aligned with an opening in the top substrate. A droplet at the electrode may be fluidly connected to an off-actuator reservoir including a large volume of wash buffer. In this manner, the beads may be effectively contacted with a large volume of wash buffer. The unbound materials may thus be instantly diluted by several orders of magnitude. The electrode may be repeatedly activated and deactivated to mix the beads with liquid in the reservoir, thereby enhancing dilution and washing. In this and other embodiments in which there are openings in the top substrate leading to external reservoirs, the openings may be arrayed in a typical multi-well plate pattern, such as a 96-well, 384-well or a 1536-well plate pitch.

In another embodiment, the magnetically responsive beads may be extracted from a droplet actuator and transported to another droplet actuator using a moving magnet. The droplet actuator may have a droplet operations gap which is at least partially filled with filler fluid. The magnetic beads may be placed in an opening in the top plate using the moving magnet. The magnetically responsive beads may be resuspended using a buffer, such as a wash buffer. The magnetically responsive beads may be dispensed in droplets using electrode mediated droplet operations, such as electrowetting or dielectrophoresis mediated droplet operations. This technique may be useful for processing large numbers of samples, such as physiological fluids, where the analyte of interest may be captured from a large volume onto the surface of magnetic beads. The magnetic beads with the analyte of interest can be transferred into another droplet actuator using the process. The magnetic beads with the analyte of interest can be subjected to further analysis in the second droplet actuator.

In another similar embodiment, different sets of magnetic beads immobilized at different locations in a droplet actuator can be stamped or otherwise deposited into wells of a multi-well plate through openings in the top plate which coincide with the wells in the multi-well plate. The multi-well plate with magnetic beads in different wells can be used for further processing. Magnetic bead content, magnetic bead properties, interfacial tension and magnetic pull force, and/or properties of the surface of the multi-well plate may be adjusted as needed to achieve the stamping or deposition.

6.3 Bead Separation

One approach to multiplexing assays, such as immunoassays, within a single droplet involves the use of multiple different types of beads within the same droplet. For example, different types of beads may be coated with different antibodies or different analytes. The mixture of beads may, for example, include magnetic/non magnetic, charged/uncharged, heavy/light, or dense or buoyant beads. During assay protocols, it may be useful to separate such beads. For example, in an immunoassay, following the binding of the antibodies and antigens to beads, each type of bead may be separated from the mixture. In one embodiment, separation is achieved by using a combination of effects.

Magnetically responsive beads can be immobilized or trapped using a magnetic field, while magnetically non-responsive beads are transported away in the droplet or split off from a parent droplet to yield a sub-droplet including the magnetically responsive beads and a droplet including the magnetically non-responsive beads. In one embodiment, a parent droplet including magnetically responsive beads is provided in the presence of a magnetic field, the parent droplet also including beads that are substantially non-responsive to a magnetic field. The magnetic field immobilizes the magnetically responsive beads. The droplet is elongated and split to yield two or more daughter droplets, one set of one or more daughter droplets including substantially all of the magnetic beads, and another set of one or more daughter droplets including magnetically non-responsive beads and substantially lacking magnetically responsive beads.

Magnetically non-responsive beads can be retained using a physical barrier within the droplet actuator arranged to retain beads while a droplet is transported past the barrier, e.g., as described in Thwar, et al., International Patent Pub. No. WO2009/029561, entitled "Bead Manipulations on a Droplet Actuator," published on Mar. 5, 2009, the entire disclosure of which is incorporated herein by reference.

Dense beads can be separated as described with reference to FIG. 23. For example, they can be regionalized within the droplet by positioning the droplet actuator a slight angle relative to gravitational force or even by placing the droplet actuator in a substantially vertical position, as described above.

Buoyant beads can be separated as described with reference to FIG. 24. Further, they can be floated away, e.g., by transporting the droplet to an opening in the top substrate, and permitting the buoyant beads to float through the opening, e.g., into a liquid in a reservoir in liquid communication with the droplet via a vertical opening through which the beads can pass as they float to a surface of the liquid. Thereafter, the droplet can be transported away without the buoyant beads. The buoyant beads can then be brought reintroduced onto the droplet actuator.

Charged and uncharged beads can be separated by using electrophoretic and dielectrophoretic separation mechanisms.

Beads may have multiple properties as well. For example, buoyant beads and dense beads may also be magnetically responsive. Such beads may, for example, be separated as described above, then washed using a split-and-merge wash protocol in which the magnetically responsive beads are restrained in place by a magnetic field.

FIGS. 11A-11D are illustrative of a method of separating magnetically responsive beads from non-magnetically responsive beads by (1) chemically aggregating the non-magnetically responsive beads; and (2) aggregating the magnetically responsive beads using magnetic forces. The figures show top views of an electrode arrangement 100 on a droplet actuator. The figures illustrate a method of bead separation by chemical modification. Magnet 114 is positioned at a certain droplet operations electrode 110 of droplet actuator, such as at droplet operations electrode 110M. In this embodiment, magnet 114 may be an electromagnet and, therefore, its magnetic force may be turned off and on.

Bead-containing droplet 1110 is provided atop an electrode of electrode arrangement 100. Bead-containing droplet 1110 includes magnetically non-responsive beads 1114 and magnetically responsive beads 1116. Magnetically non-responsive beads 1114 may be charged and, hence, are dispersed within droplet 1110.

Droplet 1118 is provided atop an electrode of electrode arrangement 100. Droplet 1118 includes substances that may render a chemical change that is designed to affect certain beads within droplet 1110. For example, droplet 1118 may include substances that bind to beads 1114 and/or beads 1116. In one embodiment, a first substance binds beads 1114 and a second substance binds to beads 1116. In this manner, the method of the invention can be used to separate the two substances. In another example, droplet 1118 induces a chemical change, such as a pH change that causes magnetically non-responsive beads 1114 to clump within droplet 1110. In another example, clumping is induced after magnetically non-responsive beads are separated from the magnetically responsive beads. An example of a method of bead separation by chemical modification may include, but is not limited to, the following steps.

Figure 11A:
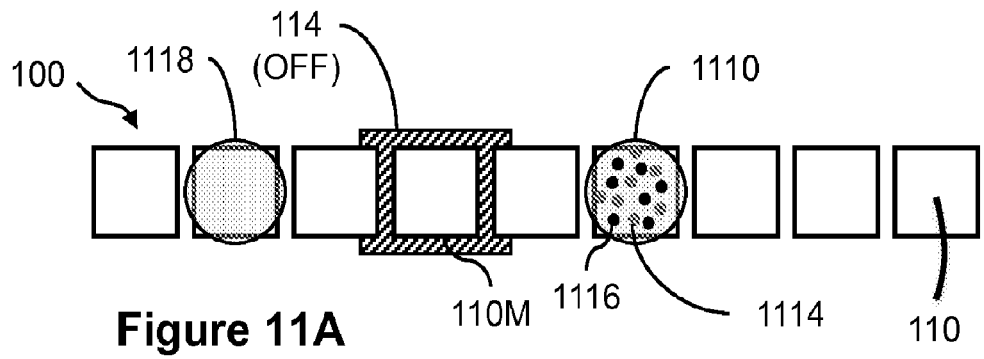

FIG. 11A shows droplet 1110 positioned using droplet operations at certain droplet operations electrode 110. Droplet 1118 is positioned using droplet operations at certain droplet operations electrode 110. Magnet 114 at droplet operations electrode 110M is deactivated and, therefore, no magnetic force is present at droplet operations electrode 110M.

Figure 11B:
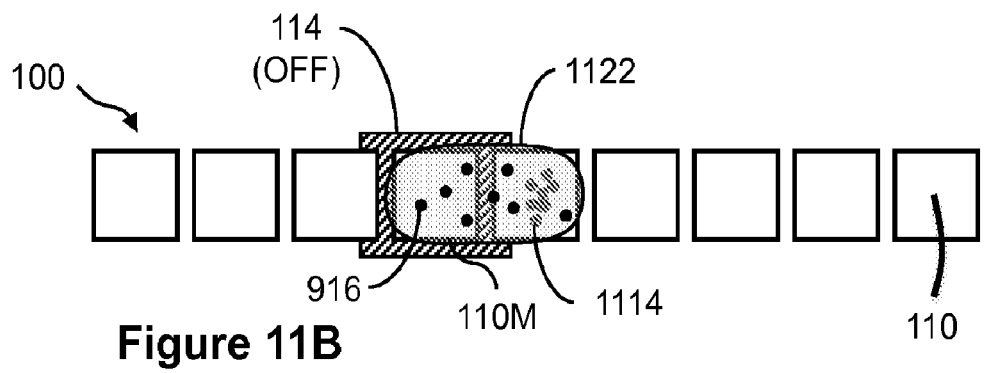

FIG. 11B shows droplet 1110 and chemical change droplet 1118 merged at droplet operations electrode 110M. Magnet 114 remains deactivated. As illustrated, a 2× droplet 1122 is formed across droplet operations electrode 110M and an immediately adjacent droplet operations electrode 110. 2× droplet 1122 is a mixture of the liquid that forms both droplet 1110 and chemical change droplet 1118. Of course, the merging may take place elsewhere and the combined droplet may be transported into the presence of magnet 114. As a result of mixing droplet 1110 and chemical change droplet 1118, a pH change occurs on magnetically non-responsive beads 1114 that are now within 2× droplet 1122. The result of this pH change may cause magnetically non-responsive beads 1114 to lose their charge. This loss of charge may cause magnetically non-responsive beads 1114 to form a concentrated clump within 2× droplet 1122. By contrast, magnetically responsive beads 1116 are substantially unaffected by the mixing of droplet 1110 and chemical change droplet 1118 and are freely suspended in 2× droplet 1122.

Figure 11C:
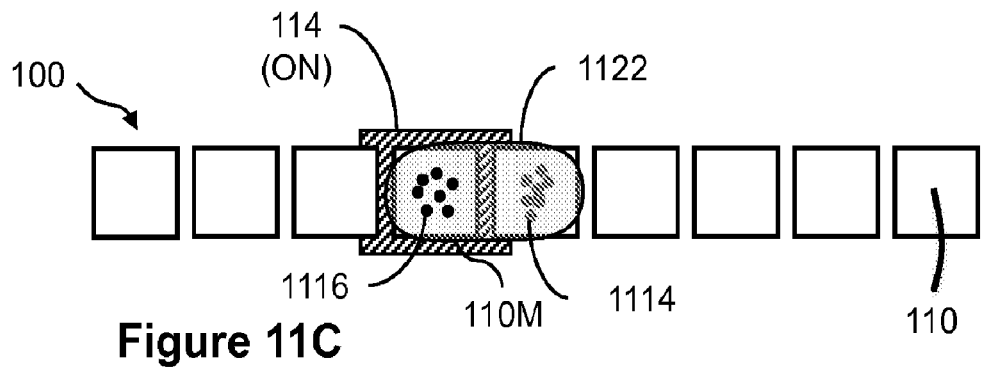

FIG. 11C shows magnet 114 activated and, therefore, generating a magnetic force that immobilizes magnetically responsive beads 1116 and concentrates them in a centralized region of droplet operations electrode 110M. The magnetic force of magnet 114 has substantially no effect on the clump of magnetically non-responsive beads 1114 at, for example, the droplet operations electrode 110 that is immediately adjacent to droplet operations electrode 110M.

Figure 11D:
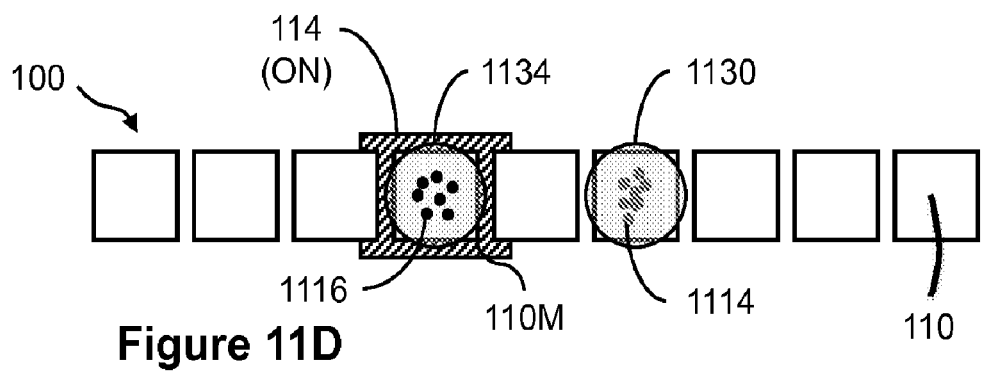

FIG. 11D shows yet another step in the method of bead separation by chemical modification. At this step, magnet 114 remains activated and a droplet split operation occurs on 2× droplet 1122. During the droplet split operation, magnetically responsive beads 1116 remain immobilized at droplet operations electrode 110M. As a result, a droplet 1130 is formed that includes mostly magnetically non-responsive beads 1114, and droplet 1134 is formed that includes mostly magnetically responsive beads 1116.

In another embodiment, magnet 114 may be a movable permanent magnet and its magnetic field strength relative to, for example, droplet operations electrode 110M of droplet actuator may be adjusted by adjusting the physical position of magnet 114 relative to droplet actuator. In another embodiment, magnetically non-responsive beads may be washed away from the immobilized magnetically responsive beads prior to causing clumping of the magnetically non-responsive beads.

6.4 Electrode with Recessed Areas for Bead Immobilization

FIGS. 12A and 12B illustrate a region/cross-section of droplet actuator substrate 1200 that has recessed areas, illustrated here as divots 1210, on the droplet operations surface 1205 for capturing beads (not shown). FIG. 12A is a top view, and FIG. 12B is a cross-section along the line XY. Droplet operations surface 1205 includes an array of divots 1210 substantially aligned with an electrode 1215 underneath the droplet actuator surface. The divots may, for example, be divots in a dielectric layer 1207 atop electrode 1215. Dielectric layer 1207 may be hydrophobic, or may be coated or otherwise treated to render it hydrophobic. The array may be in any pattern, e.g., checkerboard, star shaped, circular, linear, etc.

FIG. 13 is illustrative of embodiments in which a surface 1212 of divots 1210 includes a substance that has an affinity for bead 1325. In the example illustrated, surface 1212 includes streptavadin while the bead 1325 includes biotin. In operation, the biotin binds to the streptavadin, causing bead 1325 to bind to surface 1212. Further, different regions of the array of divots 1210 may include binding substances for binding to different bead-types, with the result that the beads may be sorted and arranged by category. Similarly, different electrodes may include binding substances for binding to different bead-types, with the result that the beads may be sorted and arranged by category. A droplet with multiple bead types may be transported using droplet operations to a first electrode where a first bead-type is captured, then to a second electrode where a second bead-type is captured. The categories may, for example, be an analyte category or a signal category.

FIGS. 14A and 14B illustrate a top view and side view, respectively, of the droplet actuator substrate 1200 that has beads 1325 arrayed in divots 1210.

FIG. 15 illustrates steps A, B and C of a method of arraying beads on a surface of a droplet actuator. In the manner illustrated, beads may be arrayed in divots on a surface of a droplet actuator using various droplet operations. Droplet 1505, droplet 1510, and droplet 1515 are arranged on a path of electrodes 1530. In Step A, droplet 1505 that contains beads 1325 is transported on the droplet actuator electrodes 1530. In Step B, droplet 1505 that contains beads 1325 is transported onto a region of the droplet operations surface 1205 that includes divots 1210 that are configured for accepting beads 1325. Surface 1205 includes an array of binding locations, each binding location having a substance with affinity for the beads. As beads contact the binding locations, they are immobilized. Droplet 1510 may be agitated, e.g., by activating and deactivating the underlying electrode at an appropriate frequency, in order to cause the beads to move around within the droplet until they are substantially all arrayed on the surface. Another example of agitating the droplet involves moving the droplet back and forth over the electrode, e.g., by transporting the droplet between the electrode and one or more adjacent electrodes. The result is illustrated as droplet 1510 associated with an arrayed set of beads 1325. In Step C, the droplet 1515, which substantially lacks beads or, alternatively, contains beads to be arrayed at another location, may in some cases be transported away from the beads that are in droplet 1510.

FIG. 16 illustrates an arrangement 1600 of electrodes 1605, including certain electrodes 1610 that have surface divots 1210 for immobilizing beads. In operation, multiple droplets, each including one or more beads, may be transported using droplet operations to a position which is atop one or more electrodes 1610 where the beads may be immobilized or captured in divots 1210.

FIG. 17 illustrates an embodiment in which a magnet 1710 is used in combination with magnetically responsive beads 1705 in order to settle magnetically responsive beads 1705 into divots 1210. Beads 1705 may be retained in the divots 1210 by the magnet or beads 1705 may be chemically bound to divots 1210, as described above. The magnet may be moved or agitated to spread out beads 605 to ensure capture of one or more beads 1705 at each divot 1210. In another example, more than one magnet can be used to influence binding. For example, a stationary magnet can be used to influence binding of some beads, while agitating non-bound beads by moving another magnet can help the non-bound beads to locate a divot that has not been occupied by a bead.

FIG. 18 illustrates a side view of a partial cross-section of an embodiment in which a path or grid of recessed areas 1805 is provided on the droplet operations surface in association with electrode 1815. Beads 1325 settle into the recessed areas. This embodiment illustrates an aspect of the invention in which recessed areas are not divots. Various shaped recessed areas may replace divots in any of the embodiments described herein. Furthermore, in other embodiments, bead binding substances may be provided on a droplet actuator surface without the use of divots or recessed areas. For example, bead binding substances may be patterned on a droplet actuator surface such that beads will bind thereto, substantially immobilizing the beads. Further, while beads are illustrated here as spherical, any shape is suitable.

In another example, a mesh structure can be provided within the droplet actuator, and beads can settle in the mesh without contacting the surface of the electrodes. Areas of the mesh can also be functionalized with substances that promote binding of beads, e.g., as described elsewhere herein with respect to divots.

In yet another alternative embodiment, beads may be bound to a surface of a droplet actuator during manufacturing. For example, beads may be bound to a surface of a droplet actuator in paths, arrays or other patterns.

A variety of approaches are available for providing surface structure, such as divots and recessed areas, as described herein. For example, see U.S. Patent Publication No. 20070275193, entitled "Functional Materials and Novel Methods for the Fabrication of Microfluidic Devices," published on Nov. 29, 2007, the entire disclosure of which is incorporated herein by reference. The grid may be created, for example, in a silicon surface using a masking and etching technique.

In all of the foregoing examples, beads may be arrayed in a droplet on a droplet actuator. Arrayed beads may be substantially separated from a droplet, e.g., using droplet operations. Arrayed beads may be washed.

6.5 Bead Loading

FIG. 19 illustrates a cross-section of an embodiment in which beads are loaded from a reservoir into droplet operations gap 1920 of droplet actuator 1900. As illustrated, the droplet actuator 1900 includes bottom substrate 1905 associated with electrodes 1910, which are configured for conducting one or more droplet operations in droplet operations gap 1920. A top substrate 1915 is separated from bottom substrate 1905 by spacer 1916 in a generally parallel fashion to provide droplet operations gap 1920 between top substrate 1915 and bottom substrate 1905. Droplet operations gap 1920 provides a space for conducting droplet operations.

Top substrate 1915 includes a reservoir 1917 for holding liquid 1930 including beads 1935. Top substrate 1915 also includes one or more openings 1937 providing a liquid path for flowing beads and/or liquid from reservoir 1917 into gap 1920. Liquid 1930 may be a liquid in which beads 1935 are soluble and which is immiscible with a filler fluid (not shown) contained in gap 1920. Bottom substrate 1905 may be associated with one or more magnets 1907.

In operation, liquid 1930 with magnetically responsive beads 1935 dispersed therein is loaded into reservoir 1917. Liquid 1930 flows into opening 1937 and into proximity with one or more electrodes 1910. One or more proximate electrodes 1910 may be activated to cause liquid 1930 that has beads 1935 to flow into gap 1920. As magnetically responsive beads 1935 approach magnet 1907, the beads are attracted to and substantially immobilized on a top surface 1908 of substrate 1905. Ideally, the number of magnetically responsive beads 1935 dispersed in liquid 1930 is selected to yield a monolayer of beads 1935 on the top surface 1908 of substrate 1905. In another embodiment magnetically responsive beads 1935 may be pulled towards magnet 1907 even before liquid 1930 fills the opening 1937. In other words, with a powerful magnet, beads can be removed from liquid 1930 and attracted towards magnet 1907 even without requiring activation of an underlying electrode. Beads pulled from liquid 1930 may aggregate at a droplet operations surface in the magnetic field. The beads may be combined with other droplets, e.g., as described elsewhere herein with respect to beads "snapped" out of droplets, for conducting one or more steps of an assay.

While this embodiment has been illustrated with reference to use of a magnet to immobilize beads on a surface of the droplet actuator, it will be appreciated that in alternative embodiment, substances with binding affinity for the beads may be used to immobilize beads in place of magnetic fields. In yet another embodiment, magnetic fields may be used to attract beads to locations on the surface with substances having binding affinity for the beads. In this embodiment, the magnets may be removed after beads are bound to the surface. Further, various divots, recessed areas, and binding substances described elsewhere herein may be utilized in this embodiment as well.

6.6 Bead Stamping

FIGS. 20A and 20B illustrate a bead stamping embodiment of the invention. In this embodiment, droplet actuator 2000 is provided with substantially the same characteristics as droplet actuator 1900 that is described with reference to FIG. 9. However, top substrate 2015 of droplet actuator 2000 includes openings 2020 forming a liquid path from droplet operations gap 2022 to an exterior of top substrate 2015.

Stamping plate 2030 may be associated with one or more magnets 2040. Magnets 2040 may be arranged to align with openings 2020.

In operation, droplets 2042 including magnetically responsive beads 2043 may be subjected to droplet operations on droplet actuator 2000. Droplets 2042 including beads may be positioned in liquid in the vicinity of openings 2020. Liquid from droplets 2042 may flow through openings 2020, e.g., as a result of capillary forces and/or exterior pressure and/or vacuum sources. Stamping plate 2030 may be positioned in a generally parallel fashion with respect to top substrate 2015. Magnets 2040 associated with stamping plate 2030 may be generally aligned with openings 2020. Magnets 2040 attract magnetically responsive beads 2043 and immobilize them on a surface 2032 of stamping plate 2030. Stamping plate 2030 may then be removed for subsequent processing. As shown in FIG. 20B, in some cases, surface 2032 of stamping plate 2030 may include a bead binding substance, so that magnets 2040 may subsequently be removed. Bead binding substance retains beads 2043 in place.

In certain embodiments, the droplet-filler fluid interfacial tension may be adjusted to facilitate certain magnetically responsive bead based operations. Further, magnetic field strength and the concentration of the magnetically responsive beads may be adjusted as appropriate. Where the droplet is aqueous and the filler fluid is oil-based, interfacial tension may be influenced by the surfactant concentration in both the oil and water phase. Increasing surfactant concentration either phase will reduce the interfacial tension. When surfactant concentration in the oil phase is increased too much, even hydrophilic magnetically responsive beads tend to become immobilized in the presence of a magnet underneath and cannot be collected with a water droplet. This result occurs because of the low interfacial tension. Thus, in one embodiment, the surfactant concentration in the oil-based filler fluid is less than the amount that results in immobilization of beads in the oil phase.

In another embodiment, however, this side effect is used for stamping beads on a droplet actuator. For example, during manufacturing, bead stamping can be accomplished at various reactor zones on the droplet actuator. The reactor zones may, for example, be located on a droplet operations surface of a droplet actuator, and associated with one or more droplet operations electrodes of an arrangement of droplet operations electrodes. This approach would eliminate the time taken to transport the magnetically responsive bead-containing droplet to the reactor zone during operation of the droplet actuator. So, for example, droplet actuators with bead stamps can be prepared in advance of assay execution. Then, during operation, and the sample and the secondary antibody can be transported over the bead station using droplet operations followed by wash buffer and substrate. This approach would reduce the time-to-result for the end user.

6.7 Bead Sorting by Size

FIGS. 21 and 22 illustrate a bead sorting embodiment of the invention. FIG. 21 shows an arrangement of substrates 2110. Each substrate 2110 includes an arrangement of droplet operations electrodes 2115 and one or more electrodes 2120 configured to function as sieves (sieve electrodes 2120). Sieve electrodes 2120 permit vertical droplet operations. For example, droplet 2125 may be provided on an electrode 2115 adjacent to a sieve electrode 2120. By deactivating electrode 2115 and activating sieve electrode 2120, the droplet may be caused to flow onto sieve electrode 2120. Once on sieve electrode 2120, droplet 2125 may be transported horizontally onto another electrode on the same droplet actuator plane, or vertically through the sieve electrode onto another droplet actuator plane. For example, if droplet 2125 is located on sieve electrode 2120 on substrate 2110a, by deactivating sieve electrode 2120 on substrate 2110a and activating sieve electrode 2120 on substrate 2110b, droplet 2125 may be caused to flow from the plane of substrate 2110a onto sieve electrode 2120 of substrate 2110b.

As illustrated, sieve electrodes 2120 are vertically aligned, but it will be appreciated that such vertical alignment is not required. A droplet may be transported through a first sieve electrode on a first substrate onto a non-sieve electrode on a second plane using the same process. If desired, the droplet may then be transported using droplet operations to a second sieve electrode on the second plane, and be transported through the second sieve electrode to a third plane. Similarly, the droplet may be transported back and forth through a series of sieve electrodes between two planes. A bottom substrate will be provided that includes no sieve electrodes.

Each sieve electrode 2120 may be formed of a screen or mesh or any arrangement of one or more openings which permits liquids to pass therethrough. Seive electrodes 2120 may, for example, be formed of the same electrically conductive material as solid electrodes 2115. Each sieve electrode 2120 contains one or more small openings. The openings may, in some embodiments, be substantially evenly spaced and of uniform size. Depending on the size of the openings (i.e., the mesh size) of each sieve electrode 2120 permits beads up to a certain limiting size to pass through. Beads having a size greater than the threshold size are restrained from passing through. For example, the openings of each sieve electrode 2120 may be a few microns square. The mesh size of each sieve electrode 2120 of substrates 2110a, 2110b, and 2110c may differ in order to be used to sort differently sized beads. For example, FIG. 21 shows a droplet 2125 that may contain different sized beads to be sorted. More details of the bead sorting method are shown in FIG. 22.

FIG. 22 shows sieve electrodes 2120a, 2120b, and 2120c of substrates 2110a, 2110b, and 2110c, respectively, of droplet actuator 2100, and illustrates the method of sorting beads. Sieve electrodes 2120a, 2120b, and 2120c provide first, second and third levels of sorting, respectively. For example, in the illustrated embodiment, openings in sieve electrode 2120a are larger than openings in sieve electrode 2020b, which are larger than openings in sieve electrode 2020c. While the sieve electrodes are shown as being spaced apart, ideally, they will be sufficiently close, that a droplet resting on an activated sieve electrode will extend through the sieve electrode and slightly contact an underlying or overlying electrode. In this manner, when the underlying or overlying electrode is activated and the sieve electrode is deactivated, the droplet will be caused to flow through the sieve electrode and onto the underlying or overlying electrode. Sieve electrodes may be coated with a dielectric material. The dielectric material may be hydrophobic or may be coated with a hydrophobic coating, such as fluorinated polymer. By activating sieve electrode 2120b and deactivating sieve electrode 2120a, droplet 2125 may be caused to flow through the openings of sieve electrode 2120a. Beads 2230 may be retained atop sieve electrode 2120a, while droplet 2125 that contains beads 2232 and beads 2234 passes through sieve electrode 2120a onto sieve electrode 2120b. Next, by activating sieve electrode 2120c and deactivating sieve electrode 2120b, droplet 2125 may be caused to flow through the openings of sieve electrode 2120b. Beads 2232 may be retained atop sieve electrode 2120b, while droplet 2125 that contains beads 2234 only passes through sieve electrode 2120b onto sieve electrode 2120c. Next, droplet 2125 may be caused to flow through the mesh of sieve electrode 2120c by activating another electrode (not shown) below electrode 2120c. Alternatively, droplet 2125 may be transported away from sieve electrode 2120c on the same electrode plane using droplet operations mediated by adjacent electrodes 2115. Beads 2234 may be retained atop sieve electrode 2120c.

In some embodiments, arrangements of sieve electrodes are used to transport droplets from one plane of a multi-tiered droplet actuator to another plane of a multi-tiered droplet actuator without filtering beads or other materials.

6.8 Bead Localization & Washing

Gravity can be used to localize beads within a droplet. For example, beads can be concentrated in a droplet by positioning a droplet in a vertical position with respect to gravitational force. Dense beads, such as metal beads, can be used to cause the beads to settle in a bottom region of the droplet, e.g., against a bottom meniscus. A top portion of the droplet may then be split off to yield two daughter droplets: a top daughter droplet substantially lacking in beads and a bottom daughter droplet including substantially all of the beads from the parent droplet. This approach is useful, among other things, for merge-and-split wash protocols, in which successive wash droplets are merged with the bead-containing droplet and split off to yield a droplet including the beads with one or more unwanted substances removed from the presence of the beads.

FIG. 23 illustrates such an operation. Electrode arrangement 2301 provides droplet operations electrodes 2302 in a path oriented vertically or substantially vertically with respect to gravitational force. As shown in FIG. 23A, parent droplet 2305 including beads is maintained in position along electrode arrangement 2301 by activated electrodes (designated "ON"). In this position, dense beads 2308 are localized in a bottom region of droplet 2305. FIG. 23B shows deactivation (designated "OFF") of an intermediate electrode 2310 to separate droplet 2305 into two daughter droplets 2325 and 2326. As shown in FIG. 23C, daughter droplet 2325 is substantially lacking in beads, and bottom daughter droplet includes substantially all of the beads.

Similarly, buoyancy can be used to localize beads within a droplet. For example, beads can be concentrated in a droplet by positioning a droplet in a vertical position with respect to gravitational force. Beads that are relatively buoyant can be used to cause the beads to rise to a top region of the droplet, e.g., against a top meniscus of the droplet. The top portion of the droplet may then be split off to yield two daughter droplets: a bottom daughter droplet substantially lacking in beads and a top daughter droplet including substantially all of the beads from the parent droplet. This approach is also useful, among other things, for merge-and-split wash protocols, e.g., as described above.

In another embodiment, settling beads and buoyant beads can be localized to a magnet that can be stationary or in a state of motion such that the magnetic force prevents beads from settling at the bottom or towards the top. Beads may be settled into a magnetic field and/or floated to a magnetic field. The magnet can be moved up and down to transport magnetic beads back and forth within the droplet. A magnet may be used to separate magnetically responsive beads from buoyant or settling beads that are non-magnetic or weakly magnetic. For example, a mix of dense beads, some magnetically responsive and some not substantially magnetically responsive, may be settled in a droplet, the magnetically responsive beads being restrained by a magnetic field, while the magnetically non-responsive beads are permitted to continue to settle within the droplet. Similarly, a mix of buoyant beads, some magnetically responsive and some not substantially magnetically responsive, may be floated in a droplet, the magnetically responsive beads being restrained by a magnetic field, while the magnetically non-responsive beads are permitted to continue to rise within the droplet. Moreover, a mix of buoyant and dense beads, some magnetically responsive and some not substantially magnetically responsive, may be floated/settled in a droplet, the magnetically responsive beads being restrained by a magnetic field, while the magnetically non-responsive beads are permitted to continue to sink or rise within the droplet. The droplet may be split using droplet operations (e.g., by deactivating electrodes between each group of beads) to yield a droplet comprising buoyant magnetically non-responsive beads, a droplet comprising magnetically responsive beads, and a droplet comprising dense magnetically non-responsive beads.

In another embodiment, the combined effects of magnetic field and gravity may be used to separate magnetically responsive beads from a droplet. The interfacial tension of the droplet, magnetic pull force, concentration and mass of the magnetically responsive beads, may be adjusted to effect the separation. Similarly, the combined effects of magnetic field and centrifugal force may be used to separate magnetically responsive beads from a droplet. The interfacial tension of the droplet, magnetic pull force, concentration and mass of the magnetically responsive beads, and centrifugal force may be adjusted to effect the separation.

FIG. 24 illustrates such an operation. Electrode path 2401 is positioned vertically with respect to gravitational force. As shown in FIG. 24A, parent droplet 2405 including beads is maintained in position along electrode path 2401 by activated electrodes (designated "ON"). In this position, buoyant beads 2408 are localized in a top region of droplet 2405. FIG. 24B shows deactivation (designated "OFF") of an intermediate electrode 2410 to separate droplet 2405 into two daughter droplets 2425 and 2426. FIG. 24C shows daughter droplet 2425 is substantially lacking in beads, and daughter droplet 2426 includes substantially all of the beads.

In a related embodiment, buoyant beads are separated from dense beads. A droplet may be provided including a first set of beads which are less dense than the droplet medium (buoyant beads) and a second set of beads which are more dense than the droplet medium (dense beads).

The droplet may be elongated and arranged vertically as illustrated in FIGS. 23 and 24. The dense beads will settle to the bottom of the droplet, and the buoyant beads will rise to the top of the droplet. The droplet may be split to produce a daughter droplet including substantially all of the dense beads and another daughter droplet including substantially all of the buoyant beads. The vertically oriented, elongated droplet may be agitated to ensure separation of the buoyant beads from the dense beads, e.g., using a sonicator or by conducting droplet operations using the droplet, such as transporting the droplet back and forth on the electrode configuration or repeatedly splitting and merging the droplet on the electrode configuration.

In another embodiment, a droplet may include a set of magnetic beads, a set of non-magnetic charged beads, a set of non-magnetic dense beads, and a set of non-magnetic buoyant beads. The droplet may be elongated and arranged vertically as illustrated in FIGS. 23 and 24. The buoyant and dense beads would be substantially separated to the top and bottom of the droplet respectively. By applying a magnetic field, the magnetic beads can be immobilized in another region of the droplet, while the non-magnetic electrically charged beads may localized to another region of the droplet using electrophoresis. The elongated droplet can further be separated into multiple daughter droplets, e.g., by deactivating electrodes between the localized beads. The result is a set of daughter droplets, each containing a substantially high concentration of a particular set of beads.

6.9 Emulsification and Resuspension of Beads in Droplets

In another embodiment, beads can be suspended using a low interfacial tension liquid, such that when subjected to droplet operations within a droplet actuator partially or completely filled with a filler fluid, an emulsion of beads is formed. FIG. 25 illustrates this aspect of the invention. FIG. 25A shows clumped beads 2505 in starting droplet 2510 on reservoir electrode 2515. FIGS. 25A and 25B show that one or more low interfacial tension droplets 2520 formed using a liquid with low interfacial tension (relative to the liquid of starting droplet 2510) are combined with starting droplet 2510. The low interfacial tension droplet(s) 2520 mix with droplet 2510 to yield a new droplet 2525 having reduced interfacial tension relative to starting droplet 2510. FIG. 25C shows that upon activation of reservoir electrode 2515, an emulsion including droplets 2530 is formed due to the reduced interfacial tension of droplet 2525 caused by the addition of the low interfacial tension liquid droplet(s) 2520.

On the activated electrode, the low interfacial tension liquid forms into tiny droplets formed because the interface is not stable enough to retain the liquid as one big droplet. Once the emulsion is formed, and the beads are more or less uniformly distributed in the emulsified droplets, a high-interfacial tension liquid may be merged with the emulsion resulting in the reformation of a high interfacial tension droplet 2535 that has beads resuspended in it, as shown in FIG. 25D. The high-interfacial tension liquid is selected to neutralize the effect of the low-interfacial tension liquid and maintain a stable droplet-oil interface.

In one embodiment, this aspect of the invention relates to a method of forming an emulsion by providing a low interfacial tension liquid on a droplet operations surface and activating an electrode beneath the surface. In one aspect of this embodiment, the emulsion comprises water droplets in an oil-based filler fluid. In another aspect, the droplets in the emulsion may include one or more beads.

6.10 Concentrating Beads

As discussed above, droplet operations including beads are influenced by the interfacial tension of the droplet-filler fluid interface. For example, an aqueous droplet that (a) is on a droplet actuator, (b) is in the presence of a magnetic field, (c) is in an oil based filler fluid, and (d) has relatively large bead load, may tend to snap off the magnetically responsive beads as the droplet is transported away from a magnet. This effect can be controlled by controlling the concentration of surfactant in the bead-containing droplet. For example, if it is desirable to remove the beads from the presence of a magnetic field, the bead-containing droplet can be combined with a droplet having a lower concentration of surfactant relative to the bead-containing droplet. In this manner, the surfactant concentration in the bead-containing droplet can be reduced, and the interfacial tension can be increased, so that the beads can be removed from the magnet by using droplet operations to transport the bead-containing away from the magnetic field. Surfactant concentration can also be reduced using a merge-and-split wash protocol using a wash buffer with reduced or no surfactant relative to the bead-containing droplet. Similarly, if snapping off the beads is desirable, this goal can be achieved by increasing the concentration of surfactant in the droplet, e.g., by merging the bead-containing droplet with a droplet having a higher surfactant concentration relative to the surfactant concentration of the bead-containing droplet. Alternatively, the droplet may be heated to reduce the interfacial tension.

A large concentration of magnetically responsive beads can be used to assist the splitting of a droplet by snapping off the large mass of beads at a magnet station on a droplet actuator. During a droplet transport operation, the large mass of beads will break off on the magnet, surrounded by a minimal amount of liquid from the droplet. The mass of magnetically responsive beads snapped off from the droplet will generally be immobilized to the center of the magnet while the liquid component (supernatant) that is split off can be transported using droplet operations to waste or to downstream processing. An advantage of this approach is that it results in almost complete liquid removal from the beads. This effect is useful for increasing the efficiency of a merge-and-split bead washing protocol, e.g., as described above.

Beads can be concentrated on the droplet actuator by transporting a series of bead-containing droplets into the presence of a magnetic field that immobilizes the beads. Excess liquid can be split off using droplet operations. Beads may be added until the bead concentration is sufficient to snap off when the bead-containing droplet is transported away from the magnetic field, thereby leaving the beads behind in the presence of the magnetic field. By having a very high concentration of magnetically responsive beads, it is possible to split off only the highly concentrated beads with a minimal amount of liquid around them. When the highly concentrated bead solution is transported away from a magnet, the beads tend to get attracted to the trailing edge of the droplet and a highly concentrated bead sludge is snapped. A fresh wash buffer droplet can be added and the method repeated as needed until washing is complete.

6.11 Systems

As will be appreciated by one of skill in the art, the invention may be embodied as a method, system, or computer program product. Accordingly, various aspects of the invention may take the form of hardware embodiments, software embodiments (including firmware, resident software, microcode, etc.), or embodiments combining software and hardware aspects that may all generally be referred to herein as a "circuit," "module" or "system." Furthermore, the methods of the invention may take the form of a computer program product on a computer-usable storage medium having computer-usable program code embodied in the medium.

Any suitable computer useable medium may be utilized for software aspects of the invention. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Computer program code for carrying out operations of the invention may be written in an object oriented programming language such as Java, Smalltalk, C++ or the like. However, the computer program code for carrying out operations of the invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

Certain aspects of invention are described with reference to various methods and method steps. It will be understood that each method step can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the methods.

The computer program instructions may also be stored in a computer-readable memory that can direct a computer or other programmable data processing apparatus to function in a particular manner, such that the instructions stored in the computer-readable memory produce an article of manufacture including instruction means which implement various aspects of the method steps.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing various functions/acts specified in the methods of the invention.

7 CONCLUDING REMARKS

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation, as the present invention is defined by the claims as set forth hereinafter.

We claim:

1. A method of reducing a liquid volume surrounding one or more magnetically responsive beads, the method comprising:
   (a) providing a droplet comprising the one or more magnetically responsive beads;
   (b) exposing the one or more magnetically responsive beads in the droplet to a first region of a magnetic field; and
   (c) separating the droplet from the first region of the magnetic field via electrowetting, the one or more magnetically responsive beads remaining in a subdroplet atop an electrowetting electrode in the magnetic field.

2. The method of claim 1 further comprising heating the droplet to a temperature which permits the one or more magnetically responsive beads to break away from the droplet.

3. The method of claim 1 further comprising adjusting the droplet to a shape which permits the one or more magnetically responsive beads to break away from the droplet.

4. The method of claim 1 further comprising adjusting the droplet to an interfacial tension which permits the one or more magnetically responsive beads to break away from the droplet.

5. The method of claim 1 further comprising adding beads to the droplet until a mass of beads is accumulated which permits the one or more magnetically responsive beads to break away from the droplet.

6. The method of claim 1 further comprising adjusting the position and/or strength of a magnetic field in proximity to the droplet until one or more magnetically responsive beads breaks away from the droplet.

7. The method of claim 1 further comprising adjusting the position of the droplet in relation to a magnetic field until one or more magnetically responsive beads breaks away from the droplet.

8. The method of claim 1 wherein the droplet comprises a wash buffer.

9. The method of claim 1 wherein the droplet comprises one or more target substances for which at least a subset of the one or more beads has affinity.

10. The method of claim 1 wherein the one or more magnetically responsive beads remaining in the magnetic field is/are surrounded by liquid from the droplet.

11. The method of claim 1 wherein the one or more magnetically responsive beads is/are separated from the droplet during step 1(b).

12. The method of claim 1 wherein the one or more magnetically responsive beads is/are separated from the droplet during step 1(c).

13. A method of reducing a liquid volume surrounding one or more magnetically responsive beads, the method comprising:
   (a) providing a droplet comprising the one or more magnetically responsive beads;
   (b) exposing the one or more magnetically responsive beads in the droplet to a first region of a magnetic field; and
   (c) separating the droplet from the first region of the magnetic field via electrowetting, the one or more magnetically responsive beads remaining in a subdroplet atop an electrowetting electrode in the magnetic field, wherein separating the droplet from the first region of the magnetic field comprises magnetically attracting beads:
      (i) from a droplet positioned at least partially in a droplet operations gap of a droplet actuator; and
      (ii) through an opening in a substrate of the droplet actuator to a locus which is exterior to the droplet operations gap.

14. The method of claim 1 wherein the one or more magnetically responsive beads is/are snapped out of the droplet as the droplet is transported away from the first region of the magnetic field.

15. The method of claim 1 wherein the one or more magnetically responsive beads is/are snapped out of the droplet while the droplet is in proximity to the first region of the magnetic field.

16. The method of claim 11 wherein during the separation, the droplet is restrained from following the one or more magnetically responsive beads by a surface property of an underlying substrate.

17. The method of claim 16 wherein during the separation, the surface property of the underlying substrate causes the droplet to remain in a substantially stationary position.

18. The method of claim 16 wherein during the separation, the surface property of the underlying substrate causes the droplet to move closer to the first region of the magnetic field.

19. The method of claim 16 wherein during the separation, the surface property of the underlying substrate causes the droplet to move away from the first region of the magnetic field.

20. The method of claim 16 wherein the surface property of the underlying substrate is mediated by an electrode.

21. The method of claim 20 wherein the electrode is underlying the substrate.

22. The method of claim 1 wherein during the separation, the droplet is heated.

23. The method of claim 1 wherein during the separation, the droplet is surrounded by a liquid filler fluid that is substantially immiscible with the droplet.

24. The method of claim 1 wherein following the separation, the one or more magnetically responsive beads remain(s) in the first region of the magnetic field.

25. The method of claim 1 wherein following the separation, the one or more magnetically responsive beads is/are caused by the magnetic field to relocate from the first region of the magnetic field to a second region of the magnetic field.

26. The method of claim 1 wherein exposing the one or more magnetically responsive beads in the droplet to a first region of a magnetic field comprises transporting the droplet into the first region of the magnetic field.

27. The method of claim 1 wherein exposing the one or more magnetically responsive beads in the droplet to a first region of a magnetic field comprises transporting the first region of the magnetic field into proximity with the one or more magnetically responsive beads.

28. The method of claim 1 wherein separating the droplet from the first region of the magnetic field comprises transporting the droplet away from the first region of the magnetic field.

29. The method of claim 1 wherein separating the droplet from the first region of the magnetic field comprises moving the first region of the magnetic field away from the droplet.

30. The method of claim 1 wherein separating the droplet from the first region of the magnetic field comprises eliminating or shielding the magnetic field.

31. The method of claim 1 further comprising concentrating a target substance on the one or more magnetically responsive beads by contacting the one or more magnetically responsive beads with a sample droplet.

32. The method of claim 31 further comprising separating the sample droplet from the first region of the magnetic field, the one or more magnetically responsive beads remaining in the magnetic field.

33. The method of claim 1 further comprising washing the one or more magnetically responsive beads by contacting the one or more magnetically responsive beads with a wash droplet.

34. The method of claim 33 further comprising separating the wash droplet from the first region of the magnetic field, the one or more magnetically responsive beads remaining in the magnetic field.

35. The method of claim 1 wherein providing a droplet comprising one or more magnetically responsive beads comprises providing the droplet in a droplet operations gap of a droplet actuator, wherein the droplet is subject to one or more droplet operations.

36. The method of claim 35 wherein exposing the one or more magnetically responsive beads in the droplet to a first region of a magnetic field comprises transporting the droplet using electrode-mediated droplet operations into the first region of the magnetic field.

37. The method of claim 35 wherein exposing the one or more magnetically responsive beads in the droplet to a first region of a magnetic field comprises transporting the first region of the magnetic field into proximity with the one or more magnetically responsive beads.

38. The method claim 35 wherein separating the droplet from the first region of the magnetic field comprises transporting the droplet using electrode-mediated droplet operations away from the first region of the magnetic field.

39. The method of claim 35 wherein separating the droplet from the first region of the magnetic field comprises transporting the first region of the magnetic field away from the one or more magnetically responsive beads.

40. The method of claim 35 wherein the one or more droplet operations is/are mediated by one or more electrodes.

41. The method of claim 1 wherein following separating the droplet from the first region of the magnetic field, the droplet is presented to a detector or detection window for detection of a property of and/or signal from the droplet.

42. The method of claim 1 wherein:
(a) the one or more magnetically responsive beads remaining in the magnetic field is positioned in a droplet atop an electrowetting electrode;
(b) the electrowetting electrode has a footprint; and
(c) the droplet has a footprint which is smaller than the footprint of the electrowetting electrode.

* * * * *